(12) United States Patent
Gillespie et al.

(10) Patent No.: US 6,746,867 B1
(45) Date of Patent: Jun. 8, 2004

(54) MAMMALIAN MESODERM INDUCTION EARLY RESPONSE (MIER) GENE FAMILY

(75) Inventors: Laura Lee Gillespie, St. John's (CA); Gary David Paterno, St. John's (CA)

(73) Assignee: Genesis Group Inc., St. John's (CA)

( * ) Notice: Subject to any disclaimer, the term of this patent is extended or adjusted under 35 U.S.C. 154(b) by 0 days.

(21) Appl. No.: 09/170,984

(22) Filed: Oct. 13, 1998

(30) Foreign Application Priority Data

Oct. 10, 1997 (CA) .............................................. 2212985
Apr. 21, 1998 (CA) .............................................. 2229440

(51) Int. Cl.$^7$ .......................... C12Q 1/68; C07H 21/04; C12N 15/85
(52) U.S. Cl. .......................... 435/375; 435/6; 435/91.1; 435/366; 435/320.1; 435/375; 536/23.1; 536/24.31; 536/24.33; 536/24.5
(58) Field of Search .......................... 435/6, 91.1, 91.4, 435/325, 354, 366, 375, 320.1; 536/23.1, 24.3, 24.5; 514/44

(56) References Cited

PUBLICATIONS

Branch, TIBS 23: 45–50, Feb. 1998.*
Flanagan et al., Nature Biotech 17: 48–52, Jan. 1999.*
Sagata et al, Nature 335: 519–525, Oct. 1988.*
James A. Wells, Additivity of Mutational Effects in Proteins, BIOCHEMISTRY, vol. 29, No. 37 Sep. 18, 1990, pp. 8509–8517.*
Peer Bork, Powers and Pitfalls in Sequence Analysis: The 70% Hurdle, Genome Research, pp. 398–400.*
Jeffrey Skolnick et al., From genes to protein structure and function: novel applications of computational approaches in the genomic era, Trends in Biotech 18 (1) pp. 34–39.*
Doerks, et al. Protein annotation: detective work for function prediction, TIG Jun. 1998 vol. 14 No. 6, pp. 248–250.*
Temple F. Smith et al., The challenges of genome sequence annotation or The devil is in the details, Nature Biotechnology, vol. 15, pp. 1222–1223.*
Steven E. Brenner, Errors in genome annotation, TIG Apr. 1999, vol. 15, No. 4, pp. 132–133.*
Bork et al. Go hunting in sequence databases but watch out for the traps, TIG Oct. 1996, vol. 12, No. 10, pp. 425–427.*
T05868—Standard; DNA.*
Aasland et al., "The SANT domain, a putative DNA–binding domain in the SWI–SNF and ADA complexes, the transcriptional co–repressor N–CoR and TFIIIB", *Trends Biochem. Sci.*, 21:87–88 (1996).
Andrew Baird et al., The Fibroblast Growth Factor Family, The New York Academy of Sciences, New York, NY, vol. 638, Dec. 20, 1991.
Pasquale Delli Bovi et al., "Isolation of a rearranged human transforming gene following transfection of Kaposi sarcoma DNA", *Proc. Natl. Acad. Sci. USA,*. 84, pp. 5660–5664 (1987).

David G. Fernig et al., "Fibroblast Growth Factors and Their Receptors: An Information Network Controlling Tissue Growth, Morphogenesis and Repair", *Prog. Growth Factor Res.*, 5, 353–377 (1994).
L.L. Gillespie et al., "Analysis of competence: receptors for fibroblast growth factor in early Exnopus embryos," *Development*, 106, 203–208, 1989.
L.L. Gillespie et al., "Intracellular signalling pathways involved in mesoderm induction by FGF," *Mech. Dev.*, 38, 99–107 (1992).
L.L. Gillespie et al., "Cloning of a Fibroblast Growth Factor Receptor 1 Splice Variant from Xenopus Embryos That Lacks a Protein Kinase C Site Important for the Regulation of Receptor Activity", *The Journal of Biological Chemistry*, vol. 270, No. 39, 22758–22763 (1995).
Rebecca S. Hartley et al., "Rapid Communication MAP Kinase is Activated During Mesoderm Induction in *Xenopus laevis,*" *Development Biology*, 163, 521–524 (1994).
Amy E. Krafft et al., "Optimization of the Isolation and Amplification of RNA from Formalin–fixed, Paraffin–embedded Tissue: The Armed Forces Institute of Pathology Experience and Literature Review", *Molecular Diagnosis*, vol. 2, No. 3, 217–230 (1997).
R. Moore et al., "Sequence, topography and protein coding potential mouse int–2: a putative oncogene activated by mouse mammary tumour virus," *EMBO J.*, 5:919–924 (1986).
G. Neufeld et al., "Expression of Human Basic Fibroblast Growth Factor cDNA in Baby Hamster Kidney–derived Cells Results in Autonomous Cell Growth," *J. Cell Biol.*, 106, 1385–1394 (1988).

(List continued on next page.)

*Primary Examiner*—John L. LeGuyader
*Assistant Examiner*—Janet Epps-Ford
(74) *Attorney, Agent, or Firm*—Gray Cary Ware & Freidenrich, LLP; Lisa A. Haile

(57) ABSTRACT

The invention relates to a family of mammalian genes that are transcribed in the immediate early phase following exposure to Fibroblast Growth Factors (FGF) during mesoderm induction, termed Mesoderm Induction Immediate Early Response (MIER) genes. Defining features of the members of this family include that these genes are a) transcribed in response to fibroblast growth factors (FGF); b) are expressed within 40 minutes of FGF treatment; and c) do not require protein synthesis for transcription. There are at least eleven members within this family.

The invention relates generally to compositions of and diagnostic methods relating to the M-MIER gene family, cDNA, nucleotide fragments, polypeptides coded thereby, recombinant host cells and vectors containing M-MIER encoding polynucleotide sequences, recombinant M-MIER polypeptides, and antibodies. By way of example, the invention discloses the cloning and functional expression of different M-MIER polypeptides. The invention also includes methods for using the isolated, recombinant polynucleotides, polypeptides, and antibodies directed thereto in assays designed to select substances which interact with M-MIER polypeptides for use diagnostic and therapeutic applications in addition to drug design and DNA vaccination methodologies.

33 Claims, 31 Drawing Sheets

OTHER PUBLICATIONS

Gary D. Paterno et al., "cDNA Cloning of a Novel, Developmentally Regulated Immediate Early Gene Activated by Fibroblast Growth Factor and Encoding a Nuclear Protein," *The Journal of Biological Chemistry*, vol. 272, No. 41, 25591–25595 (1997).

Paula J. Ryan et al., "Phosphorylation of Phospholipase Cγ1 and Its Association with the FGF Receptor Is Developmentally Regulated and Occurs during Mesoderm Induction in *Xenopus laevis*," *Developmental Biology*, 166, 101–111 (1994).

Reiko Sasada et al., "Transformation of Mouse BALB/c 3T3 Cells with Human Basic Fibroblast Growth Factor cDNA," *Molecular and Cellular Biology*, 8, 588–594 (1988).

J.M.W. Slack et al., "Mesoderm Induction in Early Xenopus Embryos by Heparin–Binding Growth Factors," *Nature*, 326, 197–200 (1987).

J.C. Smith et al., "Expression of a Xenopus Homolog of Brachyury (T) Is An Immediate–Early Response to Mesoderm Induction," *Cell*, vol. 67, 79–87 (1991).

Yashushi Toh et al., "A Novel Candidate Metastasis–associated Gene, mta1, Differentially Expressed in Highly Metastatic Mammary Adenocarcinoma Cell Lines," *The Journal of Biochemical Chemistry*, 269:22958–22963 (1994).

Yashushi Toh et al., "Analysis of the complete sequence of the novel metastasis–associated candidate, mta1, differentially expressed in mammary adenocarcinoma and breast cancer cell lines," *Gene*, 159:97–104 (1995).

Yashushi Toh et al., "Overexpression of the MTA1 Gene in Gastrointestinal Carcinomas: Correlation with Invasion and Metastasis", *Int. J. Cancer* 74:459–463 (1997).

George von Dassow et al., "Induction of the Xenopus organizer: expression and regulation of Xnot, a novel FGF and activin–regulated homeo box gene," *Genes Dev.*, 7:355–356 (1993).

Xiaolong Yang et al., "Expression of Cellular Genes in HPV16–Immortalized and Cigarette Smoke Condensate–Transformed Human Endocervical Cells", *Journal of Cellular Biochemistry*, 66:309–321 (1997).

* cited by examiner

```
   1        TTGCATCAGCTGCAGATCAAGGTTAAAATATATATATCAGAAGAATACACAA
  53    ATAATTAAATTAAATGTCTCAAACAACTCCTTCCATATGAAGGCCTCTCTGTACCTGTGC
 113    AGCGTTTTTCAAAACAGAGCAAGGAATTCATACATTACAAATATATTTGTTGTGTCATAA
 173    GCTACAGAGAAAGTTATAGTGAAACCAACAAAACATAAATGACCCGTCAGTACGGCAAAC
 233    ATGGCGGAGCCTTCACTCAGGACCGCAAGCCCAGGTGGCTCGGCTGCATCAGATGACCAT
          M   A   E   P   S   L   R   T   A   S   P   G   G   S   A   A   S   D   D   H    20
 293    GAGTTTGAGCCATCAGCTGACATGCTTGTTCATGAATTTGATGATGAACAAACGTTGGAA
          E   F   E   P   S   A   D   M   L   V   H   E   F   D   D   E   Q   T   L   E    40
 353    GAAGAGGAGATGCTGGAGGGAGAAGTCAACTTCACTTCAGAAATAGAGCACCTTGAAAGA
          E   E   E   M   L   E   G   E   V   N   F   T   S   E   I   E   H   L   E   R    60
 413    GAAAGTGAAATGCCAATTGATGAATTATTGCGACTCTATGGTTATGGCAGTACAGTGCCA
          E   S   E   M   P   I   D   E   L   L   R   L   Y   G   Y   G   S   T   V   P    80
 473    CTACCAGGAGAAGAAGATGAGGAGGATATGGATAATGATTGTAACAGTGGCTGCAGTGGA
          L   P   G   E   E   D   E   E   D   M   D   N   D   C   N   S   G   C   S   G   100
 533    GAAATAAAGGATGAAGCTATTAAGGACTCTTCAGGACAGGAAGATGAAACACAGTCTTCA
          E   I   K   D   E   A   I   K   D   S   S   G   Q   E   D   E   T   Q   S   S   120
 593    AATGATGATCCTACTCCATCTTTTACATGTAGAGATGTACGAGAAGTAATCCGTCCACGT
          N   D   D   P   T   P   S   F   T   C   R   D   V   R   E   V   I   R   P   R   140
 653    CGGTGCAAGTATTTTGATACAAATCATGAAATAGAAGAGGAGTCTGAGGATGATGAGGAT
          R   C   K   Y   F   D   T   N   H   E   I   E   E   E   S   E   D   D   E   D   160
 713    TATGTACCTTCAGAAGATTGGAAAAAGGAAATTATGGTGGGATCCATGTTCCAGGCTGAA
          Y   V   P   S   E   D   W   K   K   E   I   M   V   G   S   M   F   Q   A   E   180
 773    ATTCCAGTTGGTATTTGCAAATACAGAGAAACAGAGAAAGTATATGAAAATGATGATCAG
          I   P   V   G   I   C   K   Y   R   E   T   E   K   V   Y   E   N   D   D   Q   200
 833    CTCCTCTGGAATCCAGAATATGTAATGGAAGAAAGAGTAATAGACTTCTTAAATGAGGCA
          L   L   W   N   P   E   Y   V   M   E   E   R   V   I   D   F   L   N   E   A   220
 893    TCCAGAAGGACTTGTGAAGAGAGAGGGCTAGATGCTATTCCTGAAGGATCCCACATAAAG
          S   R   R   T   C   E   E   R   G   L   D   A   I   P   E   G   S   H   I   K   240
 953    GACAATGAGCAGGCCCTATATGAACATGTAAAATGCAATTTTGACACAGAAGAGGCATTG
          D   N   E   Q   A   L   Y   E   H   V   K   C   N   F   D   T   E   E   A   L   260
1013    AGAAGACTAAGATTTAATGTCAAAGCCGCCAGAGAAGAACTTTCCGTTTGGACTGAAGAA
          R   R   L   R   F   N   V   K   A   A   R   E   E   L   S   V   W   T   E   E   280
1073    GAATGTAGAAATTTTGAGCAAGGTCTAAAAGCTTATGGCAAAGATTTCCACTTGATTCAG
          E   C   R   N   F   E   Q   G   L   K   A   Y   G   K   D   F   H   L   I   Q   300
1133    GCTAACAAGGTAAGGACAAGGTCTGTTGGAGAATGTGTGGCATTCTACTACATGTGGAAA
          A   N   K   V   R   T   R   S   V   G   E   C   V   A   F   Y   Y   M   W   K   320
1193    AAATCAGAACGTTATGACTTCTTTGCCCAACAAACACGATTTGGAAAAAAGAAGTATAAT
          K   S   E   R   Y   D   F   F   A   Q   Q   T   R   F   G   K   K   K   Y   N   340
1253    CTACATCCTGGTGTAACGGATTACATGGATCGTCTTTTGGATGAAAGCGAAAGTGCTACC
          L   H   P   G   V   T   D   Y   M   D   R   L   L   D   E   S   E   S   A   T   360
1313    TCCAGCAGGGCGCCATCTCCCCCACCAACTACCTCCAACAGCAATACTAGTCAATCCGAA
          S   S   R   A   P   S   P   P   P   T   T   S   N   S   N   T   S   Q   S   E   380
1373    AAGGAGGACTGTACAGCCAGTAACAACACTCAGAATGGAGTTTCTGTGAATGGCCCATGT
          K   E   D   C   T   A   S   N   N   T   Q   N   G   V   S   V   N   G   P   C   400
```

FIG. 1

```
1433    GCAATAACTGCATACAAAGATGAAGCCAAACAAGGGGTGCATTTAAATGGACCTACTATA
         A  I  T  A  Y  K  D  E  A  K  Q  G  V  H  L  N  G  P  T  I   420
1493    AGTAGCAGTGATCCCTCTTCGAATGAAACCGACACCAATGGGTATAATCGTGAAAATGTT
         S  S  S  D  P  S  S  N  E  T  D  T  N  G  Y  N  R  E  N  V   440
1553    ACGGACGATTCCAGATTTAGTCATACAAGTGGAAAAACTGACACAAATCCAGATGATACA
         T  D  D  S  R  F  S  H  T  S  G  K  T  D  T  N  P  D  D  T   460
1613    AACGAAAGGCCAATAAAAAGGCAACGTATGGACAGCCCTGGGAAGGAAAGTACAGGATCA
         N  E  R  P  I  K  R  Q  R  M  D  S  P  G  K  E  S  T  G  S   480
1673    TCTGAATTCTCTCAGGAAGTGTTTTCACATGGAGAGGTTTAAACATTTTGCAGATTTGAG
         S  E  F  S  Q  E  V  F  S  H  G  E  V  '   (SEQ ID NO:2)     493
1733    GGAAAACACATTTGGGGGGATGAAGAAATTTCTGGGGATCTTGGAACTTCAGGGTTTAT
1793    TAAATTATTTAGCAAGTTATTTTTTTGTATTATTTTTCTATTTGTCCCATGCACATTTGA
1853    GCCCCACAGAAGAGTGAAATATTTTGTGTAGTTGAATAGTGAAATTTTTGAAGCCCTCTG
1913    GAAAAGTAAGCAGCCTTGCAGATATTCAGCCTATGCCTGAATGCAGTTTGGCTTTACGTT
1973    ATCATTCGTTACATGAAGAAGGATCTTTAAATAGAAAAGAATTGTTCCAGAATATGTCT
```

FIG. 1 (continued)

nm-MIER S3

CTGCTCTCAGA TGCAATGA CAACA CTATCTCTATTCCAGGA TGACTTCAAGTC
AAA TGTTGA TGTTGTTTAGTTGCTAAG TTATGTCTGAC TCTTTTGCAAC CCCA T
GGA CTATAGCCCACCTCTGTCCATA GGAT TTCCCAGGCAAG AATACTGG ATG
GTTTGCCATTTCTCTAGGA AATCTTTCCAAC CCAG GGAC TGAAC CCAC ATCTT
GTGCTTGG CAAC CGAT TCTTTACCACTGAGC CACTAGGGAA GCCCTTAAAG TC
ATATA AAGTAA TGTTAA TTTCAGAAT GCTTTCATATCAAAGT TAAGA GCCCAG
ATAAA TTTTAAA TGGCTGTGAA TCCA TTGCAG CTATTCCCA CCAAG AGTTGG A
GTCTATTTTCAA CACTCTCCCCTTACTCTGGG CTGG ATCTATGAC TTTCTTTGG
CCAACAG ACTGTGCTACTTCAA TACTTACCTTCTTACC AGACA CTTCTATCTT
GTGAAGGAG CCTGAGAG CAG                    (SEQ ID NO:3)

nm-MIER S14

CTGCTCTCAGA AAAAT GCTATAGA GACG TATA TGAC ATAAA TAATCTGTG AT
GAAA CAATTTAGGT TTCATTAG CTTTTACA AAAAT GGAAAAAG TATGACCA T
GGTTGCACAG TTTGG CAAAC CATTTTTTCTATCATTCCTA CAAAA TACTACTG
AGTGTTACTGGA CACTGATA TGATTATTAAAGA TATTCTTTATATAAA TTGTA
TATCAATA AaTTATAATA TGCA GAGTA GGTTGcAG TTACCTACTTACCTACTTA
CAGAAGCAA TTATCACTAAAC TGCTGACA TGCCAGTTTGGT TGTTCAGCATAC
TTCAGTA CAAACA AGAAGC TTCTGGAGTTTCCAG TACA CTGCATTTTATACA A
ATGTA ACGTATAGG CTCATA AACCTAAAG CACA CTAG TTATTTAG ATTTACTA
CATACATAAA GATA CACAG CTGA GCAG
                                          (SEQ ID NO:4)

nm-MIER S16

TTCGTTTTGTTTCAGTAAAT AGTA TTTGCA TTTATTATGTATA CAGCAA AATA
GACATCTGATGCA AATTAGAAG TGTAGGCTGGT ACTAACA TGGCTGAGCTAG
AAGTTTAGGTAAGGAA AAGAT GAGGAAAAG AGACAG CTAGTGCTCATACTG
CATTGCCCCATTCCTTCAAAATG GAATG TAGGCCAA TTTTGTTGTCACAAA TT
CAGCAGA TAAAC ATCTTTCAATAA GGAAAT CACA GAAAAT ACTTGGAA TACT
GAGA ATTGAGAC AACGC AACAA TAATACTTTGTA CAGA TGCTGGCTGGT ACC
CTAAA TTTGTACCCACAG TATTCCCAG TTCATGCCTCAAG TAAAA TACAAAA T
ATAGAAGA TGCCCAG CAGTA ACGTTCAATG TAATGATTCAA GAGAT TGTCAG
AAAA AAATA CATATTAGAT ATGGCTCTGA TAAGGA ATGGG AGTCAAGTG TGA
TAACAGG AATGG CACA CCCTTCTTATAGTTAAG CAAGC TCTTTGCCACTTTAT
ATCAG CTTATTGCCCATGGA TAAGCA CCTGCTTCTCCTTTCCTGAAAGAA TTA
AGTGTAGTCCCAA CTTGGA CACCTAATATATGGTGAT TCAAAGCTGAA TATCC
AGGG AACAA CAGAA TATTCATCAAA GGAGTG TCCTTTATTATG TGAAGA ACC
ATTTT                                     (SEQ ID NO:5)

FIG. 2 (a)

nm-MIER S17

CTGATCCATGGTTTAAGTATAAATAATTGTTCACTTATATCTGTTTCAATCACCTTTCATT
GTAGTTCCCAAAATCTCGCCTAAATCATACATCTGCCCAACCAACCTTCTAACAGCAA
TGTTAGGGATGGATTCAAAAAGATCTTTGAGGAAATTGGGTGGCAGATACGCGCTAA
CAAAGATGAGTGATAGAAACACAATGGTGATTACTCCCAATCAGTATAATTCAAATAG
TATAATGGGTATAACAGTAATAGAGTACATGACATGTTAGGCACTTACTTTGCTGTGCC
AAAGGTATTCCCATCACTTTGTCTCTCAGAGACACCAACAGATAGCTGTGGCCTAATC
CCTATCTGTGTACCCTGCTTTAACCCAAACTAATTGACAAACTCGAAATCGATGGTGC
TAATTCACCACCCCCATCTATTGAGAGTACATGCTCTCCATGTTATGTTAGCAATAGGA
TAAATCCTTATTTTCTTTTTCCTATCTCCCTCTGGACTCCCCATGATCTCTATTTTCCCAA
TCGTCGGTTTCTTGCATCCTAAGTAATATCCTCTTCAGGATACACTCATGCCTGCTAGA
AGGATTAACAAATGAATTAGGCATGATAACGATTATTGCATGGATCAG
          (SEQ ID NO:6)

nm-MIER S24

CTGATCCATGCGTATAGCCTTGAATAATAAAGCTTTGCTCCCTCTAAATGACAAATACC
ACAATCCACTACTACCACCTATGACTGCACTTGAACTTACAAGTAACTAAGGGAACAA
GAGGGGGATAAGAAAACAGAAGTACAGAACTATCGCAATGACTGCTTTGTGATCTTA
TTTCCTACATGGATCAG                    (SEQ ID NO:7)

nm-MIER S30

TGATCCATGAAAAGTGTTAGTGACCAACCTTCTGGATATCTTCCATTCCCGAAACCTG
ATGATACTCAGTACTTTGACAAATTATTGGTTGATGTTATGAATCTACgCTAAGT
CCAGAAGAACAGAAAGAAAGAAAAATAATGAAATTATTGTTAAAAATAAAAGATGGC
ACACCTCCAATGAGGAAGGCTGCCTTGCGACAAATAACTGATAAAGCTCGTGAGTTT
GGAGCCGGTcCACTATTCAATCAGATCCTGCCTCTGCTGATGTCGCCAACACTTGAAG
ATCAAGAAAGACACTTGCTTGTTAAAGTTATTGATAGAATTTTGTATAAATTGGATGAC
TTGGTCCGCCCATATGTACATAAGATTCTTGTCGTTATTGAACCACTTCTGATTGATGA
AGACTATTATGCCAGAGTGGAAGGCAGAGAAATCATATCTAATTTAGCCAAGGCTGCT
GGTTTAGCTACAATGATTTCAACTATGCGACCAGATATTGATAACATGGATCAG
          (SEQ ID NO:8)

FIG. 2(b)continued

- ▨ Acidic activation domain
- ▦ Predicted nuclear localization signals
- ▥ Coiled - coil domain
- ▧ SANT domain
- ⊕ Predicted SH3 binding domain
- Y Predicted tyrosine phosphorylation site
- P Proline-directed phosphorylation site

A

C. elegans
Xenopus
Rat
Human

```
Xenopus      MAEPSLRTASPGGSAASDDHEFEPSADMLVHEFDDEQTLEEEEMLEGEVNFTSEIEHLER  60
             ESEMPIDELLRLYGYGSTVPLPGEEDEEDMDNDCNSGCSGEIKDEAIKDSSGQEDETQSS 120
C.elegans    NDDPTPSFTCRDVREVIRPRRCKYFDTNHEIEEESEDDEDYVPSEDWKKEIMVGSMFQAE 180
Rat          P-------+---+---+DD+DY-P--D--K--+------+
Human                                            K-EI-VG+-+QA+
                                                 K-EI-VG+-+QA+

Xenopus      IPVGICKYRETEKVYENDDQLLWNPEYVMEERVIDFLNEASRRTCEERGLDAIPEGSHIK 240
C.elegans    ---V-+-------E+-----DD-+LW                      P--G+---+
Rat          I-----+------E-+---+---+W---+-----+-+-+--ID
Human        I-----+------E-+---+---+W---+-----+-+-+--ID Xenopus      DNEQALYEHVKCNFDTEEALRRLRFNVKAAREELSVWTEEECRNFEQGLKAYGKDFHLIQ 300
C.elegansD+E-AL-----+-NFDTE+A-------F--+---R-+----+-E-E--+-FE+--L+-YGKDF-LI+
Rat                                              R+E+---W+---E---FE+--L+-YGKDF---IQ
Human                                             R+E+---W+---E---FE+--L+-YGKDF---IQ Xenopus      ANKVRTRSVGECVAFYYMWKKSERYDFFAQQTRFGKKKYNLHPGVTDYMDRLLDESESAT 360
C.elegans    ---++---R-VGE-++--+YY-WK-+--Y
Rat          -+-+---+S+----+--+YYMWK-++RY                T--GK+-Y--H-GV
Human        -+-+---+S+----+--+YYMWK-++RY                T--GK+-Y--H-GV SSRAPSPPPTTSNSNTSQSEKEDCTASNNTQNGVSVNGPCAITAYKDEAKQGVHLNGPTI 420
             SSSDPSSNETDNGYNRENVTDDSRFSHTSGKTDTNPDDTNERPIKRQRMDSPGKESTGS 480
             SEFSQEVFSHGEV    (SEQ ID NO:1)                             493
```

FIG. 4B

Artee/fER1 3-phase Translation

DNA sequence 504 b.p.   GGCTGAAATTCC ... TCCTGGTGTAAC   linear

```
1    /   1                              31   /   11
GGC TGA AAT TCC AGT TGG TAT TTG TAG ATA CAA AGA AAA TGA AAA AGT ATA TGA AAA TGA
gly OPA asn ser ser trp tyr leu AMB ile gln arg lys OPA lys ser ile OPA lys OPA
 ala glu ile pro val gly ile cys arg tyr lys glu asn glu lys val tyr glu asn asp
  leu lys phe gln leu val phe val asp thr lys lys met lys lys tyr met lys met met
61   /   21                             91   /   31
TGA TCA GCT CCT GTG GGA CCC TGA GTA CTT ACC AGA AGA TAA AGT GAT TAT ATT TCT TAA
OPA ser ala pro val gly pro OPA val leu thr arg arg OCH ser asp tyr ile ser OCH
 asp gln leu leu trp asp pro glu tyr leu pro glu asp lys val ile ile phe leu lys
  ile ser ser cys gly thr leu ser thr tyr gln lys ile lys OPA leu tyr phe leu lys
121  /   41                             151  /   51
AGA TGC ATC TAG AAG AAC AGG TGA TGA GAA GGG TGT AGA AGC AAT TCC TGA AGG ATC TCA
arg cys ile AMB lys asn arg OPA OPA glu gly cys arg ser asn ser OPA arg ile ser
 asp ala ser arg arg thr gly asp glu lys gly val glu ala ile pro glu gly ser his
  met his leu glu glu gln val met arg arg val AMB lys gln phe leu lys asp leu thr
181  /   61                             211  /   71
CAT AAA AGA CAA TGA ACA GGC TTT ATA TGA ATT GGT TAA TGC AAT TTt gat tac aga aga
his lys arg gln OPA thr gly phe ile OPA ile gly OCH cys asn phe asp tyr arg arg
 ile lys asp asn glu gln ala leu tyr glu leu val asn ala ile leu ile thr glu glu
  OCH lys thr met asn arg leu tyr met asn trp leu met gln phe OPA leu gln lys lys
241  /   81                             271  /   91
agc att gag aag att aga ttt atg taa agc agc tag aga gat atc tgt ttg gac aga gga
ser ile glu lys ile arg phe met OCH ser ser AMB arg asp ile cys leu asp arg gly
 ala leu arg arg leu asp leu cys lys ala ala arg glu ile ser val trp thr glu glu
  his OPA glu asp AMB ile tyr val lys gln leu glu arg tyr leu phe gly gln arg lys
301  /   101                            331  /   111
aga gtg tag aaa ttt tga aca agg gct gaa ggc cta tgg aga gga ttt tca ttt gat ttc
arg val AMB lys phe OPA thr arg ala glu gly leu trp arg gly phe ser phe asp phe
 glu cys arg asn phe glu gln gly leu lys ala tyr gly glu asp phe his leu ile ser
  ser val glu ile leu asn lys gly OPA arg pro met glu arg ile phe ile OPA phe his
361  /   121                            391  /   131
att cag gct taa taa agt ccg aac aag gtc agt tgg tga atg tgt agc att cta tta cat
ile gln ala OCH OCH ser pro asn lys val ser trp OPA met cys ser ile leu leu his
 phe arg leu asn lys val arg thr arg ser val gly glu cys val ala phe tyr tyr met
  ser gly leu ile lys ser glu gln gly gln leu val asn val AMB his ser ile thr cys
421  /   141                            451  /   151
GTG GAA AAA ATC TGA ACG TTA TGA TTT ctt tgc tca gca AAC ACG ATT TGG AAA GAA GAA
val glu lys ile OPA thr leu OPA phe leu cys ser ala asn thr ile trp lys glu glu
 trp lys lys ser glu arg tyr asp phe phe ala gln gln thr arg phe gly lys lys lys
  gly lys asn leu asn val met ile ser leu leu ser lys his asp leu glu arg arg asn
481  /   161
ATA TAA TCT ACA TCC TGG TGT AAC        (SEQ ID NO:13)
ile OCH ser thr ser trp cys asn
 tyr asn leu his pro gly val           (SEQ ID NO:14)
  ile ile tyr ile leu val OCH
```

FIG. 20

```
                                                                    GGGTCGGA
   9 CGCCAGCTGCGGACGCCAGCTGCGGCCGCCGCGGAGATGTGAGGCGGCAGTACGGCAAAT
  69 ATGGCGACATCTGTTGAATCTTCAAGTCCAGGAGGTTCAGCAACATCAGATGACCATGAA
      M  A  T  S  V  E  S  S  S  P  G  G  S  A  T  S  D  D  H  E    20
 129 TTTGGTCCATCAACTGACATGCTGGTTCATGATTTTGATGATGAACGAACATTAGAAGAG
      P  G  P  S  T  D  M  L  V  H  D  F  D  D  E  R  T  L  E  E    40
 189 GAAGAAATGATGGAAGGAGAAACAAACTTCAGCTCTGAAATAGAAGATCTTGCAAGGGAA
      E  E  M  M  E  G  E  T  N  F  S  S  E  I  E  D  L  A  R  E    60
 249 GGCGACATGCCAATTCATGAACTTCTCAGCCTTTATGGTTATGGTAGTACTGTTCGACTA
      G  D  M  P  I  H  E  L  L  S  L  Y  G  Y  G  S  T  V  R  L    80
 309 CCTGAAGAAGATGAGGAAGAGGAAGAAGAAGGAGAAGAAGGTGAAGATGATGAAGATGCT
      P  E  E  D  E  E  E  E  E  G  E  E  G  E  D  D  E  D  A   100
 369 GATAATGATGACAACAGTGGCTGTAGTGGGGAAAATAAAGAGGAGAATATAAAGGATTCA
      D  N  D  D  N  S  G  C  S  G  E  N  K  E  E  N  I  K  D  S   120
 429 TCAGGTCAGGAGGATGAAACTCAGTCTTCCAATGATGATCCATCACAATCTGTTGCTTCT
      S  G  Q  E  D  E  T  Q  S  S  N  D  D  P  S  Q  S  V  A  S   140
 489 CAAGATGCCCAGGAAATAATCCGCCCACGTCGATGTAAATATTTTGATACAAATAGTGAA
      Q  D  A  Q  E  I  I  R  P  R  R  C  K  Y  F  D  T  N  S  E   160
 549 GTAGAAGAAGAATCTGAAGAAGATGAAGATTATATTCCATCAGAAGACTGGAAAAAGGAG
      V  E  E  S  E  E  D  E  D  Y  I  P  S  E  D  W  K  K  E   180
 609 ATTATGGTGGGCTCCATGTTTCAAGCAGAAATTCCAGTTGGCATGTGTAGATACAAAGAA
      I  M  V  G  S  M  F  Q  A  E  I  P  V  G  M  C  R  Y  K  E   200
 669 AATGAAAAAGTATATGAAAATAGTGATCAGCTCCTGTGGGACCCTGAGTACTTACCAGAA
      N  E  K  V  Y  E  N  S  D  Q  L  L  W  D  P  E  Y  L  P  E   220
 729 GATAAAGTGATTATATTTCTTAAAGATGCATCTAGAAGAACAGGTGATGAGAAGGGTGTA
      D  K  V  I  I  F  L  K  D  A  S  R  R  T  G  D  E  K  G  V   240
 789 GAAGCAATTCCTGAAGGATCTCACATAAAAGACAATGAACAGGCTTTATATGAATTGGTT
      E  A  I  P  E  G  S  H  I  K  D  N  E  Q  A  L  Y  E  L  V   260
 849 AAATGCAATTTTGATACAGAAGAAGCATTGAGAAAGTTAAGATTTAATGTAAAAGCAGCT
      K  C  N  F  D  T  E  E  A  L  R  K  L  R  F  N  V  K  A  A   280
 909 AGAGAGGAATTATCTGTTTGGACAGAGGAAGAGTGTAGAAATTTTGAACAAGGGCTGAAG
      R  E  E  L  S  V  W  T  E  E  E  C  R  N  F  E  Q  G  L  K   300
 969 GCCTATGGAAAGGATTTTCATTTGATTCAGGCTAATAAAGTCCGAACAAGGTCAGTTGGT
      A  Y  G  K  D  F  H  L  I  Q  A  N  K  V  R  T  R  S  V  G   320
1029 GAATGTGTAGCATTCTATTACATGTGGAAAAAATCTGAACGTTATGATTTCTTTGCTCAG
      E  C  V  A  F  Y  Y  M  W  K  K  S  E  R  Y  D  F  F  A  Q   340
1089 CAAACACGATTTGGAAAGAAGAAATATAATCTTCATCCTGGTGTAACGGATTACATGGAT
      Q  T  R  F  G  K  K  Y  N  L  H  P  G  V  T  D  Y  M  D   360
1149 CGTCTTCTAGACGAAAGTGAAAGTGCTGCATCTAGTCGAGCACCATCCCCTCCCCCAACT
      R  L  L  D  E  S  E  S  A  A  S  S  R  A  P  S  P  P  P  T   380
1209 GCATCAAACAGTAGTAACAGCCAGTCTGAGAAAGAAGATGGCACTGTAAGCACTGCCAAT
      A  S  N  S  S  N  S  Q  S  E  K  E  D  G  T  V  S  T  A  N   400
1269 CAAAATGGAGTGTCATCTAATGGACCTAGCATACTCCAAATGCTTCTTCCAGTTCATTTT
      Q  N  G  V  S  S  N  G  P  S  I  L  Q  M  L  L  P  V  H  F   420
1329 TCAGCCATCAGTTCAAGAGCCAATGCCTTTTTAAAATAAAGCTTCTGTGGTCTTGTTTTT
      S  A  I  S  S  R  A  N  A  F  L  K  *   (SEQ ID NO:10)        432
1389 AATGGCTCAACTGTCTGATGTAATTGAGTGAAGGTTTGCACTGAGAAATTAGCATTCAGG
1449 CCTTACCCCCATGAAGTATTACTGTTAACATATGTTCGGACTGCTTCCCTTCACCAATGT
1509 GAACAACTTTTTTTCCCAAACAGTATTAAAAGCCACTTTGCAACACTTAAAAAAAAAAAA
1569 AAAAAA   (SEQ ID NO:9)
```

FIG. 22

```
Human    MAT-SVESSSPGGSATSDDHEFDPSADMLVHDFDDERTLEEEEMMEGETNFSSEIEDLAR
60
Xenopus  ••EP•LRTA•••••A••••••E••••••••E••••Q••••••••L•••V••T••••H•E•

Human    EGDMPIHELLSLYGYGSTVRLPEEDEEEEEGEEGEDDEDADNDDNSGCSGENKEENIKD
120
Xenopus  •SE•••D•••R••••••••P••G•ED••D-----------M•••C••••••••I•D•A•••

Human    SSGQEDETQSSNDDPSQSVASQDAQEIIRPRRCKYFDTNSEVEEESEEDEDYIPSEDWKK
180
Xenopus  •••••••••••••••TP•FTCR•VR•V••••••••••••H•I••••••••••V••••••

Human    EIMVGSMFQAEIPVGMCRYKENEKVYENSDQLLWDPEYLPEDKVIIFLKDASRRTGDEKG
240
Xenopus  •••••••••••••••I•K•••T•••••D••••••••••VM•ER••D••NE•••••CE•R•

Human    VEAIPEGSHIKDNEQALYELVKCNFDTEEALRKLRFNVKAAREELSVWTEEECRNFEQGL
300
Xenopus  LD••••••••••••••H•••••••••••R••••••••••••••••••••••••••••••

Human    KAYGKDFHLIQANKVRTRSVGECVAFYYMWKKSERYDFFAQQTRFGKKKYNLHPGVTDYM
360
Xenopus  ••••••••••••••••••••••••••••••••••••••••••••••••••••••••••••

Human    DRLLDESESAASSRAPSPPPTASNSSNSQSEKEDGTVSTANQNGVSSNGPSILQMLLPVH
420
Xenopus  ••••••••••T•••••••••T•••NT•••••••C•A•NNT•••••V•••CAITAYKDEA Human    FSAISSRANAFLK*  (SEQ ID NO:10)
432
Xenopus  KQGVHLNGPTISSDDPSSNETDTNGYNRENVTDDSRFSHTSGKTDTNPDDTNERPIKRQR Xenopus  MDSPGKESTGSSEFSQEVFSHGEV*  (SEQ ID NO:2)
```

|   | 1 | 2 | 3 | 4 | 5 | 6 | 7 | 8 |
|---|---|---|---|---|---|---|---|---|
| A | whole brain | amygdala | caudate nucleus | cerebellum | cerebral cortex | frontal lobe | hippocampus | medulla oblongata |
| B | occipital lobe | putamen | substantia nigra | temporal lobe | thalamus | sub-thal. nucleus | spinal cord | |
| C | heart | aorta | skeletal muscle | colon | bladder | uterus | prostate | stomach |
| D | testis | ovary | pancreas | pituitary | adrenal | thyroid | salivary | breast |
| E | kidney | liver | small intestine | spleen | thymus | leukocyte | lymph node | bone marrow |
| F | appendix | lung | trachea | placenta | | | | |
| G | fetal brain | fetal heart | fetal kidney | fetal liver | fetal spleen | fetal thymus | fetal lung | |
| H | yeast tot.RNA | yeast tRNA | E. coli rRNA | E. coli DNA | Poly r(A) | human Cot DNA | human DNA 100ng | human DNA 500ng |

FIG. 24A

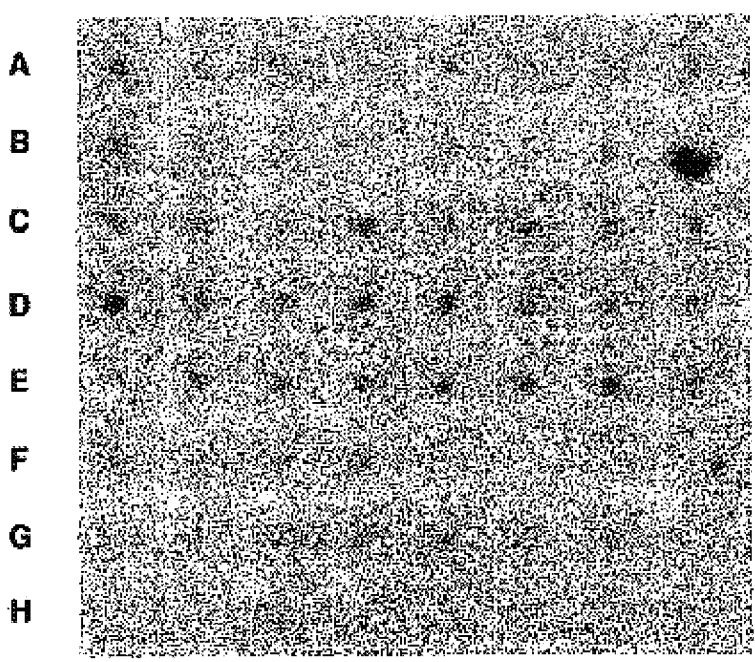

er1
14d exposure

FIG. 24B

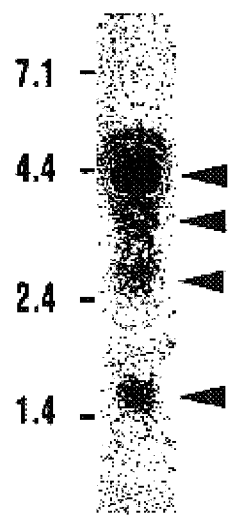
FIG. 31
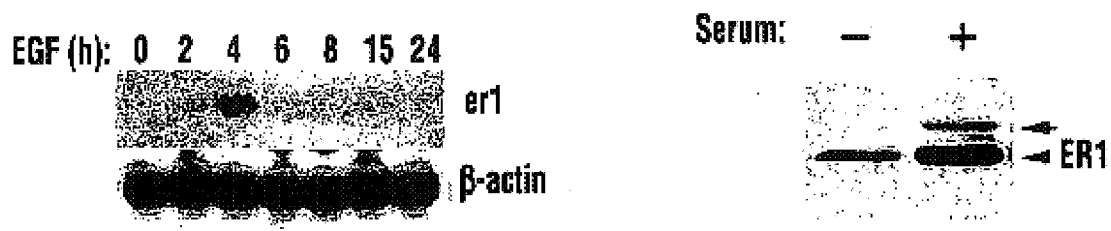
FIG. 32   FIG. 33

```
(SEQ ID NO:17)  CTCCCAGTGCCTGGCTGAGTTTCGGACGTGGTTAAG    Hum er1-MLP
                 | | |        | | | | |
(SEQ ID NO:18)          GGGTCGGACGCCAGCTGCGGACGCCAGC    Hum er1-MAT

AACCAACTGGTTGAGGTTCAATGCAGACAAGACGGATGTGATGCTGCCATCTGTTGAATCTTCAAGTCCAGGA    Hum er1-MLP
 | |   | | |    | | ||  ||||     ||| |  ||||||||||||||||||||||||||||||
TGCGGCCGCCGCGGAGATGTGAGGCGGCAGTACGGCAAATATGGCGACATCTGTTGAATCTTCAAGTCCAGGA    Hum er1-MAT
       |||||||  |||||||||||||||||||||| |   ||||||||||||||||||||||||||
(SEQ ID NO:19)   GATGTGACCCGGCAGTACGGCAAATATGGCGGCTCGTGTTGAATCTTCAAGTCCAGGA    Hum er1-MAA (SEQ ID NO:20)   M  L  P  S  V  E  -  -  -  -  -  -  -    Hum er1-MLP
(SEQ ID NO:21)   M  A  T  S  V  E  -  -  -  -  -  -  -    Hum er1-MAT
(SEQ ID NO:22)   M  A  A  R  V  E  -  -  -  -  -  -  -    Hum er1-MAA
```

FIG. 34

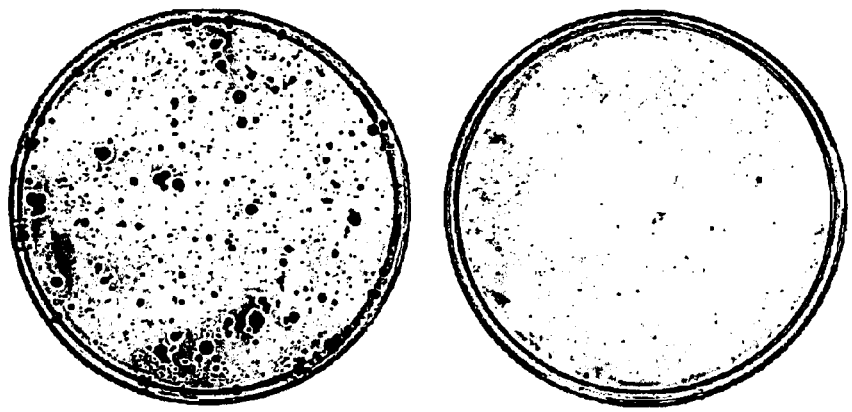
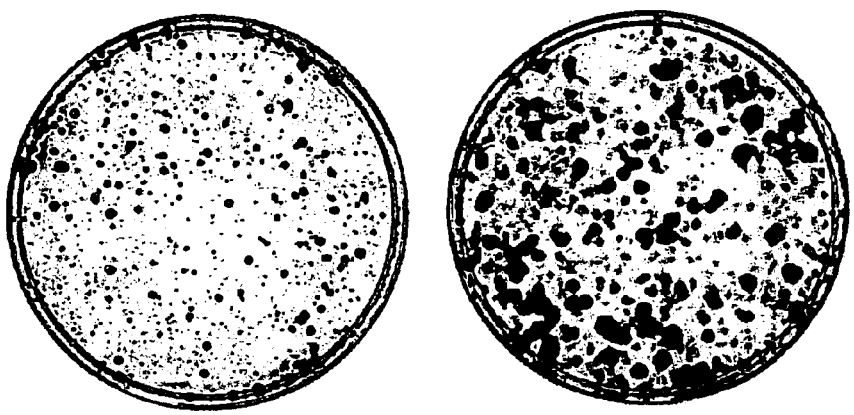
FIG. 40

Mouse partial cDNA sequence:
gagtacttaccagaagataaagtgattatatttcttaaagatgcatctagaagaacaggtgatga
gaagggtgtagaagcaattcctgaaggatctcacataaaagacaatgaacaggctttatatgaat
tggttaaatgcaattttgatacagaagaagcattgacaacattaagattaatgtaaaagcagct
agagaggaattatctgtttggacagaggaagagtgtagaaatttt gaacaagggctgaaggccta
tggaaaggatttt catttgactcaggctaataaagtccgaacaaggtcagttggtgaatgt gcag
cattctattacatgaaaaaaatctgaacgttatgatttcttt (SEQ ID NO:11)

Corresponding amino acid sequence:
EYLPEDKVIIFLKDASRRTGDEKGVEAIPEGSHIKDNEQALYELVKCNFDTEEALTTLRFNVKAA
REELSVWTEEECRNFEQGLKAYGKDFHLTQANKVRTRSVGECAAFYYMKKNLNVMIS
(SEQ ID NO:12)

FIG. 50

MAMMALIAN MESODERM INDUCTION EARLY RESPONSE (MIER) GENE FAMILY

FIELD OF THE INVENTION

The present invention relates to a novel family of immediate early response genes, the use of members of the family in diagnostic and therapeutic applications, in addition to drug design and vaccination protocols.

BACKGROUND OF THE INVENTION

Normal growth and differentiation of all organisms is dependent on cells responding correctly to a variety of internal and external signals. Many of these signals produce their effects by ultimately changing the transcription of specific genes. One of the major goals of developmental biologists is to define the interactions of gene products and the role they play in regulating cellular differentiation in time and space. Moreover, it is clear that inappropriate expression of many genes that control differentiation during embryonic development can lead to oncogenic transformation. Such genes include members of the growth factor families and components of their signal transduction pathways.

Polypeptide growth factors are members of a growing family of regulatory molecules that have been conserved throughout evolution and are known to have pleiotropic effects which range from stimulation of cell proliferation to control of cell differentiation. Growth factors have been linked to oncogenesis as many of the known oncogenes have been identified as overexpressed and/or mutated forms of growth factors, growth factor receptors or components of their intracellular signal transduction pathways. Oncogenes are thought to be altered such that their product escapes the normal control mechanism(s), resulting in the signalling pathways being permanently switched on. The overall result is uncontrolled cell growth.

The family of fibroblast growth factors (FGFs) consists of a number of members related by sequence and their ability to bind heparin (1). FGFs are involved in a number of cellular activities, including mitogenesis, cell differentiation and angiogenesis (reviewed in 2). In addition, overexpression of FGF in various cell lines leads to phenotypic transformation (3–5).

For example, fgf-3 was identified by its proximity to a preferred integration site of the proviral DNA of the murine mammary tumour virus (MMTV) in MMTV induced mammary carcinomas (Moore, et al., 1986), while fgf-4 was isolated from Kaposi's sarcoma by its ability to transform NIH 3T3 cells (Delli-Bovi and Basilico, 1987). Some members of the family were identified by their mitogenic activity such as fgf-2, which can cause phenotypic transformation when overexpressed in cultured cells (Sasada, et al., 1988; Neufeld, et al., 1988), thus classifying them as potential oncogenes.

Most of the studies to date have focused on FGF's mitogenic and transforming activities, however, FGF has also been shown to act as a differentiation factor for embryonic cells (Slack et al., 1987). For example, FGFs have been shown to induce mesoderm differentiation in Xenopus embryonic tissue (6) and many of the initial events in the cellular response during induction are similar to those previously characterized for the FGF-mediated mitogenic response. During mesoderm induction, FGF binds to high affinity cell surface receptors (7) which in turn become phosphorylated on tyrosine (8). The phosphorylated FGF receptor (FGFR) forms a signalling complex by binding a number of intracellular substrates (9) which results in activation of several well-characterized signalling pathways. For instance, protein kinase C becomes activated during FGF-induced mesoderm differentiation (8) as does MAPK (10).

Previously, growth and differentiation had been thought to be mutually exclusive, i.e. when a cell begins to differentiate, it stops dividing. Thus, the elucidation of the mechanisms that regulate the differentiation process may provide may provide valuable information about the molecular signals that are important for arresting cell growth. Further research in this field will contribute to an understanding of how growth factors, such as FGF function during early embryonic development to regulate patterning of mesodermal tissues and highlight differences in the cellular response during growth, differentiation and oncogenesis. It is therefore hoped that by elucidating the molecular mechanisms by which genes regulate developmental processes during embryogenesis, it may be possible to define how misregulation of these genes can lead to cancer.

Recent research has focused on finding means for triggering the immune system to attack cancerous cells, a tactic termed immunotherapy or vaccine therapy. Because immunity is a systemic reaction, it holds the potential to eliminate all cancer cells in a patient's body, even when they migrate away from the original tumor site or reappear after years of clinical remission. One challenge is that the immune system does not always recognize cancer cells and single them out for attack. A possible solution is to tag cancer cells with certain genes rendering them more visible to the immune system, which can then destroy them.

The immune response involves many different cells and chemicals that work together to destroy in several ways invading microbes or damaged cells. In general, abnormal cells sport surface proteins, called antigens, that differ from those found on healthy cells. When the immune system is activated, B lymphocytes produce antibodies which circulate through the body and bind to foreign antigens, thereby marking the antigen bearers for destruction by other components of the immune system. Other cells, T lymphocytes, recognize foreign antigens as well; they destroy cells displaying specific antigens of stimulate other killer T cells to do so. B and T cells communicate with one another by way of secreted proteins, cytokines. Other accessory cells, antigen-presenting cells and dendritic cells, further help T and B lymphocytes detect and respond to antigens on cancerous or infected cells.

One theory of a means of identifying cancer cells entails the abnormal expression of genes that are normally expressed only very early in development, such as during embryogenesis. If these types of genes are not expressed in normal, healthy adult cells, but are during cancerous growth, then proteins could be expressed that could function as an antigenic marker for immune attack.

Immunizing an organism with DNA coding for this antigen, could train or sensitize the immune system to attack cells expressing these antigens that are only expressed in during cancerous growth. Moreover, sensitive diagnostic means using either labelled polynucleotide probes or antibodies could be developed to detect the polynucleic acid messengers, such as mRNA, indicating the expression of these genes, hence the transformation into cancerous growth.

SUMMARY OF THE INVENTION

The subject invention concerns M-MIER gene family and its polynucleotide sequences which encode proteins; members of this gene family are activated in response to fibroblast growth factor (FGF) in an immediate early sequence. As an exemplary member of the M-MIER gene family, er1 is an early response gene that encodes a transcription factor found in the cell nucleus and is activated in response to FGF.

Embodiments of this invention pertaining to the M-MIER gene family comprise:
1) genomic sequences, gene sequences and partial sequences of the members of the mammalian M-MIER gene family;
2) isolated, synthetic M-MIER gene sequences;
3) polynucleotide sequence probes for diagnostic use;
4) polynucleotide sequences for antisense gene therapy;
5) polynucleotide sequences for DNA vaccines;
6) polynucleotide sequences for gene replacement therapy;
7) cloning vectors comprising mammalian M-MIER gene sequences;
8) antibodies to partial mammalian M-MIER gene sequences;
9) antibodies to peptides encoded by M-MIER gene sequences;
10) diagnostic kits comprising nucleic acid probes; and
11) diagnostic kits comprising antibodies to M-MIER proteins.

An object of the present invention is to provide a family of mammalian genes that are transcribed in the immediate early phase of mesoderm induction following exposure to FGF. In accordance with an aspect of the present invention there are provided cDNAs encoding members of this M-MIER gene family.

In accordance with another aspect of the invention there is provided a probe to identify and isolate similar gene sequences.

In accordance with yet a further aspect of the invention there is provided antisense nucleotides to block expression of gene products. In particular, the present invention provides synthetic oligonucleotides, designed to bind to the ER1 consensus DNA binding sequence, GTTTC/GG, that can be used to bind to mammalian DNA to inhibit er1.

In one embodiment of the subject invention, the proteins encoded by the genes described herein can be used to raise antibodies which in turn can be used in diagnostic or therapeutic applications.

In one aspect, the present invention provides a member of the M-MIER gene family: an isolated and purified ER1 polypeptide. Preferably, the polypeptide is a recombinant polypeptide, and more preferably comprises the amino acid sequence of FIG. 22.

In another aspect, the present invention provides an isolated and purified polynucleotide that encodes a M-MIER polypeptide. Preferably, the polynucleotide is a DNA molecule, such as an isolated and purified polynucleotide comprising the nucleotide base sequence for one member of the M-MIER family, ER1, shown in FIG. 22.

The present invention also contemplates an expression vector comprising a polynucleotide that encodes a M-MIER polypeptide. In a preferred embodiment, the polynucleotide is operatively linked to an enhancer-promoter.

Also contemplated is a recombinant cell transfected with a polynucleotide that encodes a M-MIER polypeptide. Preferably, the polynucleotide is under the transcriptional control of regulatory signals functional in the recombinant cell, and the regulatory signals appropriately control expression of the receptor polypeptide in a manner to enable all necessary transcriptional and post-transcriptional modification.

In yet another aspect, the present invention contemplates a process of preparing a M-MIER polypeptide, by producing a transformed recombinant cell, and maintaining the transformed recombinant cell under biological conditions suitable for the expression of the polypeptide.

The present invention also contemplates an antibody immunoreactive with a M-MIER polynucleotide and/or polypeptide. The antibody may be either monoclonal or polyclonal. Preferably, the antibody is a monoclonal antibody produced by recovering the polynucleotide and/or polypeptide from a cell host, expressing the polypeptides and then preparing antibody to the polypeptide in a suitable animal host.

In still another aspect, the present invention provides a process of detecting a M-MIER polynucleotide and/or polypeptide, which process comprises immunoreacting the polynucleotide and/or polypeptide with an antibody of the present invention and a diagnostic assay kit for detecting the presence of a M-MIER polynucleotide and/or polypeptide in a biological sample, the kit comprising a first container means comprising a first antibody that immunoreacts with the M-MIER polynucleotide and/or polypeptide. The first antibody is present in an amount sufficient to perform at least one assay.

Still further, the present invention provides a process of detecting a DNA molecule or RNA transcript that encodes a M-MIER polypeptide by hybridizing the DNA or RNA transcript with a polynucleotide that encodes the polypeptide to form a duplex, and then detecting the duplex.

Still further, the present invention provides a process of screening a substance for its ability to interact with members of the M-MIER family of proteins.

It is a further object of the present invention to provide a diagnostic marker for rapidly proliferating cells. A further aspect of the invention is concerned with a diagnostic kit containing antibodies to the nucleic acid of the invention. Yet a further aspect of the invention is concerned with a diagnostic kit containing antibodies to the protein encoded by the nucleic acid of the instant invention.

In still a further object of the present invention, a DNA binding domain of the protein product of M-MIER family of genes is provided, such as the SANT domain.

DESCRIPTION OF THE FIGURES

FIG. 1 presents a nucleotide (SEQ ID NO:1) and predicted amino acid sequence (SEQ ID NO:2) of one member of the nm-MIER family of genes, Xenopus er1. The nucleotide sequence numbers of the er1 cDNA are shown on the left and the amino acid sequence numbers of the predicted ER1 protein are shown on the right. The TAA termination codon is indicated by an asterisk. Four stretches of predominantly acidic residues are underlined, the proline-rich region is in bold and two putative nuclear localization signals (NLS) are indicated by double underlines; the second NLS conforms to the consensus for a bipartite NLS.

FIG. 2 shows the partial sequence of some members of the nm-MIER gene family, including nm-MIER S3 (SEQ ID NO:3), nm-MIER S14 (SEQ ID NO:4), nm-MIER S16 (SEQ ID NO:5), nm-MIER S17 ((SEQ ID NO:6), nm-MIER S24 (SEQ ID NO:7), and nm-MIER S30 ((SEQ ID NO:8).

FIG. 20 presents a mammalian partial nucleotide sequence for M-MIER er1 (SEQ ID NO:13). This is the putative sequence of the probe used to analyze M-MIER er1 expression in cancer cell lines. The corresponding amino acid sequence (SEQ ID NO:14) is also presented.

FIG. 22 presents nucleotide and predicted amino acid sequence of human er1. The nucleotide sequence numbers of the human er1 cDNA (SEQ ID NO:9) are shown on the left and the amino acid sequence numbers of the predicted human ER1 protein (SEQ ID NO:10) are shown on the right. The TAA termination codon is indicated by an asterisk. The SANT domain is underlined, the two predicted nuclear localization signals are indicated by double underlines and the proline-rich region is shown in bold.

FIG. 23 presents an amino acid comparison of the Xenopus and human ER1 proteins. Alignment was performed by the National Center for Biotechnology Information BLAST program. The full human ER1 amino acid sequence (SEQ ID NO:10) is shown in the one-letter code with the predicted NLS indicated by double underlines, the SANT domain by a single underline and the proline-rich SH3 region in bold. Amino acid sequence numbers are indicated on the right. For Xenopus ER1 (SEQ ID NO:2), only differences in the amino acid sequence are listed in the one-letter amino acid code; identities are indicated by a dot. Dashed indicate gaps introduced by the BLAST program.

FIG. 31 shows Northern blot analysis of human er1 mRNA expressed in the MDA-468 breast carcinoma cell line. These results are from a Northern analysis of poly A+ RNA from MDA-468, using an er1 cDNA probe. Four transcripts are indicated by arrows. mRNA was isolated from MDA-468 cell cultures and subjected to Northern blotting using cloned, radioactive er1 cDNA as a probe. The 4 detectable bands at the indicated molecular weights represent different versions of the er1 mRNA. In normal tissues we have only been able to detect extremely low levels of a single mRNA of 1.6 Kb in size which is equivalent to our cloned cDNA. These additional forms of er1 in tumours cells lines may represent alternative, mutated or tumour-specific forms of er1 mRNA which may contribute to the oncogenic phenotype and which may provide superior targets for therapeutic agents.

FIG. 32 Northern blot analysis of human er1 mRNA expressed in MDA-468 breast carcinoma cells at various times after exposure to epidermal growth factor (EGF). MDA-468 breast carcinoma cells were starved for 24 hours and then exposed to EGF. At the indicated times, mRNA was isolated from treated cells and equivalent amounts of mRNA were subjected to Northern blotting using cloned, radioactive er1 cDNA as a probe. Note the increase in the er1 mRNA levels after 4 hour exposure to EGF relative to the levels of the actin control mRNA. This data reveals that er1 is an early response gene to other growth stimuli and growth factors and therefore its expression in tumours may be a general feature of the growth of all tumours.

FIG. 33 demonstrates Western blot analysis of ER1 protein expressed in serum starved and serum-stimulated MDA-468 breast carcinoma cells, stained with anti-ER1. MDA-468 cells were starved for 24 hours before duplicated cultures were growth-stimulated with serum containing medium for 2 hours. Protein extracts were prepared from serum-stimulated (+) and serum-starved (−) cultures and equivalent amounts of protein were subjected to Western blotting using ER1 antibodies. Note the increase in the levels of the ER1 protein species. This data confirms that ER1protein levels also increase with exposure to other growth stimuli in breast cancer cells. In this case, the stimuli are physiological blood serum components.

FIG. 34 demonstrates a comparison of the nucleic acid and amino acid sequence around the start of translation of identified er1 variants. Included in the figure are the nucleic acid sequences around the translation start site for Hum er1-MLP (SEQ ID NO:17). Hum er1-MAT (SEQ ID NO:18), and Hum er1-MAA ((SEQ ID NO) genes, as well as the six N-terminal amino acids for Hum er1-MLP (SEQ ID NO:20). Hum er1-MAT (SEQ ID NO:21), and Hum er1-MAA ((SEQ ID NO:22) proteins. These variant cDNAs were identified from human cDNA libraries and our evidence suggests that they arise from alternatively spliced precursor mRNAs. The possibility exists that these variants are characteristic of the neoplastic stage and could be used as a more refined target for cancer cells. The underline indicates the er1 variant that is reported in Example IV. The existence of cellular variants of er1 RNA suggests that there may exist tumour-specific forms of er1 mRNA, as we observed in our Northern blot of breast carcinoma mRNA, and/or protein which could provide more specific targets for therapy.

FIG. 40 presents results demonstrating that antisense M-MIER er1 mRNA inhibits the growth of MDA-468 breast cancer cells. Cells transfected with the indicated constructs were selected for geneticin resistance. The identical number of MDA-468 cells or NIH 3T3 were transfected with equivalent concentrations of the indicated plasmids. These plasmid constructs control the expression of er1 mRNA (sense), er1 antisense RNA (Antisense ) or mRNA green fluorescent protein (GFP) which serves as a control for transfection efficiency. The cultures were exposed to the antibiotic Geneticin which kills cell which have not taken up and expressed these plasmids and cell colonies are allowed to grow. Note that antisense M-MIER er1 RNA, which blocks the normally high levels of ER1 in MDA-468 cells, inhibits the growth and recovery of these cancer cells. The recovery and growth of NIH 3T3 fibroblast cells, which represent normal cells, is not affected. This data which provides unequivocal support for the effectiveness and utility of one embodiment of the invention, the use of antisense er1 as a treatment for cancer. It demonstrates that antisense er1 RNA can completely block the growth of breast cancer cells, which express high levels of ER1, but does not affect the growth of normal NIH 3T3 fibroblast cells which do not express detectable levels of ER1.

FIG. 50 presents the partial sequence of mouse er1 cDNA nucleic acid sequence (SEQ ID NO:11) with corresponding amino acid sequence (SEQ ID NO:12).

DETAILED DESCRIPTION OF THE INVENTION

Figure 3:
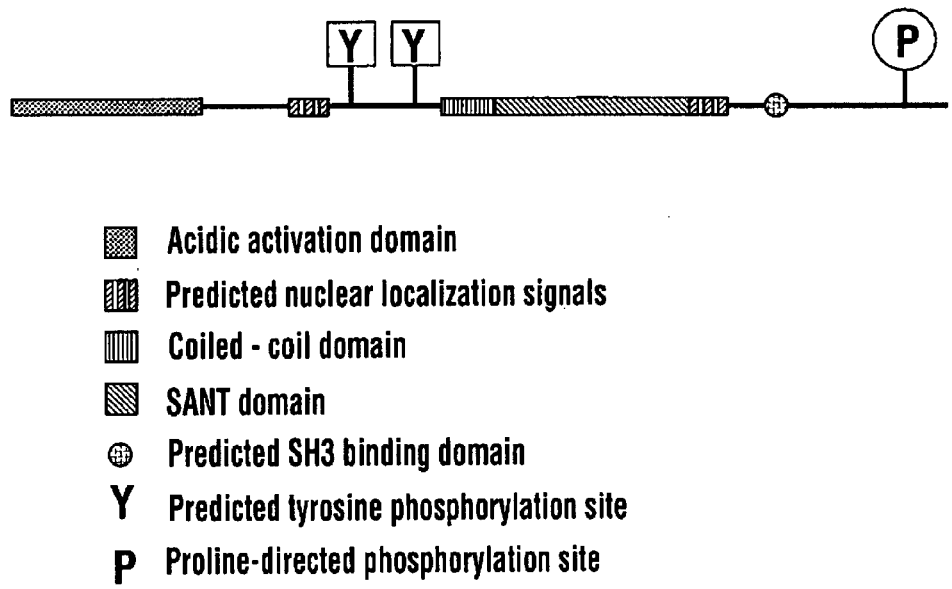
FIG. 3 is a schematic drawing indicating the different functional and regulatory domains of ER1. The identification and boundaries of these regions were determined by experimentation, or by recognizing the conservation of amino acid sequences between proteins which define a particular function using one member of the nm-MIER family, Xenopus. This information of the functional domains of er1 allows for identification of important regions for the development of superior vaccines with the minimum of cross reactivity to other important proteins and to design drugs which could interfere with specific biochemical functions. Also, other uses of this SANT domain include its use to affinity-purify the DNA sequence to which ER1 binds. This is also used to isolate all the genes that MIER er1 regulates. The ER1 consensus DNA binding sequence is predicted to be: GTTTC/GG.
Figure 4A:
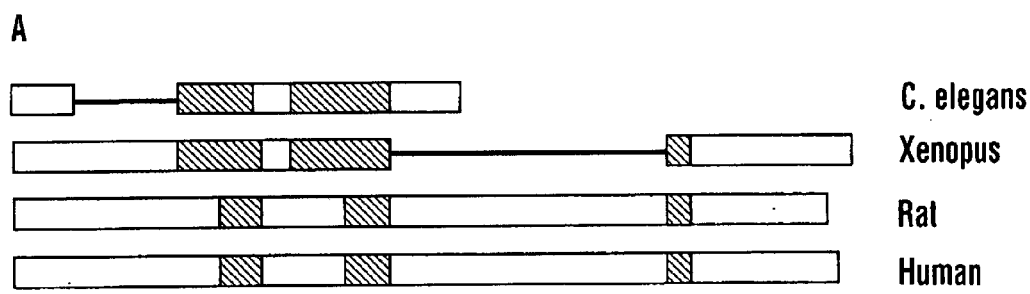
FIG. 4 presents an amino acid comparison of one member of the nm-MIER proteins, Xenopus ER1 (SEQ ID NO:1) to the rat and human MTA1 and the *C. elegans* similar-to-MTA1 protein. A, Schematic illustrating alignment of the predicted Xenopus ER1 protein sequence (SEQ ID NO:1) with the rat and human MTA1 and the similar-to-MTA1 protein from *C. elgans*. The N-termini were aligned and gaps (black lines) were introduced in the *C. elegans* and Xenopus proteins in order to align the regions of similarity (hatched) identified by the BLAST program. White boxes indicate unique regions. B, Alignment of the predicted-ER1 amino acid sequence with the MTA1 amino acid sequences in the regions of similarity illustrated in A. Identities are indicated by the one-letter amino acid code, conservative changes are indicate by a plus sign (+) and dashes (−) indicated non-conservative changes. The amino acid sequence numbers of the ER1 protein are shown on the right.
Figure 5:
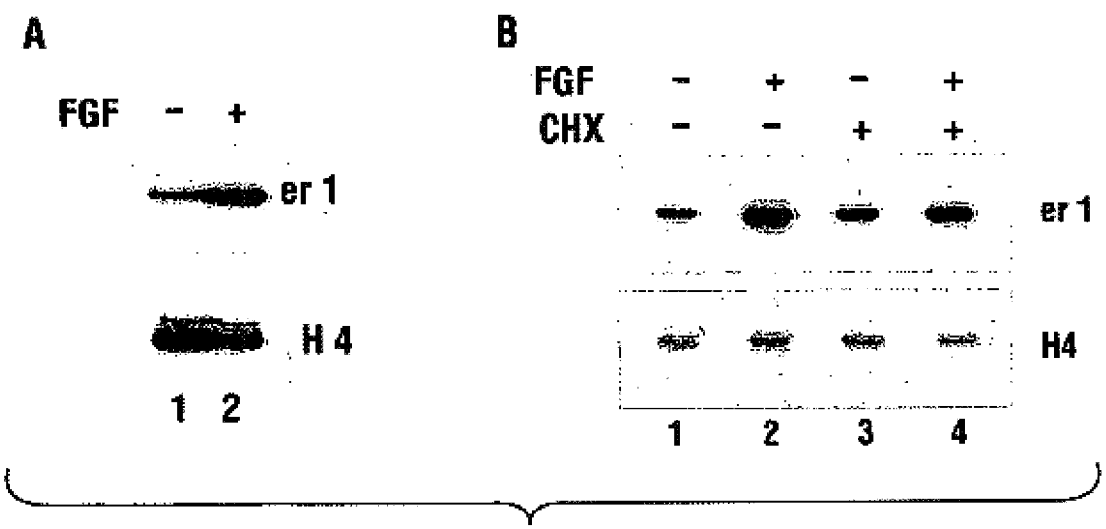
FIG. 5 demonstrates that Xenopus er1, a member of the nm-MIER family of genes is an FGF immediate-early response gene. A, FGF-stimulated increase in steady-state levels of Xenopus er1. Explants (5 per sample) from stage 8 Xenopus blastulae were treated for 30 min in the presence (lane 2) or absence (lane 1) of 100 ng/ml XbFGF. Total RNA was extracted and RT-PCR analysis was performed as described under Example IV. B, FGF-stimulated increase of er1 in the absence of protein synthesis. Explants were pre-incubated for 30 min with (lanes 3, 4) or without (lanes 1, 2) 5 ug/ml cycloheximide; 100 ng/ml XbFGF was added to the samples in lanes 2 and 4 and all samples were incubated for an additional 30 min. Extraction and analysis were performed as described in A.
Figure 6:
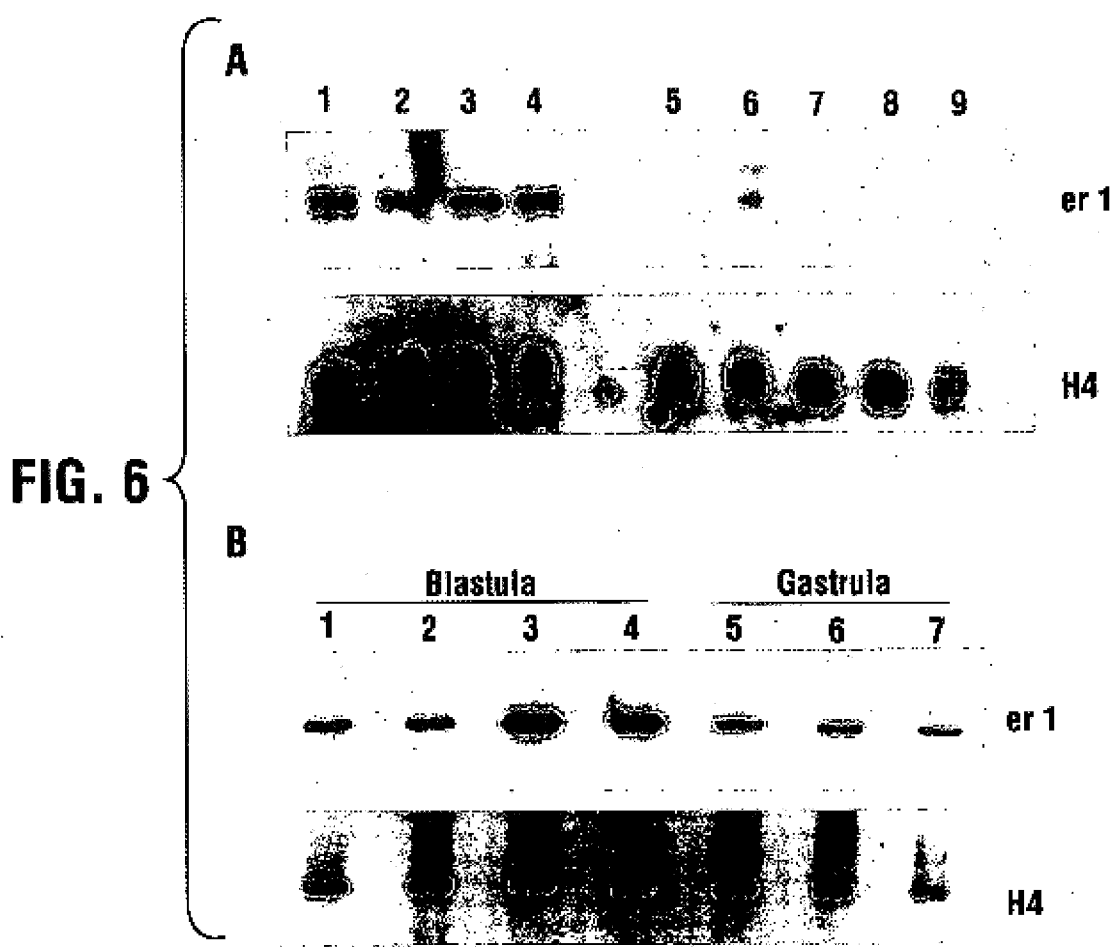
FIG. 6 demonstrates that expression of er1 is restricted to early developmental stages in Xenopus, one exemplary member of the nm-MIER family of genes. A, Northern blot analysis of Xenopus er1 expression. Total RNA was isolated from the following developmental stages: stage 2 (2-cell; lane 1), stage 6 (64-cell; lane 2), stage 7 (early blastula; lane 3), stage 8 (mid-blastula; lane 4), stage 12 (mid-gastrula; lane 5), stage 17 (neurula; lane 6), stage 22 (tailbud; lane 7), stage 30 (lane 8) and stage 41 (tadpole; lane 9). Northern analysis was performed as in Sambrook et al. (20) using $^{32}$P-labeled 2.3-kb er1 cDNA as a probe. The blot was stripped and re-probed with $^{32}$P-labeled histone H4 cDNA. B, Quantitative PCR analysis of er1 levels during blastula and gastrula stages of development. Total RNA was isolated at 1 h intervals during blastula stages, beginning at stage 7 (lane 1) and ending with stage 9 (lane 4). For gastrula stages in lanes 5–7, RNA was isolated at stages 10, 10.5 and 12, respectively, according to morphological criteria (29). RT-PCR and analysis were performed as described in the legend to Example IV.
Figure 7:
FIG. 7 demonstrates the nuclear localization of one member of the nm-MIER proteins, Xenopus ER1. A, Immunoprecipitation of in vitro translation products with anti-ER1. Rabbit reticulocyte lysates programmed with er1 cDNA in pcDNA3 were immunoprecipitated with either pre-immune (lane 2) or anti-ER1 (lane 3) serum prepared in our laboratory. Total translation products representing one half of the input into each immunopreciptation are shown in lane 1. B, ER1 is localized within the nucleus in transfected NIH 3T3 cells. NIH 3T3 cells were transfected with either the pcDNA3 vector alone (top) or er1-pcDNA3 (bottom). After 48 h, cells were fixed and stained with anti-ER1, as described in Example IV.

The invention relates to a family of mammalian genes that are transcribed in the immediate early phase following exposure to FGF during mesoderm induction, termed Mesoderm Induction Early Response (M-MIER) genes. Defining features of the members of this family include that these genes are a) transcribed in response to FGF; b) are expressed within 40 minutes of FGF treatment; and c) do not require protein synthesis for transcription. There are at least eleven members within this family.

The unique polynucleotide sequences of the subject invention include M-MIER gene sequences which encode the M-MIER proteins, as well as sequences which drive the expression of these proteins.

As an exemplary member of the M-MIER gene family, er1 is an early response gene that encodes a transcription factor found in the cell nucleus and is activated in response to FGF. The gene is overexpressed in breast carcinoma and cervical carcinoma cell lines and possibly in general in all cancer cell lines. Er1 is also overexpressed in an abnormal T-cell subset (CD28-) whose numbers increase with disease progression in AIDS patients. This CD28-subset also increases in chronic inflammatory disorders. Therefore this gene and its product are potential targets for diagnosis and treatment of various cancers as well as immune disorders such as AIDS.

The ultimate targets of these signal transduction pathways are the immediate-early genes. To date, very few FGF immediate-early genes have been identified (11, 12). Accordingly, we have utilized the differential display methodology (13) to isolate cDNAs representing such genes

Definitions and Abbreviations

The term "M-MIER" refers to Mammalian Mesoderm Induction Immediate Early Response genes, their nucleic acid transcription products and translated protein products. Defining features of the members of this family include that the genes are a) transcribed in response to fibroblast growth factors (FGF); b) are expressed within 40 minutes of FGF treatment; and c) do not require protein synthesis for transcription. There are at least eleven members within this family; one member is er1.

The M-MIER genes and polypeptides of the present invention are not limited to a particular mammalian source. As disclosed herein, the techniques and compositions of the present invention provide, for example, the identification and isolation of sources from mammalian cancerous cell lines. Thus, the invention provides for the general detection and isolation of the genus of M-MIER genes and polypeptides from a variety of sources such as human and more. It is believed that a number of species of the family of M-MIER genes and polypeptides are amenable to detection and isolation using the compositions and methods of the present invention.

Polynucleotides and polypeptides of the present invention are prepared by standard techniques well known to those skilled in the art. Such techniques include, but are not limited to, isolation and purification from tissues known to contain these genes and polypeptides, and expression from cloned DNA that encodes such polypeptides using transformed cells.

The family of M-MIER genes can be easily generated, without undue experimentation from the nm-MIER genes and fragments of such sequences. The technology of cross-species cloning is based on the principle that most genes contain at least one region, usually a functional domain, that is highly conserved from lower eukaryotes to humans. The higher the degree of conservation, it is generally hypothersized, the more important the conserved function (Zorn, A. M., et al., (1997) *Gene* 188:199–206). As a result, sequences from regions of conserved DNA are routinely used to clone the homologues of genes from one species to another using technologies and standard procedures which can be performed by one skilled in the art without any innovation.

Generally, the practice of one skilled in the art is to identify and characterize genes from lower species and use sequences from those genes to identify and characterize higher mammalian and human homologues. While invertebrate species such as the fruit fly (*Drosophila melanogaster*) or yeast may serve as the starting point for cloning human gene homologues (Ingham, P. W., (1998) *Curr. Opin. Genet. Dev.* 8:88–94; Scott, M. P., (1997) *Nat. Genet.* 15:117–118;

Miyake, S., et al., (1996) *Gene* 175:71–75), a common approach is to clone mammalian including human homologues using sequences isolated from the vertebrate Xenopus. This system has been used to identify and characterize mammalian counterparts to the Xenopus neutrophin-4 gene (Ip, N.Y., et al., (1992) *Proc. Natl. Acad. Sci. USA* 89:3060–3064), the gene encoding a Xenopus quaking, KH domain RNA-binding protein (Zorn, A. M., et al., (1997) *Gene* 188:199–206), the *Xenopus laevis* vitellogenin mRNA binding protein gene (Dodson, R. E., et al., (1995) 52:505–15). Similarly, numerous genes including human genes, exhibiting the zinc finger motif, a highly conserved tandemly repeated sequence of 28 to 30 amino acids, have been characterized based on this motif's initial characterization in the gene encoding transcription factor TFIIIA from *Xenopus laevis* (Constantinou-Deltas, C. D., et al., (1992) *Genomics* 12:581–589). The same approach and technology is equally well adapted and established in the art to enable the cloning of cross-species gene homologues from man to lower order species such as was done for the identification and characterization of a Xenopus CD3 homologue (Dzjalo, R. C. and Cooper, M. D. (1997) *Eur. J. Immunol.* 27:1640–1647.

Polymerase chain reaction (PCR) technology has made it possible to produce enough cDNA for cloning, even at reduced stringency and for rare transcripts. This was not always possible with the previous technology of screening a library, particularly if the gene of interest was represented at low copy number, as is the case for most regulatory genes. The methodology for screening a library using the "old" method involves using the cDNA or genomic clone of the gene of interest of one species (e.g. Xenopus) to probe a genomic or cDNA library of a second species (e.g. human) at reduced stringency. This allows the probe to bind to its related target despite less potential hydrogen bonding due to mismatches of nucleotide complementary pairs.

Today the most popular method is to utilize oligonucleotide primers which can be designed from the sequence of a cloned Xenopus gene and then employed using PCR to amplify a portion of the human homologue either from genomic DNA, cDNA generated from mRNA isolated from human cells (reverse transcriptase PCR=RT-PCR) or directly from a cDNA library made from RNA isolated from human cells. PCR primers designed on the basis of a cloned and sequenced Xenopus gene can be varied according to their size, complexity, position within the gene and degeneracy, in order to isolate the human homologue. The PCR product can be cloned directly, sequenced and compared to its Xenopus homologue to verify its identity or similarity. The cloned human DNA can then be used as a probe to isolate the entire or complete cDNA or gene from the appropriate library. The overall procedure does not involve innovation since all of the technology involved requires either following manufacturers' instructions in commercial kits (e.g. PCR, cloning, sequencing and libraries), automation (e.g. sequencing and reading the sequence) or in the case of designing the primers for PCR, the use of software programs and the availability of commercial synthesis.

Therefore, the cloning of mammalian, including the human homologues of the Xenopus MIER gene family falls properly within the scope of the present invention.

The family of genes has utility as a collection of individual members.

The Utility of the MIER Gene Family

Further to the utility of the individual MIER genes, it is also well known in the art that many gene products often are only fully functional when associated as a complex. Various transcription factors are examples of this phenomenon. With this in mind, it is reasonable to conclude that the products from the MIER gene family may function in a similar fashion, therefore, more than one gene of this family may be optimal to maximize its use in diagnosing or treating a type of cancer.

For example, a useful embodiment for the entire MIER gene family is to create transcription profiles for one or more selected members as a means of monitoring the progression of cancer in eukaryotic cells. Although typically found in embryonic cells, the expression of one or more MIER genes in normal adult cells have been linked to the onset of cancer. In addition to this, the number of genetic mutations tend to vary with the form and severity of the cancer. Therefore, expression profiles of one or more selected members of the MIER gene family would be useful, especially when the profiles are correlated to the different forms of cancer, thus allowing for early and precise diagnosis and the proper treatment.

Early detection is commonly cited as being essential in ensuring a favourable prognosis to cancer. In the case of the MIER gene family, evidence of their expression in normal adult cells is linked to the development of many forms of cancer. Therefore, the availability of an expression profile for one or more selected members of the MIER gene family may help to ensure the early and proper diagnosis of the various forms of cancer. This in turn will improve the treatment of the cancerous growth since a treatment may now be tailored to the individual according to the type of cancer and its stage of development. This method would minimize the occurrences of severe side-effects by eliminating overly aggressive treatments when it is not necessary.

In one embodiment of the invention, the biological activity of the M-MIER proteins of the subject invention can be reduced or eliminated by administering an effective amount of an antibody to each of the M-MIER proteins. Alternatively, the activity of the M-MIER proteins can be controlled by modulation of expression of the M-MIER protein. This can be accomplished by, for example, the administration of antisense DNA.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. Allelic variations of the exemplified sequences also come within the scope of the subject invention. The polynucleotide sequences falling within the scope of the subject invention further include sequences which specifically hybridize with the exemplified sequences under stringent conditions. The nucleic acid includes both the sense and antisense strands as either individual strands or in the duplex.

The terms "hybridize" or "hybridizing" refer to the binding of two single-stranded nucleic acids via complementary base pairing.

The phrase "hybridizing specifically to" refers to binding, duplexing, or hybridizing of a molecule to a nucleotide sequence under stringent conditions when that sequence is present in a preparation of total cellular DNA or RNA.

The term "stringent conditions" refers to conditions under which a probe will hybridize to its target sub-sequence, but not to sequences having little or no homology to the target sequence. Generally, stringent conditions are selected to be about 5.degree. C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.1 to 1.0N Na ion concentration at a pH of about 7.0 to 7.5 and the temperature is at least about 60. degree. C. for long sequences (e.g., greater than about 50 nucleotides) and at least about 42. degree. C. for shorter sequences (e.g., about 10 to 50 nucleotides).

The terms "isolated" or "substantially pure" when referring to polynucleotide sequences encoding the M-MIER proteins or fragments thereof refers to nucleic acids which encode M-MIER proteins or peptides and which are no longer in the presence of sequences with which they are associated in nature.

The terms "isolated" or "substantially purified" when referring to the proteins of the subject invention means a chemical composition which is essentially free of other cellular components. It is preferably in a homogenous state and can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably, the protein is purified to greater than 95%, and most preferably the protein is purified to essential homogeneity, wherein other macromolecular species are not detected by conventional techniques.

The phrase "specifically binds to an antibody" or "specifically immunoreactive with," when referring to a protein or peptide, refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample.

Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein. See Harlow and Lan (1988) for a description of immunoassay formats and conditions that could be used to determine specific immunoreactivity. The subject invention further concerns antibodies raised against the purified M-MIER molecules or their fragments.

The term "biological sample" as used herein refers to any sample obtained from a living organism or from an organism that has died. Examples of biological samples include body fluids, tissue specimens, and tissue cultures lines taken from patients.

The term "recombinant DNA" or "recombinantly-produced DNA" refers to DNA which has been isolated from its native or endogenous source and modified either chemically or enzymatically to delete naturally-occurring flanking nucleotides or provide flanking nucleotides that do not naturally occur.

Flanking nucleotides are those nucleotides which are either upstream or downstream from the described sequence or sub-sequence of nucleotides.

The term "recombinant protein" or "recombinantly-produced protein" refers to a peptide or protein produced using cells that do not have an endogenous copy of DNA able to express the protein. The cells produce the protein because they have been genetically altered by the introduction of an appropriate nucleic acid sequence. The recombinant protein will not be found in association with proteins and other subcellular components normally associated with the cells producing the protein.

It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

As those of ordinary skill in the art will appreciate, any of a number of different nucleotide sequences can be used, based on the degeneracy of the genetic code, to produce the M-MIER proteins described herein. Accordingly, any nucleotide sequence which encodes the M-MIER proteins described herein comes within the scope of this invention and the claims appended hereto. Also, as described herein, fragments of the M-MIER proteins are an aspect of the subject invention so long as such fragments retain the biological activity so that such fragments are useful in therapeutic and/or diagnostic procedures as described herein. Such fragments can easily and routinely be produced by techniques well known in the art. For example, time-controlled Bal31 exonuclease digestion of the full-length DNA followed by expression of the resulting fragments and routine screening can be used to readily identify expression products having the desired activity.

Polynucleotide Probes

In addition, PCR-amplified DNA may serve as a hybridization probe. In order to analyze DNA using the nucleotide sequences of the subject invention as probes, the DNA can first be obtained in its native, double-stranded form. A number of procedures are currently used to isolate DNA and are well known to those skilled in this art.

One approach for the use of the subject invention as probes entails first identifying by Southern blot analysis of a DNA library all DNA segments homologous with the disclosed nucleotide sequences. Thus, it is possible, without the aid of biological analysis, to know in advance the presence of genes homologous with the polynucleotide sequences described herein. Such a probe analysis provides a rapid diagnostic method.

One hybridization procedure useful according to the subject invention typically includes the initial steps of isolating the DNA sample of interest and purifying it chemically. For example, total fractionated nucleic acid isolated from a biological sample can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane in a manner that retains the geometry of the pieces. The membrane can then be dried and prehybridized to equilibrate it for later immersion in a hybridization solution. The manner in which the nucleic acid is affixed to a solid support may vary. This fixing of the DNA for later processing has great value for the use of this technique in field studies, remote from laboratory facilities.

The particular hybridization technique is not essential to the subject invention. As improvements are made in hybridization techniques, they can be readily applied.

As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

The nucleotide segments of the subject invention which are used as probes can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include .sup.32 P, .sup.35 S, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. For synthetic probes, it may be most desirable to use enzymes such as polynucleotide kinase or terminal transferase to end-label the DNA for use as probes.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO93/16094. The probe may also be labeled at both ends with different types of labels for ease of separation, as, for example, by using an isotopic label at the end mentioned above and a biotin label at the other end.

The amount of labeled probe which is present in the hybridization solution will vary widely, depending upon the nature of the label, the amount of the labeled probe which can reasonably bind to the filter, and the stringency of the hybridization. Generally, substantial excesses of the probe will be employed to enhance the rate of binding of the probe to the fixed DNA.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under stringent conditions by techniques well known in the art, as described, for example, in Keller and Manak, 1987.

Duplex formation and stability depend on substantial complementarity between the two strands of a hybrid, and, as noted above, a certain degree of mismatch can be tolerated. Therefore, the nucleotide sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:
(1) synthesizing chemically or otherwise an artificial sequence which is a mutation, insertion or deletion of the known sequence;
(2) using a nucleotide sequence of the present invention as a probe to obtain via hybridization a new sequence or a mutation, insertion or deletion of the probe sequence; and
(3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed nucleotide sequences can be readily prepared by methods which are well known to those skilled in the art. These variants can be used in the same manner as the instant probe sequences so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid.

The amino acid sequence of the proteins of the subject invention can be encoded by equivalent nucleotide sequences encoding the same amino acid sequence of the protein. Accordingly, the subject invention includes probes which would hybridize with various polynucleotide sequences which would all code for a given protein or variations of a given protein. In addition, it has been shown that proteins of identified structure and function may be constructed by changing the amino acid sequence if such changes do not alter the protein secondary structure (Kaiser and Kezdy, 1984).

In one aspect, the present invention provides an isolated and purified polynucleotide that encodes a M-MIER polypeptide. In a preferred embodiment, a polynucleotide of the present invention is a DNA molecule. Even more preferably, a polynucleotide of the present invention encodes a polypeptide comprising the amino acid residue sequence of ER1, a member of the M-MIER family (FIG. 22). Most preferably, an isolated and purified polynucleotide of the invention comprises the nucleotide base sequence of FIG. 22.

As used herein, the term "polynucleotide" means a sequence of nucleotides connected by phosphodiester linkages. Polynucleotides are presented herein in a 5' to 3' direction. A polynucleotide of the present invention may comprise about several thousand base pairs. Preferably, a polynucleotide comprises from about 100 to about 10,000 base pairs. Preferred lengths of particular polynucleotides are set forth hereinafter.

A polynucleotide of the present invention may be a deoxyribonucleic acid (DNA) molecule or ribonucleic acid (RNA) molecule. Where a polynucleotide is a DNA molecule, that molecule may be a gene or a cDNA molecule. Nucleotide bases are indicated herein by a single letter code: adenine (A), guanine (G), thymine (T) and cytosine (C).

A polynucleotide of the present invention may be prepared using standard techniques well-known to one of skill in the art. The preparation of a cDNA molecule encoding an er1 polypeptide of the present invention is described hereinafter in the examples. A polynucleotide may also be prepared from genomic DNA libraries using, for example, lambda phage technologies.

In another aspect, the present invention provides an isolated and purified polynucleotide that encodes a M-MIER polypeptide, where the polynucleotide is preparable by a process comprising the steps of constructing a library of cDNA clones from a cell that expresses the polypeptide; screening the library with a labelled cDNA probe prepared from RNA that encodes the polypeptide; and selecting a clone that hybridizes to the probe.

A further aspect of the claimed invention are antibodies that are raised by immunization of an animal with a purified protein or polynucleotides of the subject invention. Both polyclonal and monoclonal antibodies can be produced using standard procedures well known to those skilled in the art using the proteins of the subject invention as an immunogen (see, for example, Monoclonal Antibodies: Principles and Practice, 1983; Monoclonal Hybridoma Antibodies: Techniques and Applications, 1982; Selected Methods in Cellular Immunology, 1980; Immunological Methods, Vol. II, 1981; Practical Immunology, and Kohler et al., 1975).

The proteins of the subject invention include those which are specifically exemplified herein as well as related proteins which, for example, are immunoreactive with antibodies which are produced by, or are immunologically reactive with, the proteins specifically exemplified herein.

The proteins described herein can be used in therapeutic or diagnostic procedures.

Probes

In another aspect, DNA sequence information provided by the present invention allows for the preparation of relatively short DNA (or RNA) sequences having the ability to specifically hybridize to gene sequences of the selected polynucleotide disclosed herein. In these aspects, nucleic acid probes of an appropriate length are prepared based on a consideration of a selected nucleotide sequence, e.g., a sequence such as that shown in FIG. 22. The ability of such nucleic acid probes to specifically hybridize to a polynucleotide encoding a M-MIER lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes a M-MIER polypeptide from mammalian or non-mammalian cells using PCR technology.

To provide certain of the advantages in accordance with the present invention, a preferred nucleic acid sequence employed for hybridization studies or assays includes probe molecules that are complementary to at least an about (14) to an about (70), nucleotide long stretch of a polynucleotide that encodes a M-MIER polypeptide, such as the nucleotide base sequences shown in FIG. 22. A size of at least 14 nucleotides in length helps to ensure that the fragment is of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained, one will generally prefer to design nucleic acid molecules having gene-complementary stretches of 25 to 40 nucleotides, 55 to 70 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 14 contiguous bases of FIG. 22, wherein the polynucleotide hybridizes to a polynucleotide that encodes a M-MIER polypeptide. Preferably, the isolated and purified polynucleotide comprises a base sequence that is identical or complementary to a segment of at least 25 to 70 contiguous bases of FIG. 22. For example, the polynucleotide of the invention may comprise a segment of bases identical or complementary to 40 or 55 contiguous bases of the disclosed nucleotide sequences.

Accordingly, a polynucleotide probe molecule of the invention may be used for its ability to selectively form duplex molecules with complementary stretches of the gene.

Depending on the application envisioned, one employs varying conditions of hybridization to achieve varying degree of selectivity of the probe toward the target sequence. For applications requiring a high degree of selectivity, one typically employs relatively stringent conditions to form the hybrids. For example, one selects relatively low salt and/or high temperature conditions, such as provided by about 0.02M to about 0.15M NaCl at temperatures of about 50° C. to about 70° C. Those conditions are particularly selective, and tolerate little, if any, mismatch between the probe and the template or target strand.

In some applications where it is the intention to prepare mutants employing a mutant primer strand hybridized to an underlying template or where one seeks to isolate a M-MIER polypeptide coding sequence from other cells, functional equivalents, or the like, less stringent hybridization conditions are typically needed to allow formation of the heteroduplex. In these circumstances, one employs conditions such as about 0.15M to about 0.9M salt, at temperatures ranging from about 20° C. to about 55° C. Cross-hybridizing species may thereby be readily identified as positively hybridizing signals with respect to control hybridizations. In any case, it is generally appreciated that conditions may be rendered more stringent by the addition of increasing amounts of formamide, which serves to destabilize the hybrid duplex in the same manner as increased temperature. Thus, hybridization conditions may be readily manipulated, and thus will generally be a method of choice depending on the desired results.

In still another embodiment of the present invention, there is provided a isolated and purified polynucleotide comprising a base sequence that is identical or complementary to a segment of at least about 14 contiguous bases of M-MIER The polynucleotide of the invention hybridizes to M-MIER or a complement of M-MIER. Preferably, the isolated and purified polynucleotide comprises a base sequence that is identical or complementary to a segment of at least 25 to 70 contiguous bases of M-MIER For example, the polynucleotide of the invention may comprise a segment of bases identical or complementary to 40 or 55 contiguous bases of M-MIER.

Alternatively, the present invention contemplates an isolated and purified polynucleotide that comprises a base sequence that is identical or complementary to a segment of at least about 14 contiguous bases of M-MIER.

The polynucleotide of the invention hybridizes to M-MIER, or a complement of M-MIER. Preferably, the polynucleotide comprises a base sequence that is identical or complementary to a segment of at least 25 to 70 contiguous bases of M-MIER. For example, the polynucleotide may comprise a segment of bases identical or complementary to 40 or 55 contiguous bases of M-MIER.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as welt as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions will depend on the particular circumstances and criteria required (e.g., the G+C content, type of target nucleic acid, source of nucleic acid, size of hybridization probe, etc.). Following washing of the matrix to remove nonspecifically bound probe molecules, specific hybridization is detected, or even quantified, by means of the label.

Polynucleotide Primers

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan. It is important to note that the mutational, insertional, and deletional variants generated from a given primer sequence may be more or less efficient than the original sequences. Notwithstanding such differences in efficiency, these variants are within the scope of the present invention.

DNA Vaccines and Immunotherapy

Tumor Associated Antigens

Figure 46:
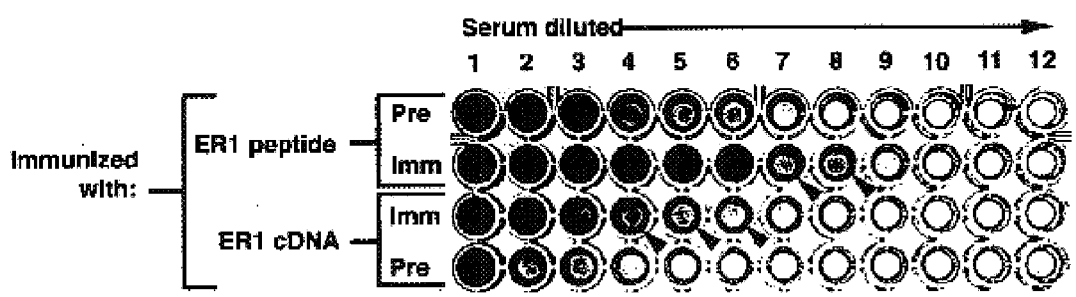
FIG. 46 demonstrates stimulation of an immune response with ER1 peptides or er1 DNA. Rabbits were immunized with an ER1 peptide conjugated to keyhole limpet hemocyanin or er1 cDNA in a mammalian expression vector. Antiserum and pre-immune serum from the same rabbits were titrated in a twofold serial dilution (columns 1–12) and tested in a standard ELISA assay using full-length ER1 protein as the antigen. Positives appear as grey/black and the pre-immmune serves to indicate the background level of the assay. Positive reactions in the immune serum at higher dilutions than the pre-immune (arrows) demonstrates the presence of anti-ER1 antibodies. The results of these studies provides evidence that the DNA based ER1 constructs can be injected into animals and taken up by animal cells. The plasmids can direct the synthesis of ER1 protein and this protein can elicit an immune response in the animal to generate and anti-ER1 antibodies. These results provide evidence that DNA based constructs can be used as a vaccine against ER1 protein. Well established principles of immunology extend these findings to indicate that such an antibody response means that immune system will react to cells expressing ER1. In this application of the present invention, the only cells expressing ER1would be the cancer cells.
Figures 48, 49:
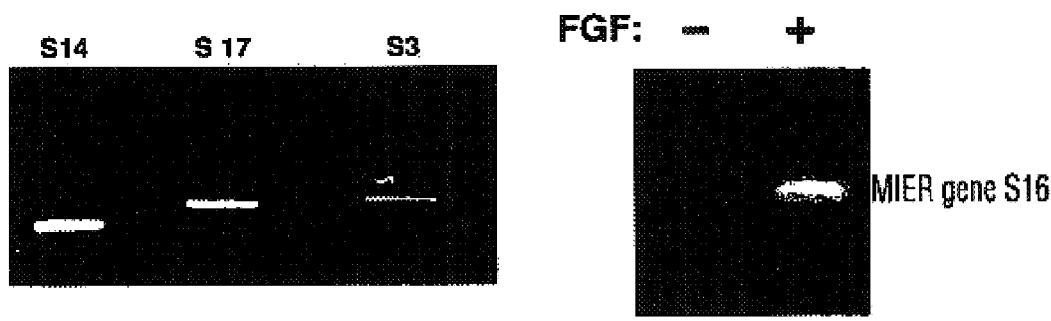
FIG. 48 demonstrates that nm-MIER gene S16 is upregulatd by FGF. Xenopus embryo explants were incubated in the absence (−) or presence (+) of FGF for 30 min. RNA was extracted, reverse-transcribed and subjected to PCR using primers for the nm-MIER gene S16. These results provide additional data for FGF regulation of MIER genes to support the characterization of a family of genes that are upregulated by FGF.
FIG. 49 shows the isolation from a human cDNA library of partial cDNAs representing human MIER genes by PCR using Xenopus sequence primers. PCR was performed at low stringency to allow for possible mismatch between the Xenopus and human sequences.

Certain members of the M-MIER family of proteins are normally expressed during embryogenesis. Thus, the proteins should not be present in mature or adult cells. Of these proteins that are not present in adult cells, those that do appear can form the basis of a cancer-antigen indicating a cell that has turned cancerous. This can be determined, for example, by screening using a labelled nucleic acid probe indicating the presence of mRNA for the M-MIER proteins, that is not present at the same level in normal, healthy cells. In the alternative, labelled antibodies can be used to detect M-MIER protein as an antigenic determinant of cancerous growth. These types of results are presented in FIG. 46.

Vaccines

In a preferred embodiment, the invention relates to specific DNA vaccines and methods of treating cancer using the immune system and/or providing protective immunity to mammals. "Protective immunity" conferred by the method of the invention can elicit humoral and/or cell-mediated immune responses to cancerous growth, but more importantly interferes with the activity, spread, or growth of a cell that has become cancerous and has begun to express M-MIER nucleic acids and/or proteins following a subsequent challenge after vaccination.

The DNA vaccines of the invention are transcription units containing DNA encoding a M-MIER polypeptide or protein. In the method of the present invention, a DNA vaccine is administered to an individual as a mode of therapy, and/or in whom protective immunization is desired. An object of the invention is to provide an immune response and protective immunity to an animal using a DNA vaccine encoding a M-MIER protein as it has the potential of achieving high levels of protection in the virtual absence of side effects. Such DNA vaccines are also stable, easy to administer, and sufficiently cost-effective for widespread distribution.

An object of the invention is to provide protective immunity to an inoculated host. If the inoculated host is a female animal, an object of the invention is to provide protection in the offspring of that female.

The invention features a DNA vaccine containing a M-MIER DNA transcription unit (i.e., an isolated nucleotide sequence encoding a M-MIER-encoded protein or polypeptide). The nucleotide sequence is operably linked to transcriptional and translational regulatory sequences for expression of the M-MIER-coded polypeptide in a cell of a vertebrate. Preferably the polypeptide encoded by the DNA vaccine of the invention is a sequence belonging to M-MIER. Preferably, the nucleotide sequence encoding the polypeptide is contained in a plasmid vector.

The DNA vaccines can be administered to mammals such as humans expressing tumor associated antigens, such as the ER1 protein.

The DNA vaccines of the invention are preferably contained in a physiologically acceptable carrier for in vivo administration to a cell of a vertebrate. Administration of the DNA vaccines of the invention provide an immune response or protective immunity.

The invention also features a method of providing an immune response and protective immunity to a mammal against cancerous growth of cells expressing such a tumor associated antigen. The method includes administering to a cell of a vertebrate a DNA transcription unit encoding a desired M-MIER-encoded antigen operably linked to a promoter sequence. Expression of the DNA transcription unit in the cell elicits a humoral immune response, a cell-mediated immune response, or both against the cell expressing the protein product of the DNA transcription unit, the tumor associated antigen, which in this invention would be a M-MIER-encoded antigen.

The promoter operably linked to the DNA transcription unit is of nonretroviral or retroviral origin. Preferably the promoter is the cytomegalovirus immediate-early enhancer promoter. The desired M-MIER-encoded antigen encoded by the DNA transcription unit is one of the members of the M-MIER family, demonstrated to be expressed at significantly high levels only in cancerous cells in the mature organism.

The DNA transcription unit of the method of the invention is preferably contained in a physiologically acceptable carrier and is administered to the vertebrate by routes including, but not limited to, inhalation, intravenous, intramuscular, intraperitoneal, intradermal, and subcutaneous administration. The DNA transcription unit in a physiologically acceptable carrier can also be administered by being contacted with a mucosal surface of the vertebrate.

Preferably, administration is performed by particle bombardment using gold beads coated with the DNA transcription units of the invention. Preferably, the gold beads are 1 mm, to 2 mm in diameter. The coated beads are preferably administered intradermally, intramuscularly, by organ transfection, or by other routes useful in particle bombardment and known to those of ordinary skill in the art.

The term "immune response" refers herein to a cytotoxic T cells response or increased serum levels of antibodies to an antigen, or to the presence of neutralizing antibodies to an antigen, such as a M-MIER-encoded protein. The term "protection" or "protective immunity" refers herein to the ability of the serum antibodies and cytotoxic T cell response induced during immunization to protect (partially or totally) against cells expressing such tumor associated antigen. That is, a vertebrate immunized by the DNA vaccines of the invention will experience an immune attack on cancerous cells expressing such tumor associated antigen.

The term "promoter sequence" herein refers to a minimal sequence sufficient to direct transcription. Also included in the invention is an enhancer sequence which may or may not be contiguous with the promoter sequence. Enhancer sequences influence promoter-dependent gene expression and may be located in the 5' or 3' regions of the native gene. Expression is constitutive or inducible by external signals or agents. Optionally, expression is cell-type specific, tissue-specific, or species specific.

By the term "transcriptional and translational regulatory sequences" is meant nucleotide sequences positioned adjacent to a DNA coding sequence which direct transcription or translation of a coding sequence. The regulatory nucleotide sequences include any sequences which promote sufficient expression of a desired coding sequence and presentation of the protein product to the inoculated animal's immune system such that protective immunity is provided.

By the term "operably linked to transcriptional and translational regulatory sequences" is meant that a polypeptide coding sequence and minimal transcriptional and translational controlling sequences are connected in such a way as to permit polypeptide expression when the appropriate molecules (e.g., transcriptional activator proteins) are bound to the regulatory sequence(s). In the present invention, polypeptide expression in a target vertebrate cell is particularly preferred.

The term "isolated DNA" means DNA that is free of the genes and other nucleotide sequences that flank the gene in the naturally-occurring genome of the organism from which the isolated DNA of the invention is derived. The term therefore includes, for example, a recombinant DNA which is incorporated into a vector; into an autonomously replicating plasmid or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequences.

A preferred embodiment of this invention relates to a method of providing protective immunity to mammals. Protective immunity of the invention elicits humoral and/or cell-mediated immune responses. According to the present invention, a DNA transcription unit is administered to an individual in whom immunization and protection is desired.

DNA Transcription Units

A DNA transcription unit is a polynucleotide sequence, bounded by an initiation site and a termination site, that is transcribed to produce a primary transcript. As used herein, a "DNA transcription unit" includes at least two components: (1) antigen-encoding DNA, and (2) a transcriptional promoter element or elements operatively linked for expression of the antigen-encoding DNA. Antigen-encoding DNA can encode one or multiple antigens, such as antigens from two or more different proteins. The DNA transcription unit can additionally be inserted into a vector which includes sequences for expression of the DNA transcription unit.

A DNA transcription unit can optionally include additional sequences such as enhancer elements, splicing signals, termination and polyadenylation signals, viral replicons, and bacterial plasmid sequences. In the present method, a DNA transcription unit (i.e., one type of transcription unit) can be administered individually or in combination with one or more other types of DNA transcription units.

DNA transcription units can be produced by a number of known methods. For example, DNA encoding the desired antigen can be inserted into an expression vector (see, for example, Sambrook et al., Molecular Cloning, A Laboratory Manual, 2d, Cold Spring Harbor Laboratory Press (1989)). With the availability of automated nucleic acid synthesis equipment, DNA can be synthesized directly when the nucleotide sequence is known, or by a combination of polymerase chain reaction (PCR), cloning, and fermentation. Moreover, when the sequence of the desired polypeptide is known, a suitable coding sequence for the polynucleotide can be inferred.

The DNA transcription unit can be administered to an individual, or inoculated, in the presence of adjuvants or other substances that have the capability of promoting DNA uptake or recruiting immune system cells to the site of the inoculation. It should be understood that the DNA transcription unit itself is expressed in the host cell by transcription factors provided by the host cell, or provided by a DNA transcription unit.

The "desired antigen" can be any antigen or combination of antigens from encoded by a M-MIER gene. The antigen or antigens can be naturally occurring, or can be mutated or specially modified. The antigen or antigens can represent different forms, such as subgroups (clades), or subtypes. These antigens may or may not be structural components of a protein encoded by a M-MIER gene. The encoded antigens can be translation products or polypeptides. The polypeptides can be of various lengths, and can undergo normal host cell modifications such as glycosylation, myristoylation, or phosphorylation. In addition, they can be designated to undergo intracellular, extracellular, or cell-surface expression. Furthermore, they can be designed to undergo assembly and release from cells.

Administration of DNA Transcription Units

An individual can be inoculated through any parenteral route. For example, an individual can be inoculated by intravenous, intraperitoneal, intradermal, subcutaneous, inhalation, or intramuscular routes, or by particle bombardment using a gene gun. Muscle is a useful site for the delivery and expression of DNA transcription unit-encoded polynucleotides, because animals have a proportionately large muscle mass which is conveniently accessed by direct injection through the skin. A comparatively large dose of polynucleotides can be deposited into muscle by multiple and/or repetitive injections, for example, to extend therapy over long periods of time. Muscle cells are injected with polynucleotides encoding immunogenic polypeptides, and these polypeptides are presented by muscle cells in the context of antigens of the major histocompatibility complex to provoke a selected immune response against the immunogen (see, e.g., Felgner, et al. WO90/11092, herein incorporated by reference).

The epidermis is another useful site for the delivery and expression of polynucleotides, because it is conveniently accessed by direct injection or particle bombardment. A comparatively large dose of polynucleotides can be deposited in the epidermis by multiple injections or bombardments to extend therapy over long periods of time. In immunization strategies of the invention, skin cells are injected with polynucleotides coding for immunogenic polypeptides, and these polypeptides are presented by skin cells in the context of antigens of the major histocompatibility complex to provoke a selected immune response against the immunogen.

In addition, an individual can be inoculated by a mucosal route. The DNA transcription unit can be administered to a mucosal surface by a variety of methods including DNA-containing nose-drops, inhalants, suppositories, microsphere encapsulated DNA, or by bombardment with DNA coated gold particles. For example, the DNA transcription unit can be administered to a respiratory mucosal surface, such as the nares or the trachea.

Any appropriate physiologically compatible medium, such as saline for injection, or gold particles for particle bombardment, is suitable for introducing the DNA transcription unit into an individual.

M-MIER Polypeptides

In one embodiment, the present invention contemplates an isolated and purified M-MIER polypeptides such as ER1 polypeptide. Preferably, a M-MIER Polypeptide of the invention is a recombinant polypeptide. Preferably, an exemplary M-MIER polypeptide of the present invention comprises an amino acid sequence of FIG. 22.

Polypeptides are disclosed herein as amino acid residue sequences. Those sequences are written left to right in the direction from the amino to the carboxy terminus. In accordance with standard nomenclature, amino acid residue sequences are denominated by either a single letter or a three letter code.

Modifications and changes may be made in the structure of a polypeptide of the present invention and still obtain a molecule having M-MIER-like characteristics. For example, certain amino acids may be substituted for other amino acids in a sequence without appreciable loss of activity. Because it is the interactive capacity and nature of a polypeptide that defines that polypeptide's biological functional activity, certain amino acid sequence substitutions may be made in a polypeptide sequence (or, of course, its underlying DNA coding sequence) and nevertheless obtain a polypeptide with like properties.

The importance of the hydropathic amino acid index in conferring interactive biologic function on a polypeptide is generally understood in the art (Kyte and Doolittle, 1982). It is known that certain amino acids may be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (F0.7); serine (−0.8); tryptophan (−0.9); tyrosine (−1.3); proline (−1.6); histidine (−3.2); glutamate (−3.5);

glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid may be substituted by another amino acid having a similar hydropathic index and still obtain a functionally equivalent polypeptide. In such changes, the substitution of amino acids whose hydropathic indices are within ±0.2 is preferred, those which are within ±0.1 are particularly preferred, and those within ±0.05 are even more particularly preferred.

Substitution of like amino acids may also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e., with a biological property of the polypeptide.

As detailed in U.S. Pat. No. 4,554,101, the following hydrophilicity values have been assigned to amino acid residues: arginine (+3.0); lysine (+3.0); aspartate (+3.0.±0.1); glutamate (+3.0.±0.1); serine (+0.3); asparagine (+0.2); glutamine (+0.2); glycine (0); proline (−0.5±0.1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid may be substituted for another having a similar hydrophilicity value and still obtain a biologically equivalent, and in particular, an immunologically equivalent polypeptide. In such changes, the substitution of amino acids whose hydrophilicity values are within ±0.2 is preferred, those which are within ±0.1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of a M-MIER polypeptide as set forth above.

Biological or functional equivalents of a polypeptide may also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes may be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to 25 nucleotides in length is preferred, with about 5 to 10 residues on both sides of the junction of the sequence being altered.

TABLE 1

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp; Phe |
| Val | Ile; Leu |

The technique of site-specific mutagenesis is generally well-known in the art (Adelman et al., 1983). As will be appreciated, the technique typically employs a phage vector which may exist in both a single stranded and double stranded form. Typical vectors useful in site-directed mutagenesis include vectors such as the M13 phage (Messing et al., 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the M-MIER polypeptide sequence selected. An oligonucleotide primer bearing the desired mutated sequence is prepared, generally synthetically, for example, by the method of Crea, et al., (1978). This primer is then annealed to the singled-stranded vector, and extended by the use of enzymes such as the Klenow fragment of E. coli polymerase I, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutation.

Commercially available kits come with all the reagents necessary, except the oligonucleotide primers.

Expression Vectors

In an alternate embodiment, the present invention provides expression vectors comprising a polynucleotide that encodes a M-MIER polypeptide. Preferably, an expression vector of the present invention comprises a polynucleotide that encodes a polypeptide comprising an amino acid residue sequence of one of the members of the M-MIER gene family, eg. er1 as in FIG. 22. More preferably, an expression vector of the present invention comprises a polynucleotide comprising a nucleotide base sequence of FIG. 22. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer may function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer may be located downstream from the initiation site and may be at a considerable distance from that site.

An enhancer-promoter used in a vector construct of the present invention may be any enhancer-promoter that drives expression in a cell to be transfected. By employing an enhancer-promoter with well-known properties, the level and pattern of gene product expression may be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (RNA). Transcription-terminating regions are well-known in the art. A preferred transcription-terminating region used in an adenovirus vector construct of the present invention comprises a polyadenylation signal of SV40 or the protamine gene.

An expression vector comprises a polynucleotide that encodes a M-MIER polypeptide. Such a polynucleotide is meant to include a sequence of nucleotide bases encoding a M-MIER polypeptide sufficient in length to distinguish said segment from a polynucleotide segment encoding a nm-MIER polypeptide. A polypeptide of the invention may also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

An expression vector of the present invention comprises a polynucleotide that encodes a polypeptide comprising an amino acid residue sequence of FIG. 22. An expression vector may include a M-MIER polypeptide-coding region itself or any of the M-MIER polypeptides noted above or it may contain coding regions bearing selected alterations or modifications in the basic coding region of such a M-MIER polypeptide.

Alternatively, such vectors or fragments may code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville, Calif.). In certain cases, and specifically in the case of these individual mammalian expression vectors, the resulting constructs may require co-transfection with a vector containing a selectable marker such as pSV2neo. Via co-transfection into a dihydrofolate reductase-deficient Chinese hamster ovary cell line, such as DG44, clones expressing opioid polypeptides by virtue of DNA incorporated into such expression vectors may be detected.

A DNA molecule of the present invention may be incorporated into a vector using standard techniques well known in the art. For instance, the vector pUC18 has been demonstrated to be of particular value. Likewise, the related vectors M13mp18 and M13mp19 may be used in certain embodiments of the invention, in particular, in performing dideoxy sequencing.

An expression vector of the present invention is useful both as a means for preparing quantities of the M-MIER polypeptide-encoding DNA itself, and as a means for preparing the encoded polypeptide and peptides. It is contemplated that where M-MIER polypeptides of the invention are made by recombinant means, one may employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic M-MIER polypeptides are anticipated using the teaching of the disclosed invention, one likely expresses such sequences in eukaryotic hosts. However, even where the DNA segment encodes a eukaryotic M-MIER polypeptide, it is contemplated that prokaryotic expression may have some additional applicability. Therefore, the invention may be used in combination with vectors which may shuttle between the eukaryotic and prokaryotic cells. Such a system is described herein which allows the use of bacterial host cells as well as eukaryotic host cells.

Where expression of recombinant M-MIER polypeptides is desired and a eukaryotic host is contemplated, it is most desirable to employ a vector such as a plasmid, that incorporates a eukaryotic origin of replication.

Additionally, for the purposes of expression in eukaryotic systems, one desires to position the M-MIER encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the M-MIER polypeptide, an appropriate polyadenylation side.

The pCMV plasmids are a series of mammalian expression vectors of particular utility in the present invention. The vectors are designed for use in essentially all cultured cells and work extremely well in SV40-transformed simian COS cell lines. The pCMV1, pCMV2, pCMV3, and pCMV5 vectors differ from each other in certain unique restriction sites in the polylinker region of each plasmid. pCMV4 differs from the other four plasmids in containing a translation enhancer in the sequence prior to the polylinker. While they are not directly derived from the pCMV1–pCMV5 series of vectors, the functionally similar pCMV6b and pCMV6c vectors are commercially available (Chiron Corp., Emeryville, Calif.) and are identical except for the orientation of the polylinker region which is reversed in one relative to the other.

The universal components of the pCMV vectors are as follows: The vector backbone is pTZ18R (Pharmacia, Piscataway, N.J.), and contains a bacteriophage f1 origin of replication for production of single stranded DNA and an ampicillin (amp)-resistance gene. The CMV region consists of nucleotides −760 to +3 of the powerful promoter-regulatory region of the human cytomegalovirus (Towne stain) major immediate early gene (Thomsen et al., 1984; Boshart et al., 1985). The human growth hormone fragment (hGH) contains transcription termination and polyadenylation signals representing sequences 1533 to 2157 of this gene (Seeber-1g, 1982). There is an Alu middle repetitive DNA sequence in this fragment. Finally, the SV40 origin of replication and early region promoter-enhancer derived from the pcD-X plasmid (HindIII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter was added C'. The sequence acts as a translational enhancer by decreasing the requirements for initiation factors in polypeptide synthesis (Jobling et al., 1987; Browning et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, Gsx polypeptide, polypeptide phosphatase, synaptophysin, synapsin, insulin receptor, influenza hemagglutinin, androgen receptor, sterol 26-hydroxylase, steroid 17- and 21-hydroxylase, cytochrome P-450 oxidoreductase, β-adrenergic receptor, folate receptor, cholesterol side chain cleavage enzyme, and a host of other cDNAs. It should be noted that the SV40 promoter in these plasmids may be used to express other genes such as dominant selectable markers. Finally, there is an ATG sequence in the polylinker between the HindIII and PstI sites in pCMU that may cause sperlious translation initiation. This codon should be avoided if possible in expression plasmids. A paper describing the construction and use of the parenteral pCMV1 and pCMV4 vectors has been published (Anderson et al., 1989b).

Transfected Cells

In yet another embodiment, the present invention provides recombinant host cells transformed or transfected with a polynucleotide that encodes an M-MIER polypeptide, as well as transgenic cells derived from those transformed or transfected cells. Preferably, a recombinant host cell of the present invention is transfected with a polynucleotide of FIG. 22. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook et al., 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells may be transfected at any one time. Because of its high efficiency, transfection mediated by calcium phosphate or DEAE-dextran is the method of choice for studies requiring transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with culter-led mammalian cells. After fusion of the cell membranes (usually with polyethylene glycol), the contents of the bacterium are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandomly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closer-1e of the pores. Electroporation may be extremely efficient and may be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies may be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet et al., 1992).

A transfected cell may be prokaryotic or eukaryotic. Preferably, the host cells of the invention are eukaryotic host cells. More preferably, the recombinant host cells of the invention are COS-1 cells. Where it is of interest to produce a human M-MIER polypeptides, culter-1ed mammalian or human cells are of particular interest.

In another aspect, the recombinant host cells of the present invention are prokaryotic host cells. Preferably, the recombinant host cells of the invention are bacterial cells of the DH™. (GIBCO BRL, Gaithersburg, Md.) strain of *E. coli*. In general, prokaryotes are preferred for the initial cloning of DNA sequences and constructing the vectors useful in the invention. For example, *E. coli* K12 strains may be particularly useful. Other microbial strains which may be used include *E. coli* B, and *E. coli* X1776 (ATCC No. 31537). These examples are, of coer-1se, intended to be illustrative rather than limiting.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* may be transformed using pBR322, a plasmid derived from an *E. coli* species (Bolivar et al., 1977). pBR322 contains genes for amp and tetracycline resistance and thus provides easy means for identifying transformed cells.

The pBR322 or other microbial plasmid or phage must also contain, or be modified to contain, promoters which may be used by the microbial organism for expression of its own polypeptides.

Those promoters most commonly used in recombinant DNA construction include the beta.-lactamase (penicillinase) and .beta.-galactosidase (.beta.-Gal) promoter systems (Chang et al., 1978; Itaker-1a et al., 1977; Goeddel et al., 1979; Goeddel et al., 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce promoters functional into plasmid vectors (Siebwenlist et al., 1980).

In addition to prokaryotes, eukaryotic microbes, such as yeast may also be used. *Saccharomyces cerevisiae* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC No. 44076 or PEP4-1 (Jones, 1977). The presence of the trpL lesion as a characteristic of the yeast host cell genome then provides an effective environment for detecting transformation by growth in the absence of tryptophan.

Suitable promotor sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms may also be used as hosts. In principle, any such cell culture may be employed, whether from vertebrate or invertebrate culture. However, interest has been greatest in vertebrate cells, and propagation of vertebrate cells in tissue culture has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus (CMV) and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally.associated with the desired gene sequence, provided such control sequences are compatible with the host cell systems.

An origin of replication may be provided with by construction of the vector to include an exogenous origin, such as may be derived from SV40 or other viral (e.g., Polyoma, Adeno, VSV, BPV, CMV) source, or may be provided by the host cell chromosomal replication mechanism. If the vector is integrated into the host cell chromosome, the latter is often sufficient.

Preparing a Recombinant M-MIER Polypeptide

In yet another embodiment, the present invention describes a process of preparing an M-MIER polypeptide comprising transfecting cells with a polynucleotide that encodes an M-MIER polypeptide to produce a transformed host cell; and maintaining the transformed host cell under biological conditions sufficient for expression of the polypeptide. Preferably, the transformed host cell is a eukaryotic cell. Even more preferably, the polynucleotide transfected into the transformed cells comprises a nucleotide base sequence of FIG. 22. Most preferably transfection is accomplished using a hereinbefore disclosed expression vector.

A host cell used in the process is capable of expressing a functional, recombinant M-MIER polypeptide. A variety of cells are amenable to a process of the invention, for instance, yeasts cells, human cell lines, and other eukaryotic cell lines known well to those of the art.

Following transfection, the cell is maintained under culture conditions for a period of time sufficient for expression of an M-MIER polypeptide. Culture conditions are well known in the art and include ionic composition and concentration, temperature, pH and the like. Typically, transfected cells are maintained under culture conditions in a culture medium. Suitable medium for various cell types are well-known in the art. In a preferred embodiment, temperature is from about 20° C. to about 50° C., more preferably from about 30° C. to about 40° C., and even more preferably, about 37° C.

pH is preferably from about a value of 6.0 to a value of about 8.0, more preferably from about a value of about 6.8 to a value of about 7.8, and most preferably, about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well-known in the art.

Transfected cells are maintained for a period of time sufficient for expression of an M-MIER polypeptide. A suitable time depends inter alia upon the cell type used and is readily determinable by a skilled artisan. Typically, maintenance time is from about 2 to about 14 days.

Recombinant M-MIER polypeptide is recovered or collected either from the transfected cells or the medium in which those cells are cultured. Recovery comprises isolating and purifying the M-MIER polypeptide. Isolation and purification techniques for polypeptides are well-known in the art and include such procedures as precipitation, filtration, chromatography, electrophoresis and the like.

Antibodies

In still another embodiment, the present invention provides an antibody immunoreactive with an M-MIER polypeptide (e.g., one which is specific for M-MIER polypeptide). Preferably, an antibody of the invention is a monoclonal antibody. Preferably, an M-MIER polypeptide comprises an amino acid residue sequence of FIG. Means for preparing and characterizing antibodies are well-known in the art (See, e.g., "Antibodies: A Laboratory Manual", E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species may be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well-known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin may also be used as carriers.

Means for conjugating a polypeptide or a polynucleotide to a carrier protein are well-known in the art and include glutaraldehyde, m-maleimidobencoyl-N-hydroxysuccinimide ester, carbodiimide and bis-biazotized benzidine.

As is also well-known in the art, immunogencity to a particular immunogen may be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes may be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal may be bled and the serum isolated and stored.

In another aspect, the present invention contemplates a process of producing an antibody immunoreactive with an M-MIER polypeptide comprising the steps of (a) transfecting a recombinant host cell with a polynucleotide that encodes an M-MIER polypeptide; (b) culturing the host cell under conditions sufficient for expression of the polypeptide; (c) recovering the polypeptide; and (d) preparing an antibody to the polypeptide. Preferably, the host cell is transfected with a polynucleotide of FIG. 22. The present invention also provides an antibody prepared according to the process described above.

A monoclonal antibody of the present invention may be readily prepared through use of well-known techniques such as those exemplified in U.S. Pat. No. 4,196,265. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones may then be propagated indefinitely to provide the monoclonal antibody.

By way of specific example, to produce an antibody of the present invention, mice are injected intraperitoneally with between about 1 to about 200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they may be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as hypoxanthine-aminopterin-thymidine (HAT) medium. Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) may grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention may be recognized as antigens, and thus identified. Once identified, those polypeptides and polynucleotide may be isolated and purified by techniques such as antibody-affinity chromatography. In antibody-affinity chromatography, a monoclonal antibody is bound to a solid substrate and exposed to a solution containing the desired antigen. The antigen is removed from the solution through an immuno-specific reaction with the bound antibody. The polypeptide or polynucleotide is then easily removed from the substrate and purified.

Pharmaceutical Compositions

In a preferred embodiment, the present invention provides a pharmaceutical composition comprising an M-MIER polypeptide and a physiologically acceptable carrier. More preferably, a pharmaceutical composition comprises an M-MIER polypeptide comprising an amino acid residue sequence of FIG. 22. Alternatively, pharmaceutical compositions include a polynucleotide that encodes an M-MIER polypeptide and a physiologically acceptable carrier. An example of a useful pharmaceutical composition includes a polynucleotide that has the nucleotide sequence of FIG. 22.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it does not cause any untoward reactions in the individual receiving the vector construct. Means of purifying the vector may involve the use of buoyant density gradients, such as cesium chloride gradient centrifugation.

A carrier may also be a liposome. Means for using liposomes as delivery vehicles are well-known in the art (See, e.g., Gabizon et al., 1990; Ferruti and Tanzi, 1986; Ranade, 1989).

A transfected cell may also serve as a carrier. By way of example, a liver cell may be removed from an organism, transfected with a polynucleotide of the present invention using methods set forth above and then the transfected cell returned to the organism (e.g., injected intravascularly).

Detecting M-MIER Encoding Polynucleotides and M-MIER Polypeptides

Alternatively, the present invention provides a process of detecting an M-MIER polypeptide, wherein the process comprises immunoreacting the polypeptide with an antibody prepared according to a process described above to form an antibody-polypeptide conjugate, and detecting the conjugate.

In yet another embodiment, the present invention contemplates a process of detecting a messenger RNA transcript that encodes an M-MIER polypeptide, wherein the process comprises (a) hybridizing the messenger RNA transcript with a polynucleotide sequence that encodes an M-MIER polypeptide to form a duplex; and (b) detecting the duplex. Alternatively, the present invention provides a process of detecting a DNA molecule that encodes an M-MIER polypeptide, wherein the process comprises (a) hybridizing a DNA molecule with a polynucleotide that encodes an M-MIER polypeptide to form a duplex; and (b) detecting the duplex.

Screening Assays

In yet another aspect, the present invention contemplates a process of screening substances for their ability to interact with an M-MIER polypeptide comprising the steps of providing an M-MIER polypeptide, and testing the ability of selected substances to interact with the M-MIER polypeptide.

Utilizing the methods and compositions of the present invention, screening assays for the testing of candidate substances such as agonists and antagonists of M-MIERs may be derived. A candidate substance is a substance which potentially may interact with or modulate, by binding or other intramolecular interaction, an M-MIER polypeptide. In some instances, such a candidate substance will be an agonist of the polypeptide and in other instances may exhibit antagonistic attributes when interacting with the polypeptide. In other instances, such substances may have mixed agonistic and antagonistic properties or may modulate the M-MIER in other ways.

Recombinant polypeptide expression systems of the present invention possess definite advantages over tissue-based systems. Such a method of the present invention makes it possible to produce large quantities of M-MIERs for use in screening assays. More important, however, is the relative purity of the polypeptides provided by the present invention. A relatively pure polypeptide preparation for assaying a protein-protein interaction makes it possible to use elutive methods without invoking competing, and unwanted, side-reactions.

Cloned expression systems such as those of the present invention are also useful where there is difficulty in obtaining tissue that satisfactorily expresses a particular polypeptide. Cost is another very real advantage, at least with regard to the microbial expression systems of the present invention. For antagonists in a primary screen, microorganism expression systems of the present invention are inexpensive in comparison to prior art tissue-screening methods.

Traditionally, screening assays employed the use of crude polypeptide preparations. Typically, animal tissue slices thought to be rich in the polypeptide of interest was the source of the polypeptide. Alternatively, investigators homogenized the tissue and used the crude homogenate as a polypeptide source. A major difficulty with this approach is the provision that the tissue contain only a single polypeptide type being expressed. The data obtained therefore could not be definitively correlated with a particular polypeptide. With the recent cloning of polypeptide sub-types and sub-sub-types, this difficulty is highlighted. A second fundamental difficulty with the traditional approach is the unavailability of human tissue for screening potential drugs. The traditional approach almost invariably utilized animal polypeptides. With the cloning of human polypeptides, there is a need for screening assays which utilize human polypeptides.

With the availability of cloned polypeptides, recombinant polypeptide screening systems have several advantages over tissue based systems. A major advantage is that the investigator may now control the type of polypeptide that is utilized in a screening assay. Specific polypeptide sub-types and sub-sub-types may be preferentially expressed and its interaction with a ligand may be identified. Other advantages include the availability of large amounts of polypeptide, the availability of rare polypeptides previously unavailable in tissue samples, and the lack of expenses associated with the maintenance of live animals.

Screening assays of the present invention generally involve determining the ability of a candidate substance to bind to the polypeptide and to affect the activity of the polypeptide, such as the screening of candidate substances to identify those that inhibit or otherwise modify the polypeptide's function. Typically, this method includes preparing a recombinant polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect the enzymatic activity of the human polypeptide, and thus can be suitable for use in humans.

A screening assay provides a polypeptide under conditions suitable for the binding of an agent to the polypeptide. These conditions include but are not limited to pH, temperature, tonicity, the presence of relevant cofactors, and relevant modifications to the polypeptide such as glycosylation or prenylation. It is contemplated that the polypeptide can be expressed and utilized in a prokaryotic or eukaryotic cell. The host cell expressing the polypeptide can be used whole or the polypeptide can be isolated from the host cell. The polypeptide can be membrane bound in the membrane of the host cell or it can be free in the cytosol of the host cell. The host cell can also be fractionated into sub-cellular fractions where the polypeptide can be found. For example, cells expressing the polypeptide can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8, and most preferably, about 7.4. In a preferred embodiment, temperature is from about 20° C. to about 50° C., more preferably, from about 30° C. to about 40° C., and even more preferably about 37° C. Osmolality is preferably from about 5 milliosmols per liter (mosm/L) to about 400 mosm/l, and more preferably, from about 200 milliosmols per liter to about 400 mosm/l and, even more preferably from about 290 mosm/L to about 310 mosm/L. The presence of cofactors can be required for the proper functioning of the polypeptide. Typical cofactors include sodium, potassium, calcium, magnesium, and chloride. In addition, small, non-peptide molecules, known as prosthetic groups may also be required. Other biological conditions needed for polypeptide function are well-known in the art.

It is well-known in the art that proteins can be reconstituted in artificial membranes, vesicles or liposomes. (Danboldt et al., 1990). The present invention contemplates that the polypeptide can be incorporated into artificial membranes, vesicles or liposomes. The reconstituted polypeptide can be utilized in screening assays.

It is further contemplated that a polypeptide of the present invention can be coupled to a solid support, e.g., to agarose beads, polyacrylamide beads, polyacrylic beads or other solid matrices capable of being coupled to polypeptides. Well-known coupling agents include cyanogen bromide (CNBr), carbonyldiiriiidazole, tosyl chloride, and glutaraldehyde.

In a typical screening assay for identifying candidate substances, one employs the same recombinant expression host as the starting source for obtaining the polypeptide, generally prepared in the form of a crude homogenate. Recombinant cells expressing the polypeptide are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substances, such as agonists and antagonists, are added to the admixture in convenient concentrations and the interaction between the candidate substance and the polypeptide is monitored.

Where one uses an appropriate known substrate for the polypeptide, one can, in the foregoing manner, obtain a baseline activity for the recombinantly produced polypeptide. Then, to test for inhibitors or modifiers of the polypeptide function, one can incorporate into the admixture a candidate substance whose effect on the polypeptide is unknown. By comparing reactions which are carried out in the presence or absence of the candidate substance, one can then obtain information regarding the effect of the candidate substance on the normal function of the polypeptide.

Accordingly, this aspect of the present invention will provide those of skill in the art with methodology that allows for the identification of candidate substances having the ability to modify the action of M-MIER polypeptides in one or more manner.

Additionally, screening assays for the testing of candidate substances are designed to allow the determination of structure-activity relationships of agonists or antagonists with the polypeptides, e.g., comparisons of binding between naturally-occurring hormones or other substances capable of interacting or otherwise modulating with the polypeptide; or comparison of the activity caused by the binding of such molecules to the polypeptide.

In certain aspects, the polypeptides of the invention are crystallized in order to carry out x-ray crystallographic studies as a means of evaluating interactions with candidate substances or other molecules with the M-MIER polypeptide. For instance, the purified recombinant polypeptides of the invention, when crystallized in a suitable form, are amenable to detection of intra-molecular interactions by x-ray crystallography.

The recombinantly-produced M-MIER polypeptide may be used in screening assays for the identification of substances which may inhibit or otherwise modify or alter the function of the polypeptide. The use of recombinantly-produced polypeptide is of particular benefit because the naturally-occurring polypeptide is present in only small quantities and has proven difficult to purify. Moreover, this provides a ready source of polypeptide, which has heretofore been unavailable.

A screening assay of the invention, in preferred embodiments, conveniently employs an M-MIER polypeptide directly from the recombinant host in which it is produced. This is achieved most preferably by simply expressing the selected polypeptide within the recombinant host, typically a eukaryotic host, followed by preparing a crude homogenate which includes the enzyme. A portion of the crude homogenate is then admixed with an appropriate effector of the polypeptide along with the candidate substance to be tested. By comparing the binding of the selected effector to the polypeptide in the presence or absence of the candidate substance, one may obtain information regarding the physiological properties of the candidate substance.

There are believed to be a wide variety of embodiments which may be employed to determine the effect of the candidate substance on the polypeptides of the invention, and the invention is not intended to be limited to any one such method. However, it is generally desirable to employ a system wherein one may measure the ability of the polypeptide to bind to and or be modified by the effector employed in the presence of a particular substance.

The detection of an interaction between an agent and a polypeptide may be accomplished through techniques well-known in the art. These techniques include but are not limited to centrifugation, chromatography, electrophoresis and spectroscopy. The use of isotopically labeled reagents in conjunction with these techniques or alone is also contemplated. Commonly used radioactive isotopes include $^3$H, $^{14}$C, $^{22}$Na, $^{32}$P, $^{35}$S, $^{45}$Ca, $^{60}$Co, $^{125}$I, and $^{131}$I. Commonly used stable isotopes include $^2$H, $^{13}$C, $^{15}$N, and $^{18}$O.

For example, if an agent binds to the polypeptide of the present invention, the binding may be detected by using radiolabeled agent or radiolabeled polypeptide. Briefly, if radiolabeled agent or radiolabeled polypeptide is utilized, the agent-polypeptide complex may be detected by liquid scintillation or by exposure to x-ray film.

When an agent modifies the polypeptide, the modified polypeptide may be detected by differences in mobility between the modified polypeptide and the unmodified polypeptide through the use of chromatography, electrophoresis or centrifugation. When the technique utilized is centrifugation, the differences in mobility is known as the sedimentation coefficient. The modification may also be detected by differences between the spectroscopic properties of the modified and unmodified polypeptide. As a specific example, if an agent covalently modifies a polypeptide, the difference in retention times between modified and unmodified polypeptide on a high pressure liquid chromatography (HPLC) column may easily be detected. Alternatively, the spectroscopic differences between modified and unmodified polypeptide in the nuclear magnetic resonance (NMR) spectra may be detected. Or, one may focus on the agent and detect the differences in the spectroscopic properties or the difference in mobility between the free agent and the agent after modification of the polypeptide.

When a secondary polypeptide is provided, the agent-polypeptide-secondary polypeptide complex or the polypeptide-secondary polypeptide complex may be detected by differences in mobility or differences in spectroscopic properties as described above. The interaction of an agent and a polypeptide may also be detected by providing a reporter gene. Well-known reporter genes include β-Gal, chloramphenicol (Cml) transferase (CAT) and luciferase. The reporter gene is expressed by the host and the enzymatic reaction of the reporter gene product may be detected.

In one example, a mixture containing the polypeptide, effector and candidate substance is allowed to incubate. The unbound effector is separable from any effector/polypeptide complex so formed. One then simply measures the amount of each (e.g., versus a control to which no candidate substance has been added). This measurement may be made at various time points where velocity data is desired. From this, one determines the ability of the candidate substance to alter or modify the function of the polypeptide.

Numerous techniques are known for separating the effector from effector/polypeptide complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique may be employed so long as it is capable of differentiating between the effector and complex, and may be used to determine enzymatic function such as by identifying or quantifying the substrate and product.

Screening Assays for M-MIER Polypeptides

The present invention provides a process of screening a biological sample for the presence of an M-MIER polypeptide. A biological sample to be screened may be a biological fluid such as extracellular or intracellular fluid, a cell, a tissue extract, a tissue homogenate or a histological section. A biological sample may also be an isolated cell (e.g., in culture) or a collection of cells such as in a tissue sample or histology sample. A tissue sample may be suspended in a liquid medium or fixed onto a solid support such as a microscope slide.

In accordance with a screening assay process, a biological sample is contacted with an antibody specific for a M-MIER polypeptide whose presence is being assayed. Typically, one mixes the antibody and the M-MIER polypeptide, and either the antibody or the sample with the M-MIER polypeptide may be affixed to a solid support (e.g., a column or a microtiter plate). Optimal conditions for the reaction may be accomplished by adjusting temperature, pH, ionic concentration, etc.

Ionic composition and concentration may range from that of distilled water to a 2 molar solution of NaCl. Preferably, osmolality is from about 100 mosmols/l to about 400 mosmols/l, and more preferably, from about 200 mosmbls/l to about 300 mosmols/l. Temperature preferably is from about 4° C. to about 100° C., more preferably from about 15° C. to about 50° C., and even more preferably from about 25° C. to about 40° C. pH is preferably from about a value of 4.0 to a value of about 9.0, more preferably from about a value of 6.5 to a value of about 8.5, and even more preferably, from about a value of 7.0 to a value of about 7.5. The only limit on biological reaction conditions is that the conditions selected allow for antibody-polypeptide conjugate formation and that the conditions do not adversely affect either the antibody or the M-MIER polypeptide.

Incubation time varies with the biological conditions used, the concentration of antibody and polypeptide and the nature of the sample (e.g., fluid or tissue sample). Means for determining exposure time are well-known to one of ordinary skill in the art. Typically, where the sample is fluid and the concentration of polypeptide in that sample is about $10^{-10}$ M, exposure time is from about 10 min to about 200 min.

M-MIER polypeptide in the sample is determined by detecting the formation and presence of antibody-M-MIER polypeptide conjugates. Means for detecting such antibody-antigen (e.g., polypeptide) conjugates or complexes are well-known in the art and include such procedures as centrifugation, affinity chromatography and the like, binding of a secondary antibody to the antibody-candidate polypeptide complex. Detection may be accomplished by measuring an indicator affixed to the antibody. Exemplary and well-known such indicators include radioactive labels (e.g., $^{32}P$, $^{125}I$, $^{14}C$), a second antibody or an enzyme such as horse radish peroxidase. Methods for affixing indicators to antibodies are well-known in the art. Commercial kits are available.

Screening Assay for M-MIER Antibody

The present invention provides a process of screening a biological sample for the presence of antibodies immunoreactive with a M-MIER polypeptide (i.e., M-MIER antibody). In accordance with such a process, a biological sample is exposed to an M-MIER polypeptide under biological conditions and for a period of time sufficient for antibody-polypeptide conjugate formation and the formed conjugates are detected.

Screening Assay for a Polynucleotide Encoding A M-MIER Polypeptide

A DNA molecule and, particularly a probe molecule, may be used for hybridizing as oligonucleotide probes to a DNA source suspected of possessing an M-MIER polypeptide encoding polynucleotide or gene. The probing is usually accomplished by hybridizing the oligonucleotide to a DNA source suspected of possessing such a polypeptide gene. In some cases, the probes constitute only a single probe, and in others, the probes constitute a collection of probes based on a certain amino acid sequence or sequences of the M-MIER polypeptide and account in their diversity for the redundancy inherent in the genetic code.

A suitable source of DNA for probing in this manner is capable of expressing M-MIER polypeptides and may be a genomic library of a cell line of interest. Alternatively, a source of DNA may include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules may be used in a number of techniques including their use as: (1) diagnostic tools to detect normal and abnormal DNA sequences in DNA derived from patient's cells; (2) means for detecting and isolating other members of the M-MIER family and related polypeptides from a DNA library potentially containing such sequences; (3) primers for hybridizing to related sequences for the per-1pose of amplifying those sequences; and (4) primers for altering the native M-MIER-DNA sequences; as well as other techniques which rely on the similarity of the DNA sequences to those of the M-MIER DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected M-MIER gene. In these aspects, nucleic acid probes of an appropriate length are prepared based on a consideration of the selected M-MIER encoding sequence (e.g., a nucleic acid sequence such as shown in FIG. 22. The ability of such nucleic acid probes to specifically hybridize to M-MIER encoding sequences lend them particular utility in a variety of embodiments.

Most importantly, the probes are useful in a variety of assays for detecting the presence of complementary sequences in a given sample. These probes are useful in the preparation of mutant species primers and primers for preparing other genetic constructions.

To provide certain of the advantages in accordance with the invention, a preferred nucleic acid sequence employed for hybridization studies or assays includes probe sequences that are complementary to at least an about 14 to about 40 or so long nucleotide stretch of the M-MIER encoding sequence, such as shown in FIG. 22. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of about 14 to about 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

Accordingly, a nucleotide sequence of the present invention may be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by about 0.02M to about 0.15M NaCl at temperatures of about 50° C. to about 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate M-MIER coding sequences from related species, functional equivalents, or the like, less stringent hybridization conditions are typically needed to allow formation of the heteroduplex. Under such circumstances, one employs conditions such as from about 0.15M to about 0.9M salt, at temperatures ranging from about 20° C. to about 55° C. Cross-hybridizing species may thereby be readily identified as positively hybridizing signals with respect to control hybridizations. In any case, it is generally appreciated that conditions may be rendered more stringent by the addition of increasing amounts of formamide, which serves to destabilize the hybrid duplex in the same manner as increased temperature. Thus, hybridization conditions may be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which may be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantified, by means of the label.

Assay Kits

In another aspect, the present invention contemplates a diagnostic assay kit for detecting the presence of M-MIER polypeptide in a biological sample, where the kit comprises a first container containing a first antibody capable of immunoreacting with M-MIER polypeptide, with the first antibody present in an amount sufficient to perform at least one assay. An assay kit of the invention further optionally includes a second container containing a second antibody that immunoreacts with the first antibody. The antibodies used in the assay kits of the present invention may be monoclonal or polyclonal antibodies. For convenience, one may also provide the first antibody affixed to a solid support. Additionally, the first and second antibodies may be combined with an indicator, (e.g., a radioactive label or an enzyme).

The present invention also contemplates a diagnostic kit for screening agents for their ability to interact with an M-MIER. Such a kit will contain an M-MIER of the present invention. The kit may further contain reagents for detecting an interaction between an agent and a polypeptide of the present invention. The provided reagent may be radiolabeled. The kit may also contain a known radiolabeled agent that binds or interacts with a polypeptide of the present invention.

The present invention provides a diagnostic assay kit for detecting the presence, in a biological sample, of a polynucleotide that encodes an M-MIER polypeptide, the kits comprising a first container that contains a second polynucleotide identical or complementary to a segment of at least about 14 contiguous nucleotide bases of a polynucleotide of FIG. 22.

In another embodiment, the present invention contemplates a diagnostic assay kit for detecting the presence, in a biological sample, of an antibody immunoreactive with an M-MIER polypeptide, the kits comprising a first container containing an M-MIER polypeptide that immunoreacts with the antibody, with the polypeptide present in an amount sufficient to perform at least one assay. The reagents of the kit may be provided as a liquid solution, attached to a solid support or as a dried powder. When the reagent is provided in a liquid solution, the liquid solution is an aqueous solution. When the reagent provided is attached to a solid support, the solid support may be chromatograph media or a microscope slide. When the reagent provided is a dry powder, the powder may be reconstituted by the addition of a suitable solvent. The solvent may also be included in the kit.

Process of Modifying the Function of a Nuclear Polypeptide Using M-MIER

In another aspect, the present invention provides a process of altering the function of a nuclear polypeptide. In accordance with that process, a nuclear polypeptide is exposed to an M-MIER of the present invention. A preferred nuclear polypeptide used in such a process is the same as set forth above and includes nuclear polypeptides for thyroid hormone, vitamin D, retinoic acid and the like. Preferred M-MIERs and their corresponding DNA sequences are shown in FIG. 22.

The present invention provides DNA segments, purified polypeptides, methods for obtaining antibodies, methods of cloning and using recombinant host cells necessary to obtain and use M-MIERs. Accordingly, the present invention concerns generally compositions and methods for the preparation and use of M-MIERs.

M-MIER Genes and Isoforms in Other Organisms

Er-1 may be considered as a member of a subfamily of early response polypeptides that may include Mta1. It is probable that Er-1 isoforms are also encoded by multiple genes. Since nuclear polypeptides usually have a high homology, the sequences of M-MIER may be used as probes to screen cDNA libraries. Considering the fact that different isoforms of nuclear polypeptides may have different tissue distribution patterns and may be expressed to different extents in different tissues, the M-MIER may used as a probe to screen genomic libraries for genes encoding M-MIER isoforms.

The present invention also provides cDNA libraries which are useful for screening of additional M-MIER isoforms. Using the nucleotide sequences of the present invention, it is possible to determine structural and genetic information (including restriction enzyme analysis and DNA sequencing) concerning these positive clones. Such information will provide important information concerning the role of these isoforms in vivo and in vitro. M-MIER sequence information may be used to analyze M-MIER cDNAs and M-MIER-like gene sequences in other organisms. Using PCR techniques, restriction enzyme analysis, and DNA sequencing, the structure of these M-MIER-like isoform genes may be determined with relative facility.

The following examples illustrate preferred embodiments of the invention. Certain aspects of the following examples are described in terms of techniques and procedures found or contemplated by the present inventors to work well in the practice of the invention. These examples are exemplified through the use of standard laboratory practices of the inventor.

It should be appreciated by those of skill in the art that the techniques disclosed in the examples which follow represent techniques discovered by the inventor to function well in the practice of the invention, and thus may be considered to constitute preferred modes for its practice. However, those of skill in the art should, in light of the present disclosure, appreciate that many changes may be made in the specific embodiments which are disclosed and still obtain a like or similar result without departing from the spirit and scope of the invention.

EXAMPLE I

Demonstration That er1 is Tumor-Specific

Figure 24:
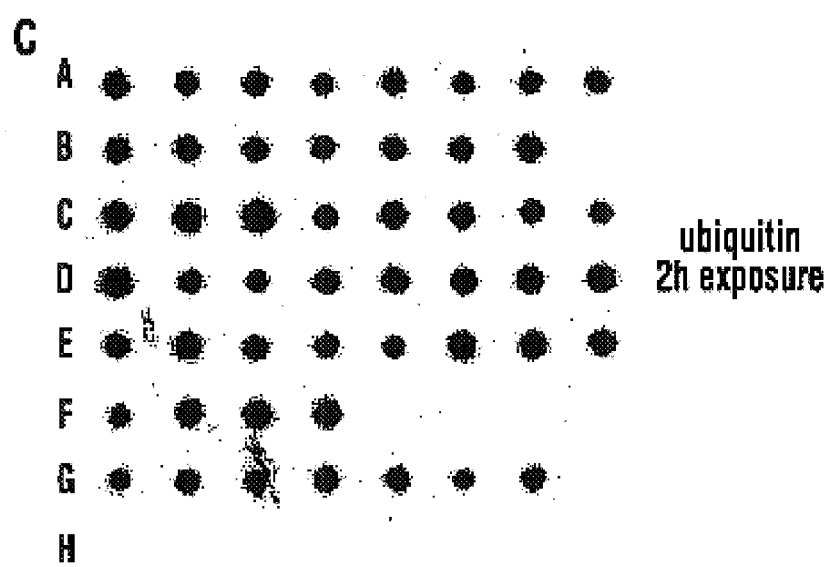
FIG. 24 presents expression of er1 in normal human adult and fetal tissues by dot blot analysis. Poly A+ mRNA from the human tissues listed in (A) was probed with [$\alpha$-$^{32}$P] human er13'UTRcDNA(B), then re-probed with [$\alpha$-$^{32}$P] ubiquitin cDNA (C). The probe used and the length of exposure, in days (d) or hours (h), is listed on the right. Row H contains several negative controls used to determine the specificity of the hybridization signal.
Figure 26:
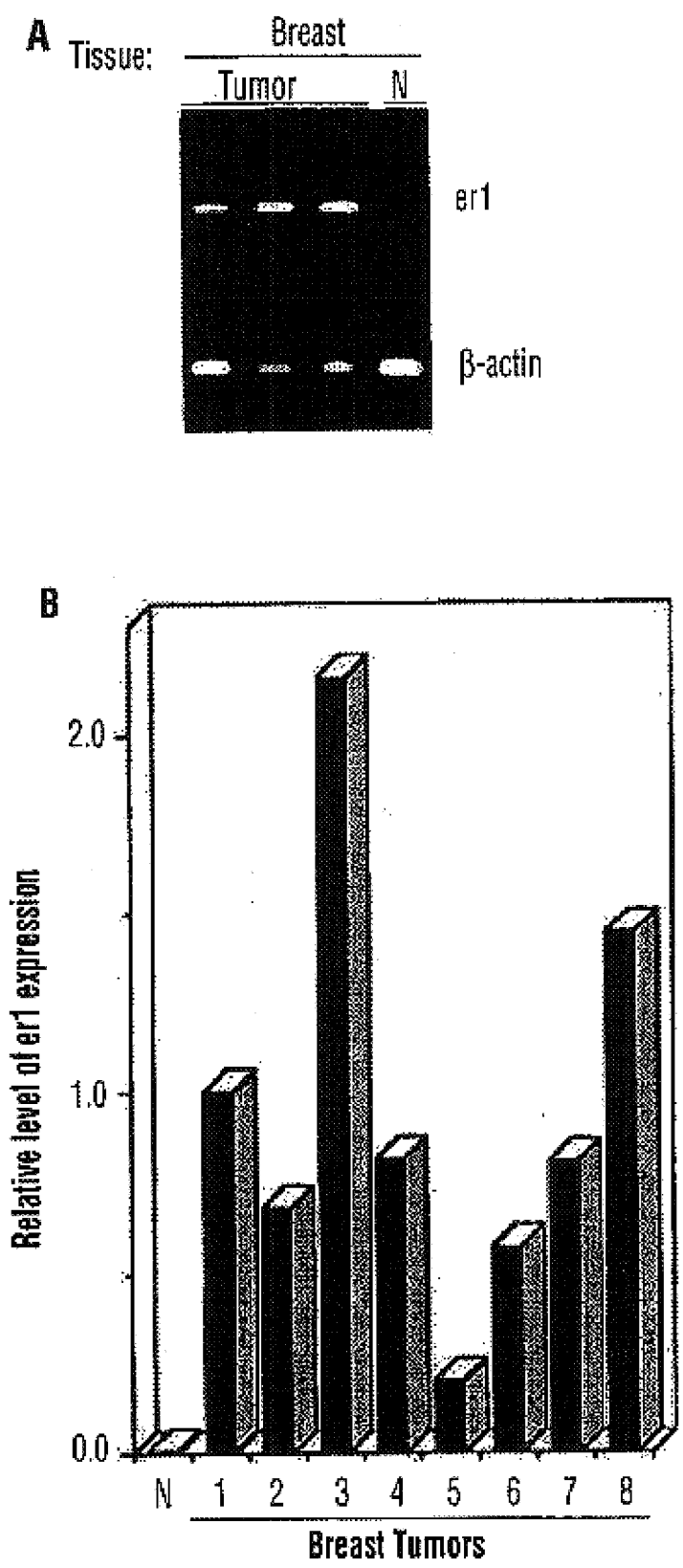
FIG. 26 shows results indicating upregulation of er1 in human breast tumors. (A)RT-PCR was performed on RNA extracted from paraffin sections of three different breast tumour samples (lanes 1–3) to amplify er1 (top panel) or β-actin (bottom panel) as a control. cDNA from normal breast tissue (N) was amplified with same primer pairs (lane 4). The PCR products were analyzed on a 1% agarose gel. (B) PCR was performed in the presence of [$\alpha$-$^{32}$P] cCTP on eight different breast tumour samples (1–8) and on normal breast tissue (N) as described in (A). Labelled PCR products were electrophoresed on a 6% polyacrylamide/6M urea gel and analyzed by densitometry, as described in of Example IV. The values plotted in the histogram are the ratio of er1 to β-actin densitometric values.
Figure 27:
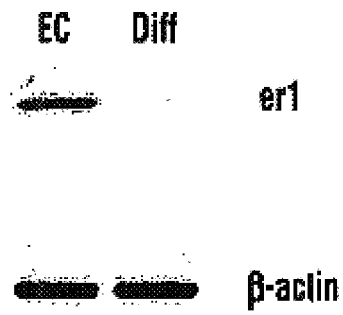
FIG. 27 shows RT-PCR analysis of er1 expression in undifferentiated (EC) and differentiated P19 cells (Diff) using mRNA for one member of M-MIER gene family, mouse er1, in mouse embryonal carcinoma cells before and after differentiation. mRNA was extracted from embryonal carcinoma cells (EC) and EC cells which have been induced to differentiate into adult tissues. Embryonal carcinoma are equivalent to the cells to the early mammalian embryo in that they can replace embryonic cells to give rise to a normal, tumour-free mouse in the embryonic environment. Note that er1 mRNA is highly expressed in the embryonal carcinoma cells but the level in the normal differentiated derivatives is drastically reduced when compared to the control actin mRNA. This data indicates that ER1 expression is a property of mammalian embryonic cells as was demonstrated in Xenopus embryos. This evidence adds support to the determination of ER1 as an embryonic FGF early response gene in mammals Moreover, these results indicate that ER1 is an excellent target as a tumour-specific antigen for therapeutic agents.
Figure 28:
FIG. 28 presents expression of human ER1 protein in normal breast and breast carcinoma cells lines. Protein extracts harvested from a normal breast cell line HS787 (N) and two breast carcinoma cells lines MCF-7 (T1) and MDA-468 (T2) and equivalent amounts of protein were subjected to Western blotting using anti-ER1 antibodies. Note the high levels of ER1 protein in the breast carcinoma cell lines compared to the normal breast cell line. The additional higher molecular weight forms of ER1 are modified by post-translational modifications including phosphorylation. This data demonstrates that the ER1 protein is expressed at high levels in breast carcinoma cell lines but not in normal breast cells. This confirms that the ER1 protein serves as a specific target for therapeutic agents (vaccines, drugs, antibodies) designed to specifically inhibit the growth or to kill breast cancer cells. The fact that ER1 is not detectable in normal adult cells makes it a superior target to many other "tumour-specific" antigens which are often expressed in adult cells; for example, carcinoembryonic antigen (CEA) which is now in clinical trials.
Figure 30:
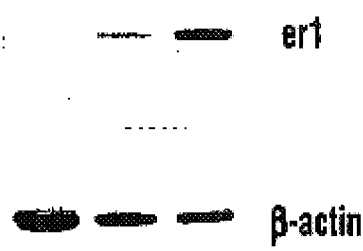
FIG. 30 presents results of RT-PCR analysis of er1 expression in primary cervical cells (N), immortalized (I) and transformed (T) cervical cells in experiments using a M-MIER family member, specifically showing expression of human er1 mRNA in cervical cells and in cervical carcinoma cell lines. mRNA was extracted from primary cervical cells (N), immortalized cervical cells (I) and cervical carcinoma (T) cell lines., Equivalent amounts of RNA were subjected to RT-PCR analysis to reveal the levels of er1 mRNA in these cells. Primary cervical cells are normal cells which have a limited lifespan in tissue culture. Immortalized cells are normal cervical cells which have acquired the ability for continuous growth in culture but cannot form tumours. Cervical carcinoma cell lines are transformed cells which demonstrate malignant growth in culture and form tumours. Note the increased levels of er1 mRNA in the immortalized and cervical carcinoma cells. This data indicates that there is a differential expression of er1 in cervical carcinoma versus normal cervical cells. Thus, like for breast cancers, er1 can serve as a therapeutic target for the specific inhibition of growth or the killing of cervical cancer cells. This evidence also suggests that the overexpression of ER1 may be a general phenomena in many types of cancer.
Figure 29:
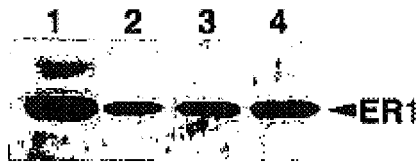
FIG. 29 is a Western blot showing expression of ER1 protein in four different clinical human breast tumour samples. Protein was extracted from a small piece of tumour tissue and run on a Western. The blot was stained with an anti-ER1antibody of the present invention. The results presented in this figure demonstrate that an antibody of the present invention can be used as a diagnostic tool for the mammalian protein and that breast tumours express the Er1 protein.
Figure 35:
FIG. 35 shows expression of ER1 protein in mammalian cells transfected with expression vectors containing the er1 cDNA sequence. The er1 plasmid was transfected in mouse NIH3T3 fibroblasts (lane 1) and rat L6 myoblasts (lane 2 and 3) using a liposome delivery system. This study demonstrates that our the er1 cDNA of the present invention which has been cloned into various expression plasmids can be transfected into cells not expressing ER1 and that cDNA can be transcribed and translated into ER1 protein which is detectable by our ER1 antibody.
Figure 36:
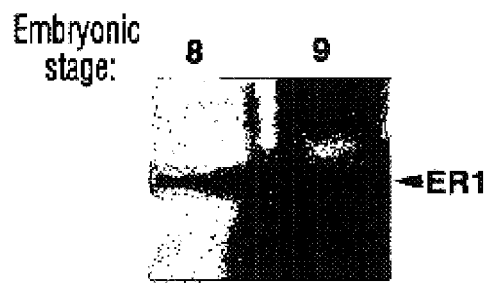
FIG. 36 shows phosphorylation of the Xenopus ER1 protein on serine and/or threonine. Extracts from Xenopus embryos were subjected to immunoprecipitation with anti-ER1 antibody followed by Western blotting. The blot was stained with a monoclonal antibody that recognizes phosphoserine and phosphothreonine. This figure shows that the ER1 protein is phosphorylated in the embryo and may represent a mechanism by which ER1 activity is regulated. This data suggests that ER1 activity may be controlled through cellular phosphorylations at these amino acids in the protein and that therapeutic modulation of phosphorylation of ER1 might regulate its activity.
Figure 37:
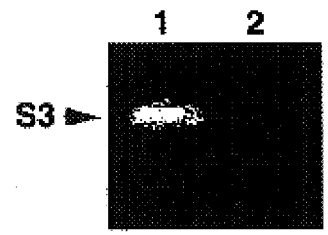
FIG. 37 presents evidence of downregulation of nm-MIER gene S3 by treatment with FGF. Xenopus embryonic cells were treated with FGF for 30 min, then the RNA was extracted, reverse-transcribed and subjected to PCR using primers corresponding to nm-MIER gene S3. The primers were designed using cloned sequence from S3. S3 is the only gene that appeared to be downregulated by FGF. This is an example of a nm-MIER gene (S3) which is downregulated by FGF. This is the opposite of what we is observed for er1, therefore, one would argue that expression of this particular gene would stop growth. These results demonstrate that this member of the MIER family could be an excellent target for gene therapy.
Figure 38:
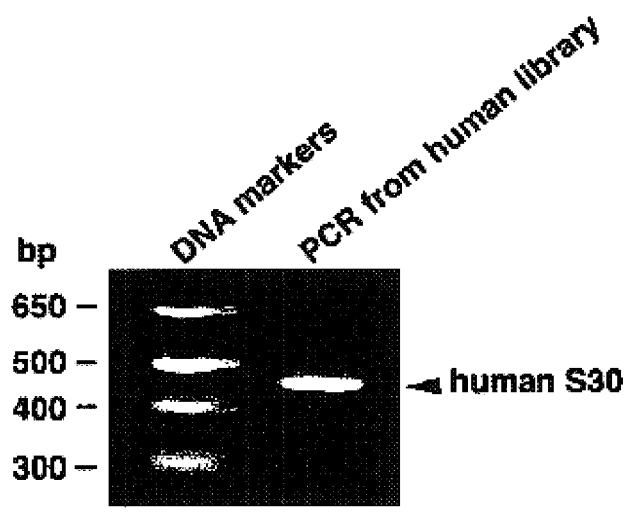
FIG. 38 shows the isolation of the cDNA for a nm-MIER gene from a human library. Using primers corresponding to the Xenopus sequence, a PCR (cDNA) product of the predicted size for the corresponding nm-MIER S30 sequence from a human library was amplified. These results demonstrate that, like er1, the human homologues of the Xenopus MIER genes can be isolated using Xenopus DNA sequences. This also serves as an example of the procedure to be followed to isolate the other members of the human MIER genes.
Figure 39:
FIG. 39 shows expression of ER1 protein in Xenopus embryos injected with synthetic er1 RNA (cRNA). cRNA was made by in vitro transcription of er1 cDNA in the expression vector pSP64T. Fertilized eggs were microinjected with 3 ng of er1 cRNA and allowed to develop for 4 hours. Embryos were fixed and stained with an anti-ER1 antibody of the invention. This demonstration provides evidence that ER1 protein can be expressed in the cells of this invention using the vector constructs of the invention.
Figure 41:
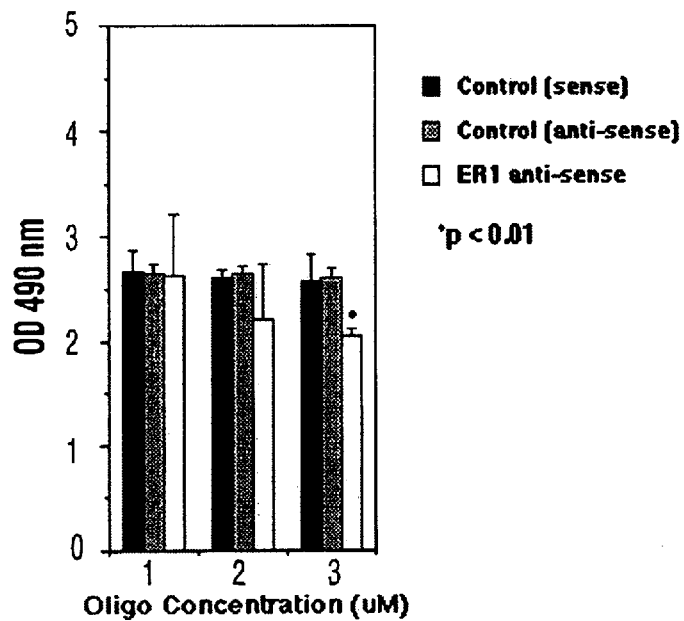
FIG. 41 evidences cell viability after 2 days treatment with oligonucleotides. These results show that treatment of human breast carcinoma cells with anti-sense er1 oligonucleotides reduces the number of viable cells. This data demonstrates that antisense oligonucleotides directed against er1 can inhibit the growth of human breast cancer cells. The statistical analysis indicates that the difference in growth is statistically significant as indicated by the asterix. These results demonstrate the use of oligonucleotides in anti-sense gene therapy.
Figure 42:
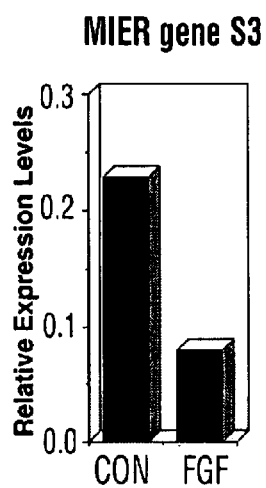
FIG. 42 shows that expression of nm-MIER gene S3 is downregulated within 30 minutes of FGF treatment. Expression levels were measured by PCR of reverse-transcribed RNA that was extracted from untreated (CON) and treated (FGF) Xenopus embryo explants. This histogram represents densitometric measurements of the PCR products and provides additional evidence that the MIER genes are regulated by FGF and provides a defining feature for genes belonging to this family.
Figure 43:
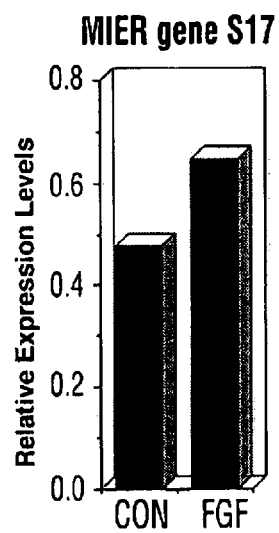
FIG. 43 shows that expression of nm-MIER gene S17 is upregulated within 30 minutes of FGF treatment. This histogram represents densitometric measurements of the PCR products and provides additional evidence that the nm-MIER genes are regulated by FGF and provides a defining feature for genes belonging to this family.
Figure 44:
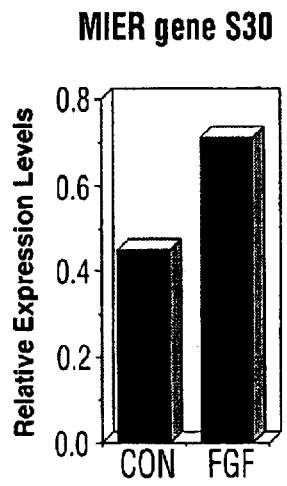
FIG. 44 shows the expression of nm-MIER gene S30 is upregulated within 30 minutes of FGF treatment. This histogram represents densitometric measurements of the PCR products and provides additional evidence that the MIER genes of the present invention are regulated by FGF and thus members of the family we have defined.
Figures 45, 47:
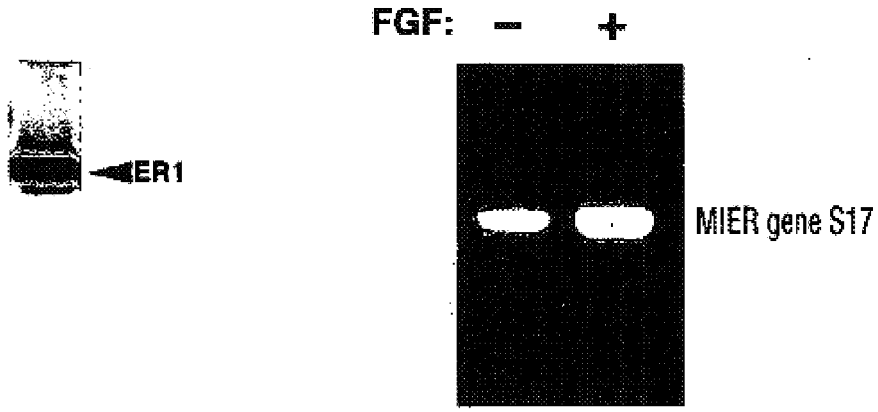
FIG. 45 demonstrates the results from the expression and purification of Xenopus ER1 protein from bacterial cells transformed with er1 cDNA in a bacterial expression vector. These results demonstrate that recombinant ER1 protein can be expressed and purified from bacterial sources. This provides a way to make large quantities of ER1 protein which may be used for vaccine protection other potential therapy.
FIG. 47 shows that nm-MIER gene S17 is upregulated by FGF. Xenopus embryo explants were incubated in the absence (1) or presence (+) of FGF for 30 min, RNA was extracted, reverse-transcribed and subjected to PCR using primers for the nm-MIER gene S17. These results present additional data to support the characterization that FGF can regulate nm-MIER genes and provides a defining feature for genes belonging to this family.

This example demonstrates that expression of er1 is tumor-specific. The expression in normal human tissues is very low. A special blot with 10× the amount of mRNA had to be used to enable visualization of any amount of expression, which could only be detected in four tissues (FIG. 24). FIG. 26 shows er1 expression results in actual tumor tissue rather than tumor cell lines. These studies in normal breast tissue and breast tumors demonstrate that er1 is not expressed at detectable levels in normal tissues, but that er1 is upregulated in cell lines, and more precisely, in tumor tissue. These studies support that er1 is tumor specific because the possibility exists that during the course of establishing a cell line, the cell's properties could be altered from the original tumor from which it was taken.

EXAMPLE II

Demonstration of the SANT Domain and Identification of an er1 Binding Site

The SANT domain is demonstrated to be a DNA binding domain of ER1. The SANT domain described in FIG. 3, has been used to affinity-purify the DNA sequence to which ER1 binds. The SANT domain can also be used to isolate all the genes that ER1 regulates. The ER1 consensus DNA binding sequence: GTTTC/GG is identified as the er1 binding site. Synthetic oligonucleotides, designed to bind to this ER1 consensus DNA binding sequence can be used to bind to mammalian DNA to inhibit er1 activity.

EXAMPLE III

Differential Nuclear Localization of ER1 Protein During Embryonic Development in *Xenopus laevis*

The er1 gene is a novel fibroblast growth factor (FGF)-regulated immediate-early gene, first isolated from Xenopus blastulae, that encodes a nuclear protein with potent transcription transactivational activity (Paterno et al., 1997). This example presents the expression pattern of the ER1 protein during Xenopus embryonic development. ER1 protein is present in the early embryo but does not begin to appear in the nucleus until mid-blastula stage. The first cells to show nuclear localization of ER1 are the presumptive mesodermal cells of the stage 8 blastula. ER1 gradually becomes localized to the nucleus of the remaining cells, first in the presumptive ectoderm and finally, in the presumptive endoderm such that by late blastula, all nuclei in the animal hemisphere are stained. By early gastrula, nuclear staining is ubiquitous. During subsequent development, ER1 protein gradually disappears from the nuclei of various tissues. In tailbud stages, ER1 begins to disappear from the nucleus of ectodermally-derived tissues, such as epidermis and brain, while remaining localized in the nucleus of endodermal cells and of mesodermal tissues, such as somites and notochord. In tadpoles, ER1 is no longer detectable in the nucleus of any cells, except for a few endodermal cells. Cytoplasmic staining, on the other hand, is observed in some mesodermal tissues, including somites and muscle cells. Neural tissue is largely unstained except for weak cytoplasmic staining in the eye.

Figure 8:
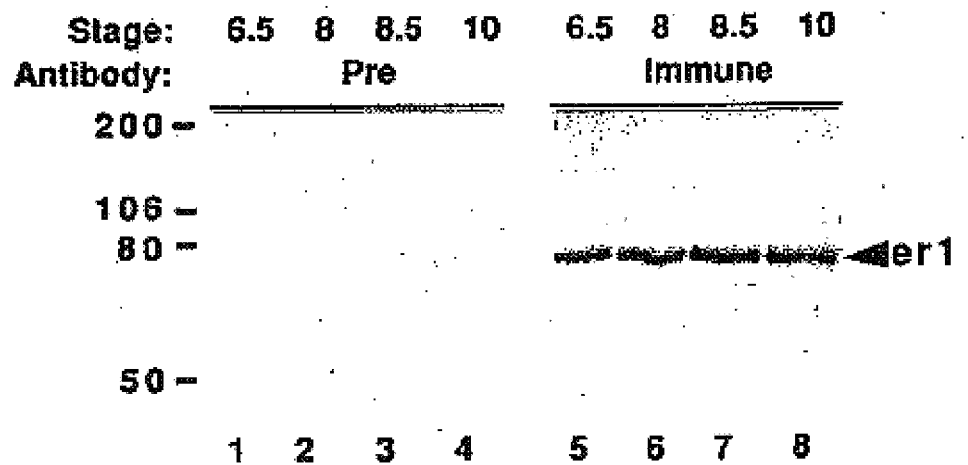
FIG. 8 demonstrates in nm-MIER studies that ER1 protein is expressed during early development. Embryo extracts from stages 6.5 (lanes 1 and 5), 8 (lanes 2 and 6), 8.5 (lanes 3 and 7) and 10 (lanes 4 and 8) were subjected to SDS-PAGE, blotted and stained with anti-ER1 (lanes 5–8). The blot was stripped and re-stained with pre-immune serum (lanes 1–4). The position of ER1 is indicated on the right and molecular weight standards are on the left.

It was demonstrated previously that er1 is an immediate-early gene whose expression is activated by FGF during mesoderm induction in Xenopus and whose gene product is targeted to the nucleus (Paterno et al., 1997). In this same report, er1 was shown to be a maternally-derived message whose expression is restricted to stages prior to mid-gastrula. Western blot analysis of ER1 protein expression during these same stages reveals that ER1 protein is detectable and that expression levels are similar for all stages examined (FIG. 8). In whole mounts and sections stained with anti-ER1 antibody, the first detectable staining is observed in the nucleus of marginal zone cells (presumptive mesoderm) of stage 8 blastulae (FIGS. 9A–D and FIG. 10), even though equivalent levels of ER1 protein are present at earlier stages (stage 6.5, FIG. 1; stage 2, not shown). Thus, ER1 protein is present in the cells of the early stage embryo but does not become concentrated in the nucleus until mid-blastula stage.

Figure 9:
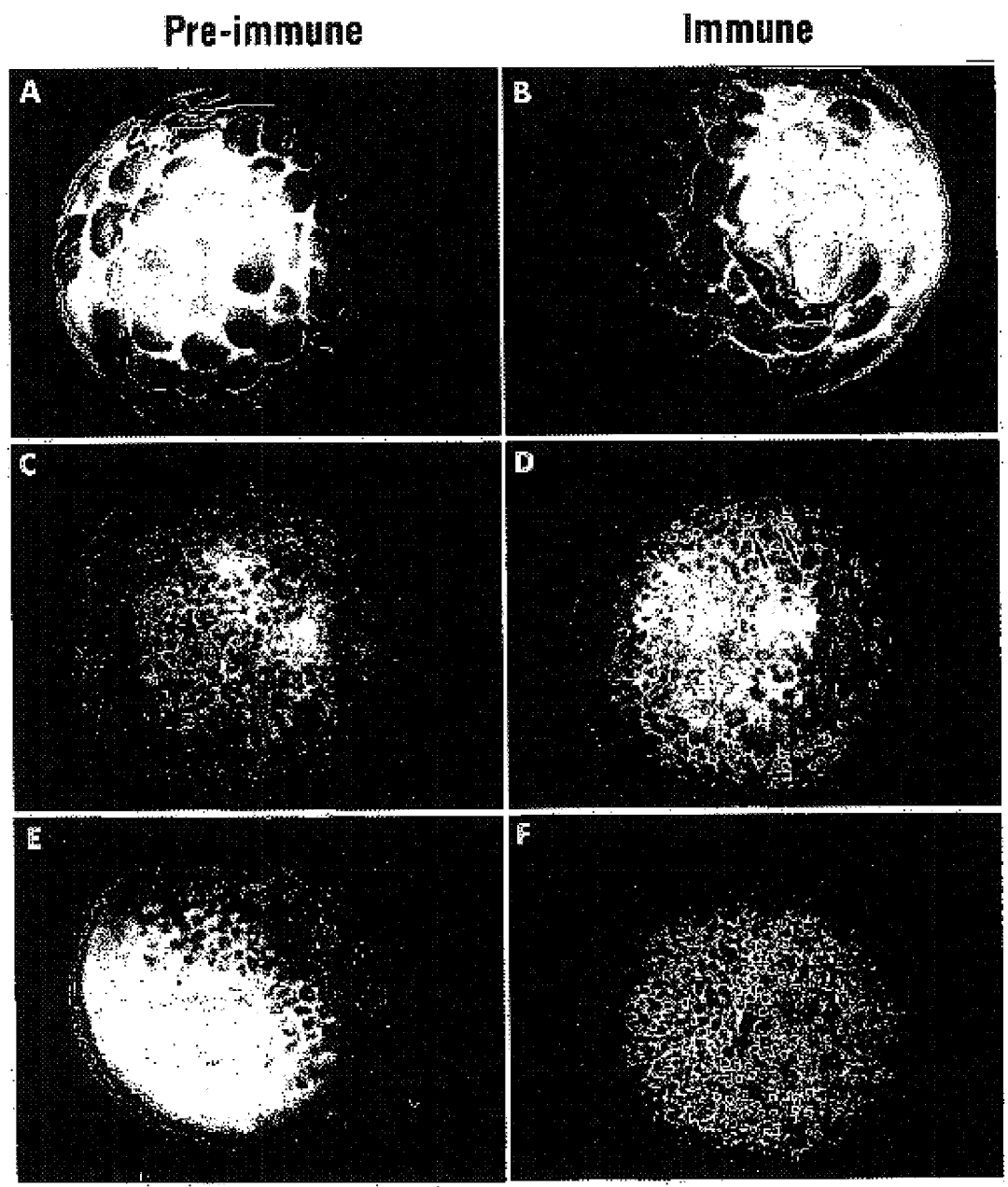
FIG. 9 shows results from nm-MIER studies that localization of ER1 to the nucleus begins during blastula stages. Albino embryos were fixed at stages 6.5 (A, B), 8 (C, D) or 8.5 (E, F) and stained with either pre-immune serum (A, C, E) or anti-ER1 (B, D, F). Nuclear staining (see arrows in D) first appears in the marginal zone cells (presumptive mesoderm) of stage 8 blastulae; by stage 8.5 (one additional cell division), virtually all nuclei in the animal hemisphere are stained (F). Bar=0.1 mm.
Figure 10:
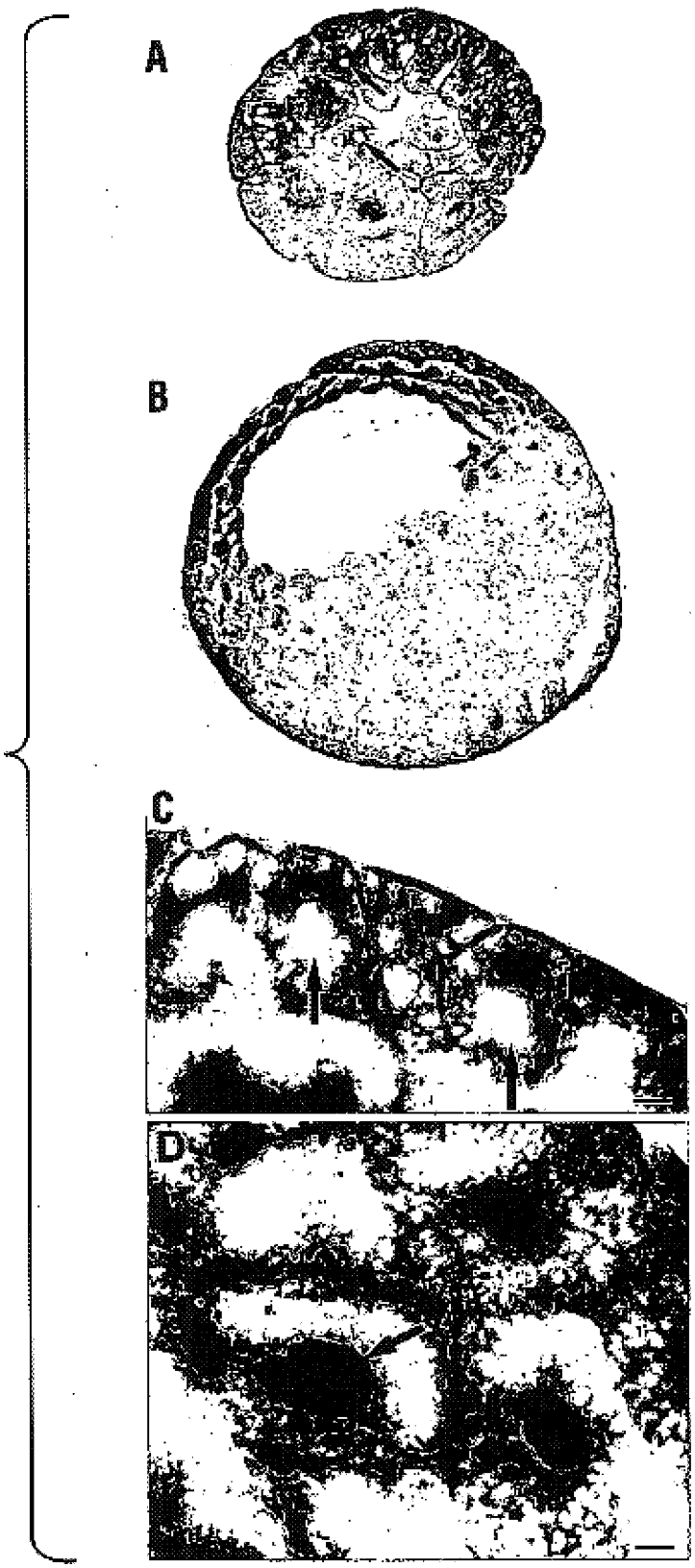
FIG. 10 shows in nm-MIER studies that ER1 is concentrated in the nucleus of marginal zone cells in stage 8 blastulae. Embryos were fixed at stages 6.5 (A) or 8 (B–D), sectioned and stained with anti-ER1. (A) The nuclei (arrows) remain unstained in early cleavage stages. (B–D) At stage 8, the nuclei (arrows in B and D) in the marginal zone begin to stain for ER1 while nuclei in the endoderm (B) as well as nuclei (arrows in C) in the rest of the animal hemisphere remain unstained. Bars=0.1 mm in A, B and 0.02 mm in C, D.
Figure 11:
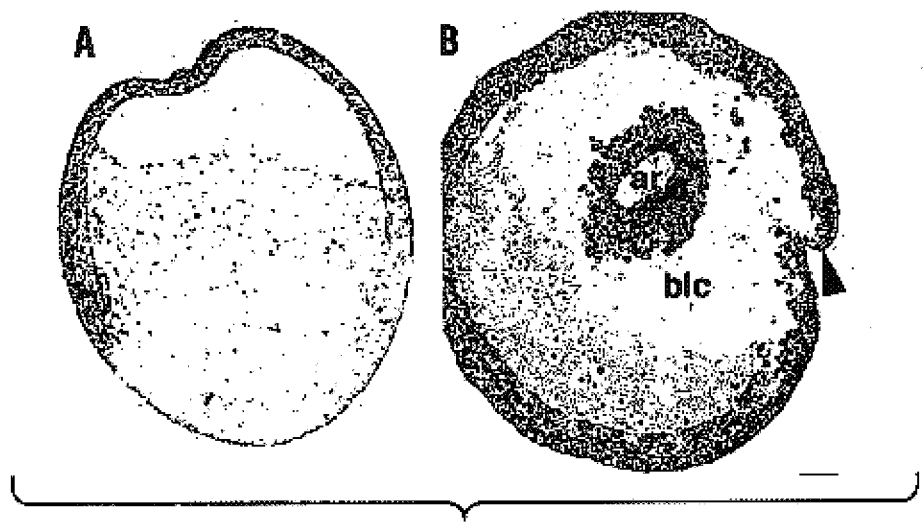
FIG. 11 presents evidence in nm-MIER studies indicating that ER1 is concentrated in the nucleus of all cells in stage 10 gastrulae. Embryos were fixed at stage 10, sectioned and stained with either pre-immune (A) or anti-ER1 (B). At stage 10, ER1 is concentrated in the nucleus in virtually all cells of the three germ layers; the arrow indicates the involuting lip; ar=archenteron; blc=blastocoel. Bars=0.1 mm.

As development proceeds, more nuclei become stained and by late blastula (stage 8.5–9), virtually all nuclei in the animal hemisphere are stained (FIGS. 9E, F). At this stage, the nuclei in the vegetal hemisphere begin to stain and by early gastrula (stage 10), ubiquitous nuclear staining is observed (FIG. 11).

Figure 12:
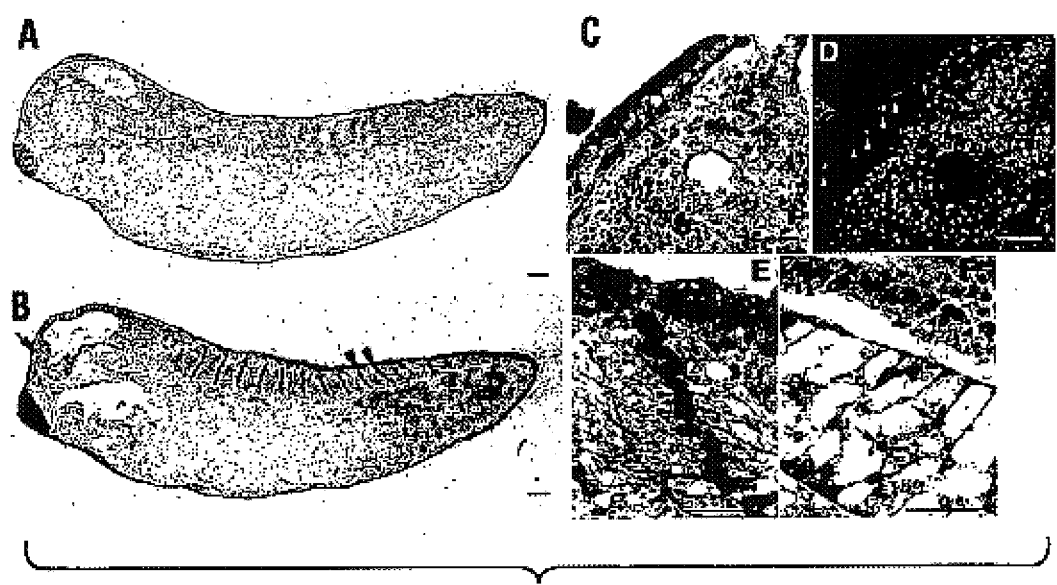
FIG. 12 demonstrates in nm-MIER studies that ER1 begins to disappear from the nucleus in the epidermis and brain during tailbud stages. Embryos were fixed at stage 27, sectioned and stained with either pre-immune (A) or anti-ER1 (B–F). At stage 27, nuclei are stained in the endoderm (B), somites (arrows in B and E), notochord (arrows in F) as well as in most of the spinal cord (tailed arrows in F). Many of the nuclei in the brain (tailed arrows in B–D) and epidermis (arrows in C–D) are no longer stained, as illustrated by comparing the anti-ER1 stained epidermis and brain in (C) with the same section incubated with a fluorescent nuclear stain (D). The black arrows in (C) mark the position of the nuclei identified by white arrows in (D). Bars=0.1 mm.
Figure 13:
FIG. 13 shows in nm-MIER studies that ER1 is no longer concentrated in the nucleus in stage 41 tadpoles. Embryos were fixed at stage 41, sectioned and stained with either pre-immune (A) or anti-ER1 (B–D). At stage 41, staining is absent from neural tissue (B) except for weak cytoplasmic staining in the eye (C). Staining in mesodermal tissues is exclusively cytoplasmic and is observed in somites (tailed arrows in B and bracket in D) as well as in muscle cells (black arrows in B and C). Nuclear staining is also absent in the epidermis (tailed black arrow in C) but is still observed in some of the endodermal cells (tailed red arrows in B). Bars=0.1 mm.
Figure 14:
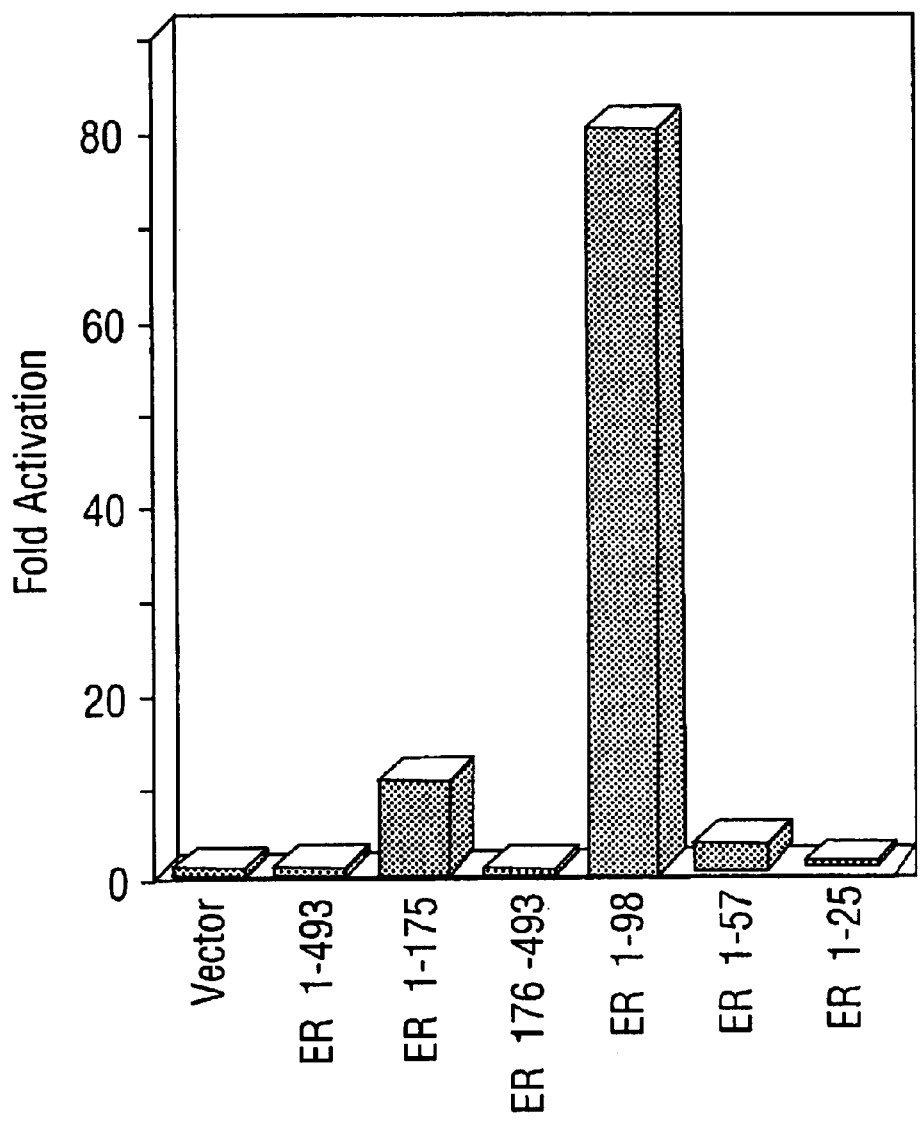
FIG. 14 shows the results of studies performed using Xenopus as an example of the nm-MIER family to demonstrate that the N-terminus of ER1 functions as a transcriptional activator. NIH 3T3 cells were transiently transfected with various GAL4-ER1 fusion constructs along with a CAT reporter plasmid. After 48 h, CAT enzyme levels were measured. Vector denotes the control pM plasmid, containing only the GAL4 DNA binding domain, while the numbers indicate the amino acids of ER1 encoded by each construct. The value for each construct represents the fold activation relative to the pM plasmid, averaged from 3–12 independent transfections.
Figures 15, 16:
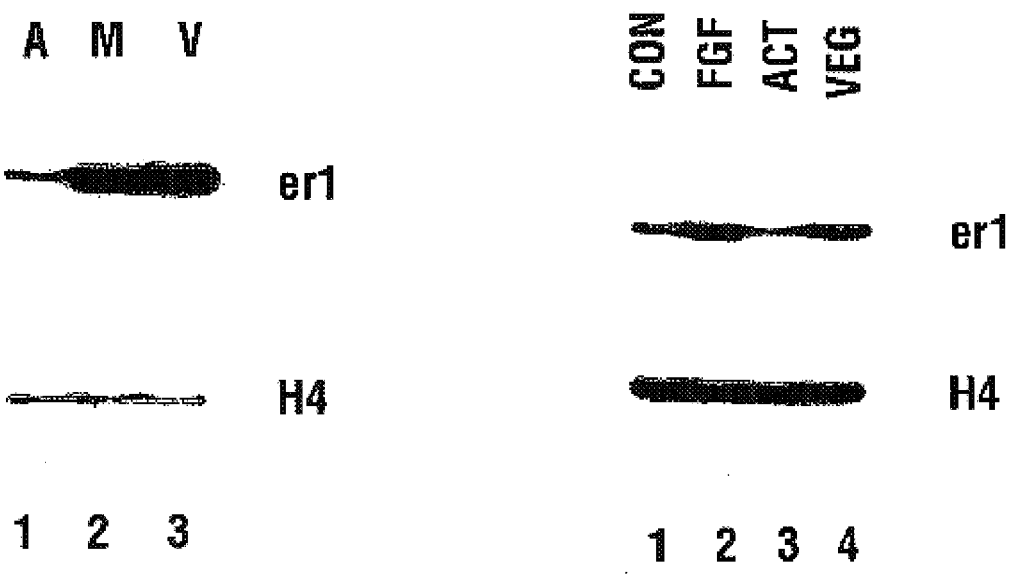
FIG. 15 presents a spatial expression pattern of er1 in Xenopus blastula stage embryos. Blastula stage embryos were dissected into presumptive ectoderm (A), presumptive mesoderm (M) and presumptive endoderm (V) explants. The explants were analyzed for er1 expression by RT-PCR. The top part of the diagram shows that er1 expression is highest in the presumptive mesoderm and endoderm and lowest in the presumptive ectoderm. The bottom part of the figure shows that the levels of RNA used were equivalent in all three conditions (normalization to Histone-H4).
FIG. 16 shows RT-PCR analysis for detection of er1 response to inducing factors in animal cap explants from blastula stage embryos. The top part of the diagram shows er1 levels and the bottom part shows normalization of the RNA used to Histone (H4). Lane 1—control explants, Lane 2—FGF treated explants, Lane 3—Activin treated explants, Lane 4—Vegetal (source of the natural inducer) treated explants. The results show that er1 is upregulated in response to FGF and vegetal treatment but not to activin.
Figure 17:
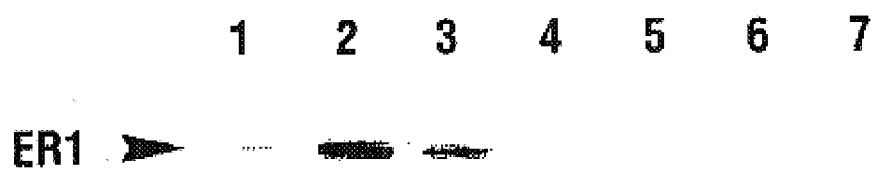
FIG. 17 shows blastula stage animal cap explants time course response to FGF. Lane 1—Time 0, Lane 2—30 minutes FGF treatment, Lane 3—1 hour, Lane 4—2 hours, Lane 5—4 hours 6—6 hours, lane 7—24 hours. er1 is upregulated within 30 minutes of FGF treatment and levels subsequently decrease to become undetectable by 4 hours. er1 is an early response gene in the signal transduction cascade triggered by FGF.
Figure 18:
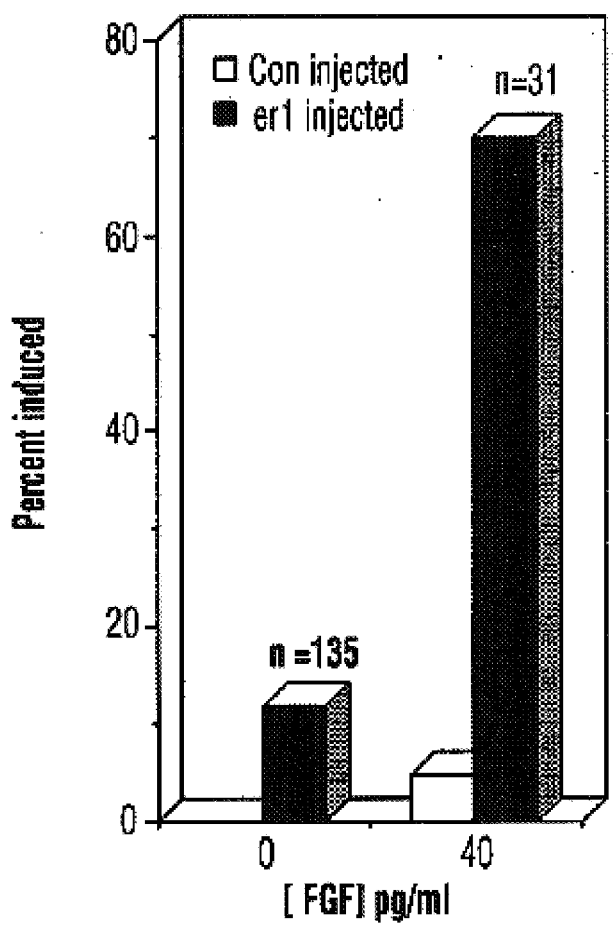
FIG. 18 shows Mesoderm induction by FGF in explants overexpressing ER1. This FIG. presents results of studies conducted using a member of the nm-MIER family showing that overexpression of ER1 results in induction in the absence of FGF and increased sensitivity to induction by FGF and increased sensitivity to induction by FGF. Control explants require 500 pg/ml FGF to achieve 70% induction. These results demonstrate that expression of Xenopus ER1 in embryonic cells is sufficient to induce mesoderm formation. When synthetic RNA for ER1 is injected into Xenopus embryonic cells in isolation, it is translated into protein and this protein can direct the differentiation of these cells into mesoderm derivatives. In addition, these embryonic cells expressing recombinant ER1 differentiate into mesoderm derivatives at low FGF concentrations which are insufficient to induce control cells. These data demonstrate that er1 can be expressed in these cells and that the protein produced is functional.
Figure 19:
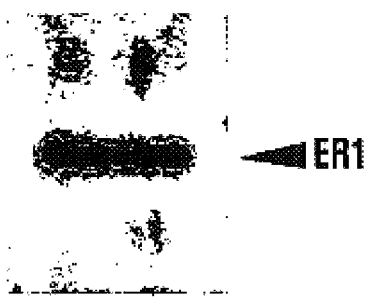
FIG. 19 shows ER1 is phosphorylated on tyrosine in studies using a member of the nm-MIER family. These results show ER1 is phosphorylated on tyrosine in Xenopus embryos. Protein extracts from blastula stage embryos undergoing mesoderm induction were immunoprecipitated with anti-ER1 antibodies. These immunoprecitates were subjected to Western blotting using anti-phosphotyrosine antibodies, which recognize phosphorylated tyrosine residues in all proteins, to reveal ER1 staining. The presence of an ER1 specific band demonstrates that ER1 can be phosphorylated on tyrosine. Tyrosine phosphorylation is important in the control of the function of many proteins. Knowing that ER1 is phosphorylated on tyrosine may provide a therapeutic approach to modulate its activity by modulating its phosphorylation state.
Figure 21:
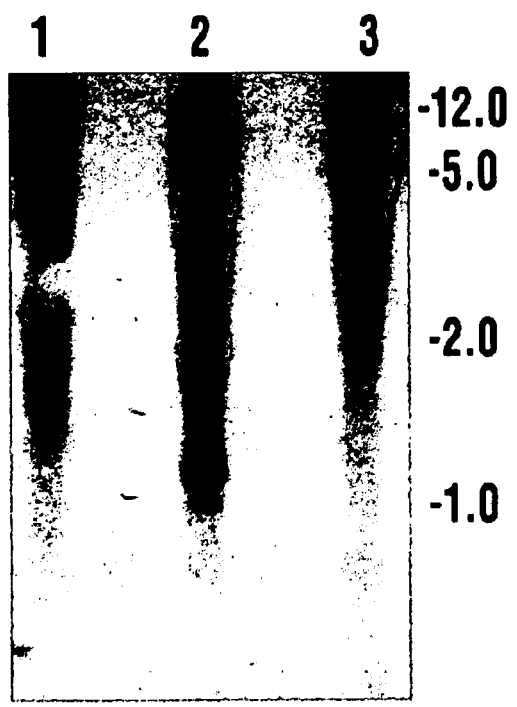
FIG. 21 presents results of a Southern blot analysis of human genomic DNA digested with EcoRV, XhoI, HindIII (lane 1), EcoRv, XhoI, EcoRI (lane 2) or EcoRV, XhoI, AvaI (lane 3) and probed for the presence of the er1 gene. Genomic DNA was purified from human cells and equivalent amounts were digested with the different combinations of restriction enzymes to cleave the DNA. This DNA was subjected to Southern blotting and probed with a cloned, radioactive er1 cDNA. The detectable bands reveal the size and complexity of the er1 gene in the human genome. DNA was digested with restriction enzymes EcoRV, XhoI, HindIII (lane 1), EcoRV, XhoI, EcoRI (lane 2) and EcoRV, XhoI, AvaI (lane 3). This data shows that er1, is present in the mammalian cell genome as a single copy gene. This is important since it indicates that there are no similar genes, duplicated genes or gene families for er1 whose gene product could mimic ER1 activity and/or escape the specific therapy designed to modulate er1 activity. It makes it simpler to design an effective therapy because one only has to target one gene.

During tailbud stages, endodermal and mesodermal tissues retain their nuclear staining (FIGS. 12B, E, F), however, in ectodermally-derived tissues, such as the brain and epidermis, nuclear staining begins to disappear (FIGS. 12C, D). This pattern of decreasing concentration of ER1 in the nucleus of various tissues continues throughout late development and by tadpole stage, nuclear staining is only observed in some endodermal nuclei (FIGS. 13A, B). At this stage of development, nuclear staining is no longer detected in any ectodermally or mesodermally-derived tissue (FIGS. 13B–D), however, cytoplasmic staining is observed in some mesodermal tissues (FIGS. 13B–D). Neural tissue is not stained except for weak cytoplasmic staining in the eye (FIGS. 13B, C).

Materials and Methods

*Xenopus laevis* embryos were obtained as described in Ryan and Gillespie (1994) and staged according to Nieuwkoop and Faber (1967). Antibody staining of whole-mount embryos, immunocytochemistry and nuclear staining of sectioned embryos was performed as previously described (Harland, 1991), using our anti-Xenopus ER1 antibody (Paterno et al., 1997) and an alkaline phosphatase-coupled goat-anti-rabbit secondary antibody (Life Technologies, Inc.). Nuclear staining was performed by incubating the slides in a 1:500 dilution of a live-cell nucleic acid stain (Molecular Probes).

Extracts from embryos at different developmental stages were prepared for Western blotting as described in Ryan and Gillespie (1994). The extracts were vortexed with an equal volume of freon and total protein was precipitated out of the aqueous layer with acetone. The pellet was resuspended in sample buffer and protein measurements were performed using the Bio-Rad assay to ensure equal loading of protein. The blots were stained using the ECL system (Amersham), as described in Ryan and Gillespie (1994).

References

Harland, R. M. 1991. Meth. Cell Biol. vol. 36, pp.683–695, eds. B. K. Kay and H. B. Peng, Academic Press, N.Y.
Nieuwkoop, P. D., and Faber, J. 1967. "Normal Table of *Xenopus laevis*." Amsterdam. 5 Holland
Paterno, G. D.; et al.,1997. *J. Biol. Chem.* 272, 25591–25595.
Ryan, P. J., and Gillespie, L. L. 1994. *Develop. Biol.* 166, 101–111.

EXAMPLE IV

Molecular Cloning of Human er1 cDNA and its Differential Expression in Breast Tumours and Tumour-Derived Cell Lines Based on the recently cloned and characterized nm-M-MIER gene, called er1, from Xenopus embryos whose expression levels were increased during mesoderm induction by fibroblast growth factor (FGF), we were able to isolate and describe the expression pattern of the human er1 sequence. Human ER1 and Xenopus ER1 proteins display 91% similarity; the amino acid sequence motifs, including the putative DNA-binding SANT domain, the predicted nuclear localization signals (NLS) and putative SH3 binding domain share 100% identity. er1 mRNA expression was negligible in all 50 normal human tissues analyzed. Examination of nine breast carcinoma-derived cell lines and eight breast tumour tissue samples by reverse transcription-polymerase chain reaction (RT-PCR) revealed that human er1 was consistently expressed in all tumour cell lines and tumour tissue while remaining undetectable in normal breast cell lines and breast tissue. These data suggest that er1 expression is associated with the neoplastic state in human breast carcinoma.

cDNA Cloning and Sequencing of Human er1

Using forward (F) and reverse (R) primers 5'-TCCGTTACACCAGGATGTAG-3' (F) and 5'-GGCTGAAATTCCAGTTGGTA-3' (R) designed according to the Xenopus er1 sequence, a 440 bp product was amplified from a human testis cDNA library (Clontech, Inc.), as described (Paterno et al., 1997). The cDNA was cloned into pCR2.1 (Invitrogen Inc.) (Paterno et al., 1997) and the sequence for both strands of this er1 cDNA and all subsequent cDNA inserts was determined as in Gillespie et al. (1995). A 1.6 kb cDNA was isolated from the human testis cDNA library using primers 5'-TGATCAGCTCCTGTGGGACC-3' (F) and 5'-CCAAATCGTGTTTGCTGAGC-3' (R) designed according to the sequence of the 440 bp human er1 cDNA and the testis library vector sequence 5'-GTTCCAGATTACGCTAGCTTGGG-3' (F) and 5'-CACAGTTGAAGTGAACTTGCGG-3' (R). The cDNAs were cloned into pCR2.1 and several clones were sequenced on both strands (Gillespie et al., 1995).

Cell Lines and Tumour Samples

The cell lines Hs574, Hs578, Hs787, BT-20, BT474, Hs578T, MCF-7, Sk-BR-3, MDA-157, MDA-231, MDA- 436 and MDA-468 (ATCC) were cultured under conditions described by the ATCC. Breast tumour samples were fixed in formalin and embedded in paraffin using standard histological methods known to those skilled in the art.

Dot Blot and PCR Analysis

Dot blot analysis was carried out as described in Paterno et al. (1997) with the following modifications: the dot blot and ExpressHyb solution were purchased from Clontech, Inc. and labelled probes were made using either human er1 3' untranslated region (3'UTR) or ubiquitin cDNA (Clontech, Inc.).

Total RNA for PCR analysis was prepared from the cell lines as described in Yang et al. (1997) and from sections of formalin-fixed, paraffin-embedded breast tumours as in Krafft et al. (1997). cDNA from normal breast tissue was purchased from Invitrogen, Inc. RT and PCR analysis were performed as described in Paterno et al. (1997), with the following modifications: β-actin was used as a control; the number of cycles in labelled PCR reactions was 26 for er1 and 24 for β-actin and in unlabelled reactions was 28 for both. For analysis of the cell lines, the human er1 primers were those listed in section 2.1 and the β-actin primers were as follows: 5'-ATCTGGCACCACACCTTCTACAATGAGCTGCG-3' (F) and 5'-CGTCATACTCCTGCTTGCTGATCCACATCTGC-3' (R). For the breast tumour samples, primer pairs were designed to amplify a sequence <200 bp and of similar size for both er1 and the control, β-actin, in order to control for the small target size generally recovered from formalin-fixed paraffin-embedded tissue (Krafft et al., 1997). The human er1 primers used: 5'-CAAGGGCTGAAGGCCTATGG-3' (F) and 5'-CCAAATCGTGTTTGCTGAGC-3' (R) generated a 146 bp product while the β-actin primers: 5'-ATCTGGCACCACACCTTCTACAATGAGCTGCG-3' (F) and 5'-ATGGCTGGGGTGTTGAAGGTCTC-3' (R) generated a 142 bp fragment. Densitometric analysis of the blot and PCR products was performed using a Canberra-Packard ChemiImager or Cyclone phosphorimager. The individual values obtained for er1 were divided by the ubiquitin (blot) or β-actin (PCR) values to obtain the relative level of er1 expression.

cDNA Cloning of Human er1

The cloning and characterization of er, a novel immediate-early gene from *Xenopus laevis* whose expression levels were increased by FGF was described recently (Paterno et al., 1997). Using primers based on the Xenopus sequence, a similar sequence was amplified from a human testis cDNA library. The full-length human cDNA consisted of a single open reading frame (ORF) of 1296 bp bracketed by a 68 bp 5'UTR containing an in-frame stop codon and a 210 bp 3'UTR containing an 18bp poly-A tail (FIG. 22). The ORF in the human er1 sequence is predicted to encode a protein of 432 amino acids (aa) (FIG. 22), producing a protein that has 61 fewer aa at the C-terminus than the Xenopus ER1 (FIG. 23).

Human ER1 displays 91% similarity to Xenopus ER1 at the amino acid level, with stretches of 100% identity (FIG. 23), indicating that ER1 is highly conserved between lower and higher vertebrates. Contained within the blocks of 100% identity are the protein sequence motifs identified previously in Xenopus ER1, namely the two predicted nuclear localization signals (NLS) and a proline-rich region corresponding to consensus for binding Src-homology 3 (SH3) domains (FIG. 23). Further sequence analysis revealed the presence of a SANT domain that is also 100% conserved between human and Xenopus ER1 (FIG. 23). The SANT domain is a recently described motif (Aasland et al., 1996), identified in self-comparisons of the co-repressor N-CoR and found in a number of other transcription factors including SW13, ADA2 and TFIIIB. The prior art also reported a similarity between this motif and the DNA binding domain of myb-related proteins, leading them to suggest that the SANT.domain is involved in DNA binding.

It was reported previously that Xenopus ER1 displays limited similarity (13%) to MTA1 (Toh et al., 1994), the product of the rat metastasis-associated gene, a 703 amino acid, 79 kDa polypeptide whose expression has been associated with the metastatic phenotype (Toh et al., 1994; Toh et al, 1995; Toh et al., 1997). Further examination has revealed that the similarity between ER1 and MTA1 lies in the SANT domain. Thus, ER1 and MTA1 may belong to the same class of transcriptional regulators that share a common DNA binding motif.

Expression of er1 in Normal Human Tissues and Tumour Cells

Initially, we examined the expression of human er1 by Northern blotting. However, on a blot prepared with total RNA from eight different human tissues, human er1 mRNA was barely detectable by phosphorimager analysis (data not shown). The estimated size of the single band observed was 1.5 kb which is consistent with the size of the cloned human er1 cDNA. Dot blot analysis of enriched poly A+ mRNA, a more sensitive detection procedure, confirmed that er1 was expressed at very low levels in normal human tissues (FIG. 24B). In all 50 tissues examined (FIG. 24A), er1 mRNA was not expressed at significant levels when compared to ubiquitin mRNA (FIG. 24C). Normalization of er1 to ubiquitin levels by densitometry revealed that expression of er1 in the testis, intestinal tract (small intestine and colon), spleen, adrenal glands as well as in the adult and fetal thymus was slightly higher (1.5–2.5 times) than in the other tissues.

Figure 25:
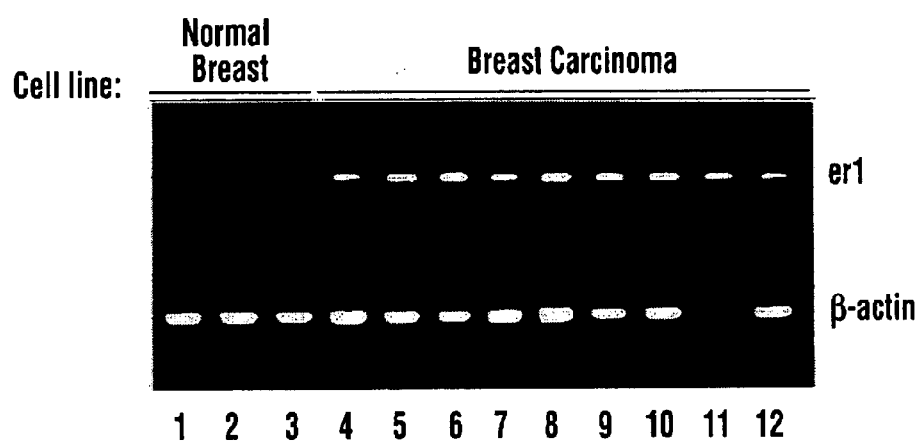
FIG. 25 demonstrates expression of human er1 in normal breast and breast carcinoma cell lines. RT-PCR was performed on RNA extracted from normal breast cell lines: Hs574, Hs578, Hs787 (lanes 1–3) and from breast carcinoma cell lines: BT-20, BT-474, Hs578T, MCF-7, Sk-BR-3, MDA-157, MDA-231, MDA-436 and MDA-468 (lanes 4–12) to amplify human er1 (top panel) or β-actin (bottom panel) as a control. The PCR products were analyzed on a 1% agarose gel.

FGFs play a role in the pathology of a number of human cancers, therefore, it was decided to investigate the expression of er1 in human tumour cell lines and tumour tissue. Examination of breast carcinoma cell lines revealed consistent expression of er1 in all nine lines examined, while er1 was not detectable in the three normal breast cell lines, even when the sensitive PCR method was employed (FIG. 25). On occasion, a faint band was obtained for er1 in the Hs574 cell line, but not for the other two normal cell lines, Hs578 and Hs787. Many of the available normal breast cell lines, like Hs574, are in fact derived from histologically normal tissue surrounding a breast tumour. Thus, the results with the Hs574 cell line may either reflect a low level of er1 expression in normal cells or may be indicative of a mixed population in this cell line.

Examination of er1 expression in breast tumour samples by RT-PCR revealed a pattern similar to that observed for the cell lines (FIG. 26). er1 mRNA was expressed in all breast tumour samples tested, albeit at variable levels (FIG. 26A, lanes 1–3; 26B, lanes 1–8), while remaining undetectable in normal breast tissue (FIG. 26A, lane 4; 26B, lane N).

Expression studies demonstrate that er1 mRNA is not present at significant levels in normal human adult or fetal tissues. This is consistent with the expression pattern observed in Xenopus, where er1 mRNA was only detectable by Northern blot during pre-gastrula stages of development and not in later stages (Paterno et al., 1997).

Although the function of er1 is yet to be determined, its expression pattern points to a role in early embryonic development and, like many other developmental-regulated genes, overexpression in adult tissues may contribute to the neoplastic phenotype.

This example presents the cloning and expression analysis of the human homologue of er1. Comparison of the Xenopus and human ER1 proteins reveals a high degree of conservation between lower and higher vertebrates.

Human er1 mRNA expression was negligible in all normal tissues and breast cell lines examined, but was upregulated in breast carcinoma cell lines and in breast tumours, suggesting that expression of er1 is associated with the neoplastic state in human breast carcinomas.

References

Aasland, R., Stewart, A. F., Gibson, T., 1996, Trends Biochem. Sci. 21, 87–88.
Friesel, R. and Maciag, T., 1995. *FASEB J.* 9, 919–925.
Gillespie, L. L., Chen, G. and Paterno, G. D., 1995. *J. Biol. Chem.* 270, 22758–22763.
Krafft, A. E., et al., 1997. *Mol. Diag.* 2, 217–230.
Paterno, G. D., et al.,. *J. Biol. Chem.* 272, 25591–25595.
Toh, Y., Pencil, S. D. and Nicolson, G. L., 1994. *J. Biol. Chem.* 269, 22958–22963.
Toh, Y., Pencil, S. D. and Nicolson, G. L., 1995. *Gene* 159, 97–104.
Toh, Y., et al., 1997, *Int. J. Cancer* 74, 459463.
Yang, X., et al., 1997. *J. Cell. Biochem.* 66, 309–321.

The embodiments of the invention in which an exclusive property or privilege is claimed are defined as follows:

1. An isolated polynucleotide comprising a nucleic acid selected from the group consisting of:
   (a) a nucleic acid encoding a mesoderm immediate early response (MIER) protein ER1, which comprises a nucleic acid sequence as set forth in SEQ ID NO: 9;
   (b) a nucleic acid which is at least 90% identical to (a) and which encodes a polypeptide which has the activity of the MIER ER1 polypeptide as set forth in SEQ ID NO: 10;
   (c) a nucleic acid that will hybridize to the nucleic acid of (a) or (b) under the following conditions: hybridization followed by a final wash having 0.02M sodium ion concentration at 63° C.; and
   (d) a nucleic acid which is the complement of the nucleic acid of (a) or (b).

2. The isolated polynucleotide according to claim 1, wherein the polynucleotide is DNA.

3. A vector comprising the isolated polynucleotide of claim 1.

4. A host cell transformed or transfected with the polynucleotide of claim 1, wherein said host cell is in vitro.

5. The isolated polynucleotide of claim 1 herein the polynucleotide is fused to a heterologous polynucleotide.

6. The isolated polynucleotide of claim 1, wherein two or more of said polynucleotides are arranged in tandem array in an amplicon.

7. An expression vector containing the isolated polynucleotide of claim 1.

8. An expression vector containing the isolated polynucleotide of claim 5.

9. An expression vector containing the isolated polynucleotide of claim 6.

10. The expression vector of any one of claim 7, 8, or 9, wherein said vector comprises a bacterial phage in recombinant form.

11. The expression vector of any one of claim 7, 8, or 9, wherein said vector comprises a plasmid in recombinant form.

12. The expression vector of any one of claim 7, 8 or 9 wherein said vector is selected from the group consisting of pcDNA$_3$; pIRES; pCR$_{2.1}$; pSP$_{64}$T; and pT$_7$Ts.

13. A host cell comprising the expression vector of claim 7, wherein said host cell is in vitro.

14. The isolated polynucleotide of claim 1, wherein said polynucleotide is RNA.

15. A DNA probe which is the complement of at least a portion of the isolated polynucleotide of claim 1, part (a), wherein said probe is at least about 70 nucleotides in length.

16. An RNA probe which is complementary to at least a portion of the isolated polynucleotide of claim 1.

17. An RNA probe which is complementary to at least a portion of the DNA of claim 2.

18. The probe of claim 15 or 16, wherein said probe is labeled with a detectable marker.

19. The probe of claim 18, wherein said marker is radioactive.

20. The probe of claim 18, wherein said marker is fluorescent.

21. The probe of claim 18, wherein said marker is biotinylated.

22. A bioassay for detection of M-MIER gene expression comprising:
   (a) contacting a tissue sample with a probe of claim 18, under conditions such that regions of DNA or messenger RNA (mRNA) in said tissue sample and said probe with complementary sequences will base pair so that a RNA:probe or DNA:probe complex is formed; and
   (b) detecting the presence or absence of said RNA:probe or DNA:probe complex, thereby detecting M-MIER gene expression.

23. A diagnostic kit comprising the probe of claim 18 and reagents to effect formation of and detection of an RNA:DNA or RNA:RNA complex and instructions for use of said kit.

24. An antisense oligonucleotide which is the complement of
   a nucleic acid encoding a mesoderm immediate early response (MIER) protein ER1, which comprises a nucleic acid sequence as set forth in SEQ ID NO: 9.

25. The antisense oligonucleotide of claim 24 that is DNA.

26. The antisense oligonucleotide of claim 24 that is RNA.

27. A method of inhibiting the expression of the human M-MIER er1 (SEQ ID NO: 9) gene comprising contacting tissues or cells in vitro with an amount of the antisense oligonucleotide of claim 24 effective to inhibit the expression of said human M-MIER er1 gene.

28. The method of claim 27 wherein said expression of M-MIER er1 genes is abnormal expression.

29. A method of inhibiting hyperproliferation of human cells comprising contacting hyperproliferating human cells in vitro with an amount of the antisense oligonucleotide of claim 22 effective to inhibit hyperproliferation of human cells.

30. The isolated polynucleotide according to claim 2, wherein the DNA is cDNA.

31. An isolated nucleic acid comprising at least 6 contiguous nucleotides that are complementary to SEQ ID NO: 9.

32. The isolated polynucleotide of claim 1 wherein the polynucleotide encodes the polypeptide encoded by SEQ ID NO: 9.

33. The isolated polynucleotide of claim 1 wherein the polynucleotide encodes a human MIER er1 polypeptide.

* * * * *

SEQUENCE LISTING

<160> NUMBER OF SEQ ID NOS: 32

<210> SEQ ID NO 1
<211> LENGTH: 2339
<212> TYPE: DNA
<213> ORGANISM: Xenopus laevis
<220> FEATURE:
<221> NAME/KEY: CDS
<222> LOCATION: (233)..(1714)

<400> SEQUENCE: 1

```
ttgcatcagc tgcagatcaa ggttaaaata tatatatcag aagaatacac aaataattaa        60
attaaatgtc tcaaacaact ccttccatat gaaggcctct ctgtacctgt gcagcgtttt       120
tcaaaacaga gcaaggaatt catacattac aaatatattt gttgtgtcat aagctacaga       180
gaaagttata gtgaaaccaa caaaacataa atgacccgtc agtacggcaa ac atg gcg       238
                                                             Met Ala
                                                               1 gag cct tca ctc agg acc gca agc cca ggt ggc tcg gct gca tca gat        286
Glu Pro Ser Leu Arg Thr Ala Ser Pro Gly Gly Ser Ala Ala Ser Asp
          5                  10                  15 gac cat gag ttt gag cca tca gct gac atg ctt gtt cat gaa ttt gat        334
Asp His Glu Phe Glu Pro Ser Ala Asp Met Leu Val His Glu Phe Asp
 20                  25                  30 gat gaa caa acg ttg gaa gaa gag gag atg ctg gag gga gaa gtc aac        382
Asp Glu Gln Thr Leu Glu Glu Glu Glu Met Leu Glu Gly Glu Val Asn
 35                  40                  45                  50 ttc act tca gaa ata gag cac ctt gaa aga gaa agt gaa atg cca att        430
Phe Thr Ser Glu Ile Glu His Leu Glu Arg Glu Ser Glu Met Pro Ile
              55                  60                  65 gat gaa tta ttg cga ctc tat ggt tat ggc agt aca gtg cca cta cca        478
Asp Glu Leu Leu Arg Leu Tyr Gly Tyr Gly Ser Thr Val Pro Leu Pro
              70                  75                  80 gga gaa gaa gat gag gag gat atg gat aat gat tgt aac agt ggc tgc        526
Gly Glu Glu Asp Glu Glu Asp Met Asp Asn Asp Cys Asn Ser Gly Cys
                  85                  90                  95 agt gga gaa ata aag gat gaa gct att aag gac tct tca gga cag gaa        574
Ser Gly Glu Ile Lys Asp Glu Ala Ile Lys Asp Ser Ser Gly Gln Glu
            100                 105                 110 gat gaa aca cag tct tca aat gat gat cct act cca tct ttt aca tgt        622
Asp Glu Thr Gln Ser Ser Asn Asp Asp Pro Thr Pro Ser Phe Thr Cys
115                 120                 125                 130 aga gat gta cga gaa gta atc cgt cca cgt cgg tgc aag tat ttt gat        670
Arg Asp Val Arg Glu Val Ile Arg Pro Arg Arg Cys Lys Tyr Phe Asp
                    135                 140                 145
```

-continued

```
aca aat cat gaa ata gaa gag gag tct gag gat gat gag gat tat gta      718
Thr Asn His Glu Ile Glu Glu Glu Ser Glu Asp Asp Glu Asp Tyr Val
            150                 155                 160 cct tca gaa gat tgg aaa aag gaa att atg gtg gga tcc atg ttc cag      766
Pro Ser Glu Asp Trp Lys Lys Glu Ile Met Val Gly Ser Met Phe Gln
        165                 170                 175 gct gaa att cca gtt ggt att tgc aaa tac aga gaa aca gag aaa gta      814
Ala Glu Ile Pro Val Gly Ile Cys Lys Tyr Arg Glu Thr Glu Lys Val
    180                 185                 190 tat gaa aat gat gat cag ctc ctc tgg aat cca gaa tat gta atg gaa      862
Tyr Glu Asn Asp Asp Gln Leu Leu Trp Asn Pro Glu Tyr Val Met Glu
195                 200                 205                 210 gaa aga gta ata gac ttc tta aat gag gca tcc aga agg act tgt gaa      910
Glu Arg Val Ile Asp Phe Leu Asn Glu Ala Ser Arg Arg Thr Cys Glu
                215                 220                 225 gag aga ggg cta gat gct att cct gaa gga tcc cac ata aag gac aat      958
Glu Arg Gly Leu Asp Ala Ile Pro Glu Gly Ser His Ile Lys Asp Asn
            230                 235                 240 gag cag gcc cta tat gaa cat gta aaa tgc aat ttt gac aca gaa gag     1006
Glu Gln Ala Leu Tyr Glu His Val Lys Cys Asn Phe Asp Thr Glu Glu
        245                 250                 255 gca ttg aga aga cta aga ttt aat gtc aaa gcc gcc aga gaa gaa ctt     1054
Ala Leu Arg Arg Leu Arg Phe Asn Val Lys Ala Ala Arg Glu Glu Leu
    260                 265                 270 tcc gtt tgg act gaa gaa gaa tgt aga aat ttt gag caa ggt cta aaa     1102
Ser Val Trp Thr Glu Glu Glu Cys Arg Asn Phe Glu Gln Gly Leu Lys
275                 280                 285                 290 gct tat ggc aaa gat ttc cac ttg att cag gct aac aag gta agg aca     1150
Ala Tyr Gly Lys Asp Phe His Leu Ile Gln Ala Asn Lys Val Arg Thr
                295                 300                 305 agg tct gtt gga gaa tgt gtg gca ttc tac tac atg tgg aaa aaa tca     1198
Arg Ser Val Gly Glu Cys Val Ala Phe Tyr Tyr Met Trp Lys Lys Ser
            310                 315                 320 gaa cgt tat gac ttc ttt gcc caa caa aca cga ttt gga aaa aag aag     1246
Glu Arg Tyr Asp Phe Phe Ala Gln Gln Thr Arg Phe Gly Lys Lys Lys
        325                 330                 335 tat aat cta cat cct ggt gta acg gat tac atg gat cgt ctt ttg gat     1294
Tyr Asn Leu His Pro Gly Val Thr Asp Tyr Met Asp Arg Leu Leu Asp
    340                 345                 350 gaa agc gaa agt gct acc tcc agc agg gcg cca tct ccc cca cca act     1342
Glu Ser Glu Ser Ala Thr Ser Ser Arg Ala Pro Ser Pro Pro Pro Thr
355                 360                 365                 370 acc tcc aac agc aat act agt caa tcc gaa aag gag gac tgt aca gcc     1390
Thr Ser Asn Ser Asn Thr Ser Gln Ser Glu Lys Glu Asp Cys Thr Ala
                375                 380                 385 agt aac aac act cag aat gga gtt tct gtg aat ggc cca tgt gca ata     1438
Ser Asn Asn Thr Gln Asn Gly Val Ser Val Asn Gly Pro Cys Ala Ile
            390                 395                 400 act gca tac aaa gat gaa gcc aaa caa ggg gtg cat tta aat gga cct     1486
Thr Ala Tyr Lys Asp Glu Ala Lys Gln Gly Val His Leu Asn Gly Pro
        405                 410                 415 act ata agt agc agt gat ccc tct tcg aat gaa acc gac acc aat ggg     1534
Thr Ile Ser Ser Ser Asp Pro Ser Ser Asn Glu Thr Asp Thr Asn Gly
    420                 425                 430 tat aat cgt gaa aat gtt acg gac gat tcc aga ttt agt cat aca agt     1582
Tyr Asn Arg Glu Asn Val Thr Asp Asp Ser Arg Phe Ser His Thr Ser
435                 440                 445                 450 gga aaa act gac aca aat cca gat gat aca aac gaa agg cca ata aaa     1630
Gly Lys Thr Asp Thr Asn Pro Asp Asp Thr Asn Glu Arg Pro Ile Lys
```

|                                                                                      |      |
|--------------------------------------------------------------------------------------|------|
| 455 460 465                                                                          |      |
| agg caa cgt atg gac agc cct ggg aag gaa agt aca gga tca tct gaa                      | 1678 |
| Arg Gln Arg Met Asp Ser Pro Gly Lys Glu Ser Thr Gly Ser Ser Glu                      |      |
|             470                 475                 480                              |      |
| ttc tct cag gaa gtg ttt tca cat gga gag gtt taa acattttgca                           | 1724 |
| Phe Ser Gln Glu Val Phe Ser His Gly Glu Val                                          |      |
|             485                 490                                                  |      |
| gatttgaggg aaaacacatt ttgggggat gaagaaattt ctggggatct tggaacttca                     | 1784 |
| gggtttatta aattatttag caagttattt ttttgtatta tttttctatt tgtcccatgc                    | 1844 |
| acatttgagc cccacagaag agtgaaatat tttgtgtagt tgaatagtga aatttttgaa                    | 1904 |
| gccctctgga aaagtaagca gccttgcaga tattcagcct atgcctgaat gcagtttggc                    | 1964 |
| tttacgttat cattcgttac atgaagaagg atctttaaat agaaaagaa ttgttccaga                     | 2024 |
| atatgtctgc agtgttgttg cagtggaaaa tattaaccct gaaagttgtt ggtatgattt                    | 2084 |
| tttttaggta ggtgttaaga ataaaccaaa tgaggtttgt gtatgtaatt tattgacatc                    | 2144 |
| aatgatgtct ttcctattct tatctgggct gaaaaagata cattctgtat ttttccagat                    | 2204 |
| ctctttgtag cctttgaaag attttacat tatctatgtt ttgatcgaac tgcctttctt                     | 2264 |
| aacaaagctt gtataatttt cttaacttgt acagttgata aactttatt atgaaaagga                     | 2324 |
| aaaaaaaaaa aaaaa                                                                     | 2339 |

<210> SEQ ID NO 2
<211> LENGTH: 493
<212> TYPE: PRT
<213> ORGANISM: Xenopus laevis

<400> SEQUENCE: 2

Met Ala Glu Pro Ser Leu Arg Thr Ala Ser Pro Gly Gly Ser Ala Ala
 1               5                  10                  15

Ser Asp Asp His Glu Phe Glu Pro Ser Ala Asp Met Leu Val His Glu
             20                  25                  30

Phe Asp Asp Glu Gln Thr Leu Glu Glu Glu Met Leu Glu Gly Glu
         35                  40                  45

Val Asn Phe Thr Ser Glu Ile Glu His Leu Glu Arg Glu Ser Glu Met
     50                  55                  60

Pro Ile Asp Glu Leu Leu Arg Leu Tyr Gly Tyr Gly Ser Thr Val Pro
 65                  70                  75                  80

Leu Pro Gly Glu Glu Asp Glu Gly Asp Met Asp Asn Asp Cys Asn Ser
                 85                  90                  95

Gly Cys Ser Gly Glu Ile Lys Asp Glu Ala Ile Lys Asp Ser Ser Gly
            100                 105                 110

Gln Glu Asp Glu Thr Gln Ser Ser Asn Asp Asp Pro Thr Pro Ser Phe
        115                 120                 125

Thr Cys Arg Asp Val Arg Glu Val Ile Arg Pro Arg Cys Lys Tyr
    130                 135                 140

Phe Asp Thr Asn His Glu Ile Glu Glu Glu Ser Glu Asp Asp Glu Asp
145                 150                 155                 160

Tyr Val Pro Ser Glu Asp Trp Lys Lys Glu Ile Met Val Gly Ser Met
                165                 170                 175

Phe Gln Ala Glu Ile Pro Val Gly Ile Cys Lys Tyr Arg Glu Thr Glu
            180                 185                 190

Lys Val Tyr Glu Asn Asp Asp Gln Leu Leu Trp Asn Pro Glu Tyr Val
        195                 200                 205

```
Met Glu Glu Arg Val Ile Asp Phe Leu Asn Glu Ala Ser Arg Arg Thr
    210                 215                 220
Cys Glu Glu Arg Gly Leu Asp Ala Ile Pro Glu Gly Ser His Ile Lys
225                 230                 235                 240
Asp Asn Glu Gln Ala Leu Tyr Glu His Val Lys Cys Asn Phe Asp Thr
                245                 250                 255
Glu Glu Ala Leu Arg Arg Leu Arg Phe Asn Val Lys Ala Ala Arg Glu
            260                 265                 270
Glu Leu Ser Val Trp Thr Glu Glu Cys Arg Asn Phe Glu Gln Gly
        275                 280                 285
Leu Lys Ala Tyr Gly Lys Asp Phe His Leu Ile Gln Ala Asn Lys Val
    290                 295                 300
Arg Thr Arg Ser Val Gly Glu Cys Val Ala Phe Tyr Tyr Met Trp Lys
305                 310                 315                 320
Lys Ser Glu Arg Tyr Asp Phe Phe Ala Gln Gln Thr Arg Phe Gly Lys
                325                 330                 335
Lys Lys Tyr Asn Leu His Pro Gly Val Thr Asp Tyr Met Asp Arg Leu
            340                 345                 350
Leu Asp Glu Ser Glu Ser Ala Thr Ser Ser Arg Ala Pro Ser Pro Pro
        355                 360                 365
Pro Thr Thr Ser Asn Ser Asn Thr Ser Gln Ser Glu Lys Glu Asp Cys
    370                 375                 380
Thr Ala Ser Asn Asn Thr Gln Asn Gly Val Ser Val Asn Gly Pro Cys
385                 390                 395                 400
Ala Ile Thr Ala Tyr Lys Asp Glu Ala Lys Gln Gly Val His Leu Asn
                405                 410                 415
Gly Pro Thr Ile Ser Ser Ser Asp Pro Ser Ser Asn Glu Thr Asp Thr
            420                 425                 430
Asn Gly Tyr Asn Arg Glu Asn Val Thr Asp Asp Ser Arg Phe Ser His
        435                 440                 445
Thr Ser Gly Lys Thr Asp Thr Asn Pro Asp Asp Thr Asn Glu Arg Pro
    450                 455                 460
Ile Lys Arg Gln Arg Met Asp Ser Pro Gly Lys Glu Ser Thr Gly Ser
465                 470                 475                 480
Ser Glu Phe Ser Gln Glu Val Phe Ser His Gly Glu Val
                485                 490

<210> SEQ ID NO 3
<211> LENGTH: 498
<212> TYPE: DNA
<213> ORGANISM: Xenopus laevis

<400> SEQUENCE: 3
ctgctctcag atgcaatgac aacactatct ctattccagg atgacttcaa gtcaaatgtt      60
gatgttgttt agttgctaag ttatgtctga ctcttttgca accccatgga ctatagccca     120
cctctgtcca taggatttcc caggcaagaa tactggatgg tttgccattt ctctaggaaa     180
tctttccaac ccagggactg aacccacatc ttgtgcttgg caaccgattc tttaccactg     240
agccactagg gaagccctta agtcatata agtaatgtt aatttcagaa tgctttcata     300
tcaaagttaa gagcccagat aaattttaaa tggctgtgaa tccattgcag ctattcccac     360
caagagttgg agtctatttt caacactctc cccttactct gggctggatc tatgactttc     420
tttggccaac agactgtgct acttcaatac ttaccttctt accagacact tctatcttgt     480
gaaggagcct gagagcag                                                   498
```

<210> SEQ ID NO 4
<211> LENGTH: 450
<212> TYPE: DNA
<213> ORGANISM: Xenopus laevis

<400> SEQUENCE: 4

| ctgctctcag | aaaaatgcta | tagagacgta | tatgacataa | ataatctgtg | atgaaacaat | 60 |
| ttaggtttca | ttagcttttta | caaaaatgga | aaaagtatga | ccatggttgc | acagtttggc | 120 |
| aaaccatttt | ttctatcatt | cctacaaaat | actactgagt | gttactggac | actgatatga | 180 |
| ttattaaaga | tattctttat | ataaattgta | tatcaataaa | ttataatatg | cagagtaggt | 240 |
| tgcagttacc | tacttaccta | cttacagaag | caattatcac | taaactgctg | acatgccagt | 300 |
| ttggttgttc | agcatacttc | agtacaaaca | agaagcttct | ggagtttcca | gtacactgca | 360 |
| ttttatacaa | atgtaacgta | taggctcata | aacctaaagc | acactagtta | tttagattta | 420 |
| ctacatacat | aaagatacac | agctgagcag | | | | 450 |

<210> SEQ ID NO 5
<211> LENGTH: 686
<212> TYPE: DNA
<213> ORGANISM: Xenopus laevis

<400> SEQUENCE: 5

| ttcgttttgt | ttcagtaaat | agtatttgca | tttattatgt | atacagcaaa | atagacatct | 60 |
| gatgcaaatt | agaagtgtag | gctggtacta | acatggctga | gctagaagtt | taggtaagga | 120 |
| aaagatgagg | aaaagagaca | gctagtgctc | atactgcatt | gccccattcc | ttcaaaatgg | 180 |
| aatgtaggcc | aattttgttg | tcacaaattc | agcagataaa | catctttcaa | taaggaaatc | 240 |
| acagaaaata | cttggaatac | tgagaattga | gacaacgcaa | caataatact | ttgtacagat | 300 |
| gctggctggt | accctaaatt | tgtacccaca | gtattcccag | ttcatgcctc | aagtaaaata | 360 |
| caaaatatag | aagatgccca | gcagtaacgt | tcaatgtaat | gattcaagag | attgtcagaa | 420 |
| aaaaatacat | attagatatg | gctctgataa | ggaatgggag | tcaagtgtga | taacaggaat | 480 |
| ggcacaccct | tcttatagtt | aagcaagctc | tttgccactt | tatatcagct | tattgcccat | 540 |
| ggataagcac | ctgcttctcc | tttcctgaaa | gaattaagtg | tagtcccaac | ttggacacct | 600 |
| aatatatggt | gattcaaagc | tgaatatcca | gggaacaaca | gaatattcat | caaggagtg | 660 |
| tcctttatta | tgtgaagaac | catttt | | | | 686 |

<210> SEQ ID NO 6
<211> LENGTH: 636
<212> TYPE: DNA
<213> ORGANISM: Xenopus laevis

<400> SEQUENCE: 6

| ctgatccatg | gtttaagtat | aaataattgt | tcacttatat | ctgtttcaat | cacctttcat | 60 |
| tgtagttccc | aaaatctcgc | ctaaatcata | catctgccca | accaaccttc | taacagcaat | 120 |
| gttagggatg | gattcaaaaa | gatctttgag | gaaattgggt | ggcagatacg | cgctaacaaa | 180 |
| gatgagtgat | agaaacacaa | tggtgattac | tcccaatcag | tataattcaa | atagtataat | 240 |
| gggtataaca | gtaatagagt | acatgacatg | ttaggcactt | actttgctgt | gccaaaggta | 300 |
| ttcccatcac | tttgtctctc | agagacacca | acagatagct | gtggcctaat | ccctatctgt | 360 |
| gtaccctgct | ttaacccaaa | ctaattgaca | aactcgaaat | cgatggtgct | aattcaccac | 420 |

```
cccatctat tgagagtaca tgctctccat gttatgttag caataggata aatccttatt      480 ttcttttttcc tatctccctc tggactcccc atgatctcta ttttcccaat cgtcggtttc    540
ttgcatccta agtaatatcc tcttcaggat acactcatgc ctgctagaag gattaacaaa    600
tgaattaggc atgataacga ttattgcatg gatcag                               636

<210> SEQ ID NO 7
<211> LENGTH: 191
<212> TYPE: DNA
<213> ORGANISM: Xenopus laevis

<400> SEQUENCE: 7
ctgatccatg cgtatagcct tgaataataa agctttgctc cctctaaatg acaaatacca    60
caatccacta ctaccaccta tgactgcact tgaacttaca agtaactaag ggaacaagag    120
ggggataaga aaacagaagt acagaactat cgcaatgact gctttgtgat cttatttcct    180
acatggatca g                                                         191

<210> SEQ ID NO 8
<211> LENGTH: 516
<212> TYPE: DNA
<213> ORGANISM: Xenopus laevis

<400> SEQUENCE: 8
tgatccatga aaagtgttag tgaccaacct tctggatatc ttccattccc gaaacctgat    60
gatactcagt actttgacaa attattggtt gatgttgatg aatctacgct aagtccagaa    120
gaacagaaag aaagaaaaat aatgaaatta ttgttaaaaa taaagatgg cacacctcca    180 atgaggaagg ctgccttgcg acaaataact gataaagctc gtgagtttgg agccggtcca    240
ctattcaatc agatcctgcc tctgctgatg tcgccaacac ttgaagatca agaaagacac    300
ttgcttgtta agttattga tagaattttg tataaattgg atgacttggt ccgcccatat    360
gtacataaga ttcttgtcgt tattgaacca cttctgattg atgaagacta ttatgccaga    420
gtggaaggca gagaaatcat atctaattta gccaaggctg ctggtttagc tacaatgatt    480
tcaactatgc gaccagatat tgataacatg gatcag                              516

<210> SEQ ID NO 9
<211> LENGTH: 1574
<212> TYPE: DNA
<213> ORGANISM: Homo sapiens
<220> FEATURE:
<221> NAME/KEY: CDS
<222> LOCATION: (69)..(1367)

<400> SEQUENCE: 9
gggtcggacg ccagctgcgg acgccagctg cggccgccgc ggagatgtga ggcggcagta    60 cggcaaat atg gcg aca tct gtt gaa tct tca agt cca gga ggt tca gca    110
         Met Ala Thr Ser Val Glu Ser Ser Ser Pro Gly Gly Ser Ala
           1               5                   10 aca tca gat gac cat gaa ttt ggt cca tca act gac atg ctg gtt cat    158
Thr Ser Asp Asp His Glu Phe Gly Pro Ser Thr Asp Met Leu Val His
 15                  20                  25                  30 gat ttt gat gat gaa cga aca tta gaa gag gaa gaa atg atg gaa gga    206
Asp Phe Asp Asp Glu Arg Thr Leu Glu Glu Glu Glu Met Met Glu Gly
                 35                  40                  45 gaa aca aac ttc agc tct gaa ata gaa gat ctt gca agg gaa ggc gac    254
Glu Thr Asn Phe Ser Ser Glu Ile Glu Asp Leu Ala Arg Glu Gly Asp
             50                  55                  60
```

```
atg cca att cat gaa ctt ctc agc ctt tat ggt tat ggt agt act gtt      302
Met Pro Ile His Glu Leu Leu Ser Leu Tyr Gly Tyr Gly Ser Thr Val
         65                  70                  75 cga cta cct gaa gaa gat gag gaa gag gaa gaa gga gaa gaa ggt          350
Arg Leu Pro Glu Glu Asp Glu Glu Glu Glu Glu Gly Glu Glu Gly
     80                  85                  90 gaa gat gat gaa gat gct gat aat gat gac aac agt ggc tgt agt ggg      398
Glu Asp Asp Glu Asp Ala Asp Asn Asp Asp Asn Ser Gly Cys Ser Gly
 95                 100                 105                 110 gaa aat aaa gag gag aat ata aag gat tca tca ggt cag gag gat gaa      446
Glu Asn Lys Glu Glu Asn Ile Lys Asp Ser Ser Gly Gln Glu Asp Glu
             115                 120                 125 act cag tct tcc aat gat gat cca tca caa tct gtt gct tct caa gat      494
Thr Gln Ser Ser Asn Asp Asp Pro Ser Gln Ser Val Ala Ser Gln Asp
         130                 135                 140 gcc cag gaa ata atc cgc cca cgt cga tgt aaa tat ttt gat aca aat      542
Ala Gln Glu Ile Ile Arg Pro Arg Arg Cys Lys Tyr Phe Asp Thr Asn
             145                 150                 155 agt gaa gta gaa gaa gaa tct gaa gaa gat gaa gat tat att cca tca      590
Ser Glu Val Glu Glu Glu Ser Glu Glu Asp Glu Asp Tyr Ile Pro Ser
    160                 165                 170 gaa gac tgg aaa aag gag att atg gtg ggc tcc atg ttt caa gca gaa      638
Glu Asp Trp Lys Lys Glu Ile Met Val Gly Ser Met Phe Gln Ala Glu
175                 180                 185                 190 att cca gtt ggc atg tgt aga tac aaa gaa aat gaa aaa gta tat gaa      686
Ile Pro Val Gly Met Cys Arg Tyr Lys Glu Asn Glu Lys Val Tyr Glu
             195                 200                 205 aat agt gat cag ctc ctg tgg gac cct gag tac tta cca gaa gat aaa      734
Asn Ser Asp Gln Leu Leu Trp Asp Pro Glu Tyr Leu Pro Glu Asp Lys
         210                 215                 220 gtg att ata ttt ctt aaa gat gca tct aga aga aca ggt gat gag aag      782
Val Ile Ile Phe Leu Lys Asp Ala Ser Arg Arg Thr Gly Asp Glu Lys
             225                 230                 235 ggt gta gaa gca att cct gaa gga tct cac ata aaa gac aat gaa cag      830
Gly Val Glu Ala Ile Pro Glu Gly Ser His Ile Lys Asp Asn Glu Gln
    240                 245                 250 gct tta tat gaa ttg gtt aaa tgc aat ttt gat aca gaa gaa gca ttg      878
Ala Leu Tyr Glu Leu Val Lys Cys Asn Phe Asp Thr Glu Glu Ala Leu
255                 260                 265                 270 aga aag tta aga ttt aat gta aaa gca gct aga gag gaa tta tct gtt      926
Arg Lys Leu Arg Phe Asn Val Lys Ala Ala Arg Glu Glu Leu Ser Val
             275                 280                 285 tgg aca gag gaa gag tgt aga aat ttt gaa caa ggg ctg aag gcc tat      974
Trp Thr Glu Glu Glu Cys Arg Asn Phe Glu Gln Gly Leu Lys Ala Tyr
         290                 295                 300 gga aag gat ttt cat ttg att cag gct aat aaa gtc cga aca agg tca     1022
Gly Lys Asp Phe His Leu Ile Gln Ala Asn Lys Val Arg Thr Arg Ser
             305                 310                 315 gtt ggt gaa tgt gta gca ttc tat tac atg tgg aaa aaa tct gaa cgt     1070
Val Gly Glu Cys Val Ala Phe Tyr Tyr Met Trp Lys Lys Ser Glu Arg
    320                 325                 330 tat gat ttc ttt gct cag caa aca cga ttt gga aag aag aaa tat aat     1118
Tyr Asp Phe Phe Ala Gln Gln Thr Arg Phe Gly Lys Lys Lys Tyr Asn
335                 340                 345                 350 ctt cat cct ggt gta acg gat tac atg gat cgt ctt cta gac gaa agt     1166
Leu His Pro Gly Val Thr Asp Tyr Met Asp Arg Leu Leu Asp Glu Ser
             355                 360                 365 gaa agt gct gca tct agt cga gca cca tcc cct ccc cca act gca tca     1214
Glu Ser Ala Ala Ser Ser Arg Ala Pro Ser Pro Pro Pro Thr Ala Ser
         370                 375                 380
```

```
aac agt agt aac agc cag tct gag aaa gaa gat ggc act gta agc act      1262
Asn Ser Ser Asn Ser Gln Ser Glu Lys Glu Asp Gly Thr Val Ser Thr
            385                 390                 395 gcc aat caa aat gga gtg tca tct aat gga cct agc ata ctc caa atg      1310
Ala Asn Gln Asn Gly Val Ser Ser Asn Gly Pro Ser Ile Leu Gln Met
    400                 405                 410 ctt ctt cca gtt cat ttt tca gcc atc agt tca aga gcc aat gcc ttt      1358
Leu Leu Pro Val His Phe Ser Ala Ile Ser Ser Arg Ala Asn Ala Phe
415                 420                 425                 430 tta aaa taa agcttctgtg gtcttgtttt taatggctca actgtctgat              1407
Leu Lys gtaattgagt gaaggtttgc actgagaaat tagcattcag gccttacccc catgaagtat    1467
tactgttaac atatgttcgg actgcttccc ttcaccaatg tgaacaactt tttttcccaa    1527
acagtattaa aagccacttt gcaacactta aaaaaaaaaa aaaaaaa                  1574

<210> SEQ ID NO 10
<211> LENGTH: 432
<212> TYPE: PRT
<213> ORGANISM: Homo sapiens

<400> SEQUENCE: 10

Met Ala Thr Ser Val Glu Ser Ser Pro Gly Gly Ser Ala Thr Ser
  1               5                  10                  15

Asp Asp His Glu Phe Gly Pro Ser Thr Asp Met Leu Val His Asp Phe
             20                  25                  30

Asp Asp Glu Arg Thr Leu Glu Glu Glu Met Met Glu Gly Glu Thr
             35                  40                  45

Asn Phe Ser Ser Glu Ile Glu Asp Leu Ala Arg Glu Gly Asp Met Pro
     50                  55                  60

Ile His Glu Leu Leu Ser Leu Tyr Gly Tyr Gly Ser Thr Val Arg Leu
 65                  70                  75                  80

Pro Glu Glu Asp Glu Glu Glu Glu Glu Gly Glu Glu Gly Glu Asp
                 85                  90                  95

Asp Glu Asp Ala Asp Asn Asp Asp Asn Ser Gly Cys Ser Gly Glu Asn
                100                 105                 110

Lys Glu Glu Asn Ile Lys Asp Ser Ser Gly Gln Glu Asp Glu Thr Gln
            115                 120                 125

Ser Ser Asn Asp Asp Pro Ser Gln Ser Val Ala Ser Gln Asp Ala Gln
        130                 135                 140

Glu Ile Ile Arg Pro Arg Arg Cys Lys Tyr Phe Asp Thr Asn Ser Glu
145                 150                 155                 160

Val Glu Glu Glu Ser Glu Glu Asp Glu Asp Tyr Ile Pro Ser Glu Asp
                165                 170                 175

Trp Lys Lys Glu Ile Met Val Gly Ser Met Phe Gln Ala Glu Ile Pro
            180                 185                 190

Val Gly Met Cys Arg Tyr Lys Glu Asn Glu Lys Val Tyr Glu Asn Ser
        195                 200                 205

Asp Gln Leu Leu Trp Asp Pro Glu Tyr Leu Pro Glu Asp Lys Val Ile
    210                 215                 220

Ile Phe Leu Lys Asp Ala Ser Arg Arg Thr Gly Asp Glu Lys Gly Val
225                 230                 235                 240

Glu Ala Ile Pro Glu Gly Ser His Ile Lys Asp Asn Glu Gln Ala Leu
                245                 250                 255

Tyr Glu Leu Val Lys Cys Asn Phe Asp Thr Glu Glu Ala Leu Arg Lys
```

```
                    260                 265                 270
Leu Arg Phe Asn Val Lys Ala Ala Arg Glu Glu Leu Ser Val Trp Thr
            275                 280                 285

Glu Glu Glu Cys Arg Asn Phe Glu Gln Gly Leu Lys Ala Tyr Gly Lys
        290                 295                 300

Asp Phe His Leu Ile Gln Ala Asn Lys Val Arg Thr Arg Ser Val Gly
305                 310                 315                 320

Glu Cys Val Ala Phe Tyr Tyr Met Trp Lys Lys Ser Glu Arg Tyr Asp
                325                 330                 335

Phe Phe Ala Gln Gln Thr Arg Phe Gly Lys Lys Lys Tyr Asn Leu His
            340                 345                 350

Pro Gly Val Thr Asp Tyr Met Asp Arg Leu Leu Asp Glu Ser Glu Ser
            355                 360                 365

Ala Ala Ser Ser Arg Ala Pro Ser Pro Pro Thr Ala Ser Asn Ser
        370                 375                 380

Ser Asn Ser Gln Ser Glu Lys Glu Asp Gly Thr Val Ser Thr Ala Asn
385                 390                 395                 400

Gln Asn Gly Val Ser Ser Asn Gly Pro Ser Ile Leu Gln Met Leu Leu
                405                 410                 415

Pro Val His Phe Ser Ala Ile Ser Ser Arg Ala Asn Ala Phe Leu Lys
            420                 425                 430

<210> SEQ ID NO 11
<211> LENGTH: 367
<212> TYPE: DNA
<213> ORGANISM: Murinae gen. sp.

<400> SEQUENCE: 11
gagtacttac cagaagataa agtgattata tttcttaaag atgcatctag aagaacaggt      60
gatgagaagg gtgtagaagc aattcctgaa ggatctcaca taaagacaa tgaacaggct     120 ttatatgaat tggttaaatg caattttgat acagaagaag cattgacaac attaagattt    180
aatgtaaaag cagctagaga ggaattatct gtttggacag aggaagagtg tagaaatttt    240
gaacaagggc tgaaggccta tggaaaggat ttcatttga ctcaggctaa taaagtccga    300
acaaggtcag ttggtgaatg tgcagcattc tattacatga aaaaaatctg aacgttatga    360
tttctttt                                                             367

<210> SEQ ID NO 12
<211> LENGTH: 122
<212> TYPE: PRT
<213> ORGANISM: Murinae gen. sp.

<400> SEQUENCE: 12

Glu Tyr Leu Pro Glu Asp Lys Val Ile Ile Phe Leu Lys Asp Ala Ser
 1               5                  10                  15

Arg Arg Thr Gly Asp Glu Lys Gly Val Glu Ala Ile Pro Glu Gly Ser
            20                  25                  30

His Ile Lys Asp Asn Glu Gln Ala Leu Tyr Glu Leu Val Lys Cys Asn
        35                  40                  45

Phe Asp Thr Glu Glu Ala Leu Thr Thr Leu Arg Phe Asn Val Lys Ala
    50                  55                  60

Ala Arg Glu Glu Leu Ser Val Trp Thr Glu Glu Cys Arg Asn Phe
65                  70                  75                  80

Glu Gln Gly Leu Lys Ala Tyr Gly Lys Asp Phe His Leu Thr Gln Ala
                85                  90                  95
```

```
Asn Lys Val Arg Thr Arg Ser Val Gly Glu Cys Ala Ala Phe Tyr Tyr
            100                 105                 110
Met Lys Lys Asn Leu Asn Val Met Ile Ser
        115                 120

<210> SEQ ID NO 13
<211> LENGTH: 504
<212> TYPE: DNA
<213> ORGANISM: Homo sapiens

<400> SEQUENCE: 13
ggctgaaatt ccagttggta tttgtagata caaagaaaat gaaaagtat  atgaaaatga    60 tgatcagctc ctgtgggacc ctgagtactt accagaagat aaagtgatta tatttcttaa   120
agatgcatct agaagaacag gtgatgagaa gggtgtagaa gcaattcctg aaggatctca   180
cataaaagac aatgaacagg ctttatatga attggttaat gcaattttga ttacagaaga   240
agcattgaga agattagatt tatgtaaagc agctagagag atatctgttt ggacagagga   300
agagtgtaga aattttgaac aagggctgaa ggcctatgga gaggattttc atttgatttc   360
attcaggctt aataaagtcc gaacaaggtc agttggtgaa tgtgtagcat tctattacat   420
gtggaaaaaa tctgaacgtt atgatttctt tgctcagcaa acacgatttg gaaagaagaa   480
atataatcta catcctggtg taac                                          504

<210> SEQ ID NO 14
<211> LENGTH: 167
<212> TYPE: PRT
<213> ORGANISM: Homo sapiens

<400> SEQUENCE: 14

Ala Glu Ile Pro Val Gly Ile Cys Arg Tyr Lys Glu Asn Glu Lys Val
 1               5                  10                  15
Tyr Glu Asn Asp Asp Gln Leu Leu Trp Asp Pro Glu Tyr Leu Pro Glu
            20                  25                  30
Asp Lys Val Ile Ile Phe Leu Lys Asp Ala Ser Arg Arg Thr Gly Asp
        35                  40                  45
Glu Lys Gly Val Glu Ala Ile Pro Glu Gly Ser His Ile Lys Asp Asn
    50                  55                  60
Glu Gln Ala Leu Tyr Glu Leu Val Asn Ala Ile Leu Ile Thr Glu Glu
65                  70                  75                  80
Ala Leu Arg Arg Leu Asp Leu Cys Lys Ala Ala Arg Glu Ile Ser Val
                85                  90                  95
Trp Thr Glu Glu Glu Cys Arg Asn Phe Glu Gln Gly Leu Lys Ala Tyr
            100                 105                 110
Gly Glu Asp Phe His Leu Ile Ser Phe Arg Leu Asn Lys Val Arg Thr
        115                 120                 125
Arg Ser Val Gly Glu Cys Val Ala Phe Tyr Tyr Met Trp Lys Lys Ser
    130                 135                 140
Glu Arg Tyr Asp Phe Phe Ala Gln Gln Thr Arg Phe Gly Lys Lys Lys
145                 150                 155                 160
Tyr Asn Leu His Pro Gly Val
                165

<210> SEQ ID NO 15
<211> LENGTH: 36
<212> TYPE: DNA
<213> ORGANISM: Homo sapiens
```

<400> SEQUENCE: 15
ctcccagtgc ctggctgagt ttcggacgtg gttaag    36

<210> SEQ ID NO 16
<211> LENGTH: 28
<212> TYPE: DNA
<213> ORGANISM: Homo sapiens

<400> SEQUENCE: 16
gggtcggacg ccagctgcgg acgccagc    28

<210> SEQ ID NO 17
<211> LENGTH: 73
<212> TYPE: DNA
<213> ORGANISM: Homo sapiens

<400> SEQUENCE: 17
aaccaactgg ttgaggttca atgcagacaa gacggatgtg atgctgccat ctgttgaatc    60
ttcaagtcca gga    73

<210> SEQ ID NO 18
<211> LENGTH: 73
<212> TYPE: DNA
<213> ORGANISM: Homo sapiens

<400> SEQUENCE: 18
tgcggccgcc gcggagatgt gaggcggcag tacggcaaat atggcgacat ctgttgaatc    60
ttcaagtcca gga    73

<210> SEQ ID NO 19
<211> LENGTH: 58
<212> TYPE: DNA
<213> ORGANISM: Homo sapiens

<400> SEQUENCE: 19
gatgtgaccc ggcagtacgg caaatatggc ggctcgtgtt gaatcttcaa gtccagga    58

<210> SEQ ID NO 20
<211> LENGTH: 6
<212> TYPE: PRT
<213> ORGANISM: Homo sapiens

<400> SEQUENCE: 20

Met Leu Pro Ser Val Glu
 1               5

<210> SEQ ID NO 21
<211> LENGTH: 6
<212> TYPE: PRT
<213> ORGANISM: Homo sapiens

<400> SEQUENCE: 21

Met Ala Thr Ser Val Glu
 1               5

<210> SEQ ID NO 22
<211> LENGTH: 6
<212> TYPE: PRT
<213> ORGANISM: Homo sapiens

<400> SEQUENCE: 22

```
Met Ala Ala Arg Val Glu
  1               5
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: pcr
      oligonucleotide

<400> SEQUENCE: 23
tccgttacac caggatgtag                                           20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:  pcr
      oligonucleotide

<400> SEQUENCE: 24
ggctgaaatt ccagttggta                                           20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:  pcr
      oligonucleotide

<400> SEQUENCE: 25
tgatcagctc ctgtgggacc                                           20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:  pcr
      oligonucleotide

<400> SEQUENCE: 26
ccaaatcgtg tttgctgagc                                           20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:  pcr
      oligonucleotide

<400> SEQUENCE: 27
gttccagatt acgctagctt ggg                                       23

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:  pcr
      oligonucleotide

<400> SEQUENCE: 28

-continued

```
cacagttgaa gtgaacttgc gg                                            22

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: pcr
      oligonucleotide

<400> SEQUENCE: 29
atctggcacc acaccttcta caatgagctg cg                                 32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: pcr
      oligonucleotide

<400> SEQUENCE: 30
cgtcatactc ctgcttgctg atccacatct gc                                 32

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: pcr
      oligonucleotide

<400> SEQUENCE: 31
caagggctga aggcctatgg                                               20

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: pcr
      oligonucleotide

<400> SEQUENCE: 32
atggctgggg tgttgaaggt ctc                                           23
```